US005770697A

United States Patent [19]

Ferrari et al.

[11] Patent Number: 5,770,697

[45] Date of Patent: Jun. 23, 1998

[54] PEPTIDES COMPRISING REPETITIVE UNITS OF AMINO ACIDS AND DNA SEQUENCES ENCODING THE SAME

[75] Inventors: Franco A. Ferrari, La Jolla, Calif.; Charles Richardson, Florence, Mont.; James Chambers, San Diego, Calif.; Stuart Causey, Palo Alto, Calif.; Thomas J. Pollock, San Diego, Calif.; Joseph Cappello, San Diego, Calif.; John W. Crissman, San Diego, Calif.

[73] Assignee: Protein Polymer Technologies, Inc., San Diego, Calif.

[21] Appl. No.: 477,509

[22] Filed: Jun. 7, 1995

(Under 37 CFR 1.47)

Related U.S. Application Data

[63] Continuation-in-part of Ser. No. 175,155, Dec. 29, 1993, Pat. No. 5,641,648, which is a continuation-in-part of Ser. No. 53,049, Apr. 22, 1993, abandoned, which is a continuation of Ser. No. 114,618, Oct. 29, 1987, Pat. No. 5,243,038, which is a continuation-in-part of Ser. No. 927,258, Nov. 4, 1986, abandoned.

[51] Int. Cl.$^6$ .......................... A61K 38/17; A61K 38/39; C12P 21/02

[52] U.S. Cl. ......................... 530/353; 435/69.1; 530/356; 530/357

[58] Field of Search ........................... 435/69.1; 530/353, 530/356, 357

[56] References Cited

U.S. PATENT DOCUMENTS

| | | | |
|---|---|---|---|
| 4,132,746 | 1/1979 | Urry et al. | 525/432 |
| 4,187,852 | 2/1980 | Urry et al. | 600/36 |
| 4,474,851 | 10/1984 | Urry | 428/373 |
| 4,500,700 | 2/1985 | Urry | 528/328 |
| 4,589,882 | 5/1986 | Urry | 623/11 |
| 5,089,406 | 2/1992 | Williams et al. | 435/172.3 |
| 5,149,657 | 9/1992 | Maugh et al. | 435/320.1 |

FOREIGN PATENT DOCUMENTS

| | | |
|---|---|---|
| 2162190A | 1/1986 | United Kingdom . |

OTHER PUBLICATIONS

Schwartz et al. Structure of mouse type IV collagen. Eur. J. Biochemistry vol. 157 49–56, 1986.

Sandberg et al. Quantitation of elastin through measurement of its pentapeptide content. Biochem. Biophys. Res. Commun. vol. 136 672–678.

Gage et al. Internal structure of the silk fibroin gene of Bombyx mori. J. Biological Chemistry vol. 255 9444–9450, 1980.

Kempe et al., Gene (1985), 39:239–245.

Nakajima et al., (1980), 93:956345 Chemical Abstracts.

Bressan et al., Biochemistry (1987), 26:1497–1503.

Shen, Proc. Nat. Acad. Sci. USA (1984), 81:4627–4631.

Doel et al., Nucleic Acids Res. (1980), 8:4575–4592.

Hartley et al., Gene (1981), 13:347–353.

Gage et al., J. Biol. Chem. (1980), 255:9444–9450.

Gupta et al., Bio/Technology (1983), 1:602–609.

Sadler et al., Gene (1980), 8:279–300.

Jarman et al., World Biotech Rep. (1985), 1:505–512.

Dixon, Bio/Technology (1985), 3:671.

Lotz et al., J. Mol. Biol. (1982), 156:345–357.

Allbertini et al., Cell (1982), 29:319–328.

Bell et al., Int. J. Peptide Protein Res. (1974), 6:155–156.

Urry et al., Protein Elasticity of Sequential Polypeptides (1984), 3:403–436 J. Protein Chemistry.

Foster et al., "Isolation and Amino Acid Sequences of Tropoelastin Peptides", J. Biol. Chem. 1973, 248:2876–2879.

Sandberg et al., "Elastin Structure, Biosynthesis and Relation to Disease Sates", N. Engl. J. Med. (1981), 304:566–579.

Hein et al., "Construction of Genes or Gene Fragments by Use of Two Long Synthetic Oligonucleotides Representing the Coding and Noncoding Strands", Nucleosides & Nucleotides (1988), 7:497–510.

Cserpan et al., "Conversion of Single–Stranded Oligonucleotides into Cloned Duplexes and its Consecutive Application to Short Artificial Genes", Acta Chemica Scandinavica (1991), 265–272.

McClain et al., "Variants in Clones of Gene–Machine–Synthesized Oligodeoxynucleotides", Nucleic Acids Research (1986), 14:6770.

*Primary Examiner*—James Ketter
*Assistant Examiner*—John S. Brusca
*Attorney, Agent, or Firm*—Richard F. Trecartin

[57] ABSTRACT

Novel polypeptides comprising repetitive units of amino acids, as well as synthetic genes encoding the subject polypeptides are provided. The subject polypeptides are characterized by comprising repetitive units of amino acids, where the repetitive units are present in naturally occurring proteins, particularly naturally occurring structural proteins. The subject polypeptides find use in a variety of applications, such as structural components of prosthetic devices, synthetic fibers, and the like.

16 Claims, 10 Drawing Sheets

```
                                                         ┌►β-lactamase
m  t  m  i  t  p  s  l  g  c  r  s  t  l  e  d  p | h  f  r
ATGACCATGATTACGCCAAGCTTGGGCTGCAGGTCGACTCTAGAGGATCCCCATTTCCGT
                        :      :     :     :     :
                     HindIII  PstI  SalI  XbaI  BamHI
                                                 -1 +1 of mature β-lactamase
v  a  l  l  p  f  f  a  a  f  c  l  p  v  p  a  h
GTCGCCCTTATTCCCTTTTTTGCGGCATTTTGCCTTCCTGTTTTTGCTCAC...
```
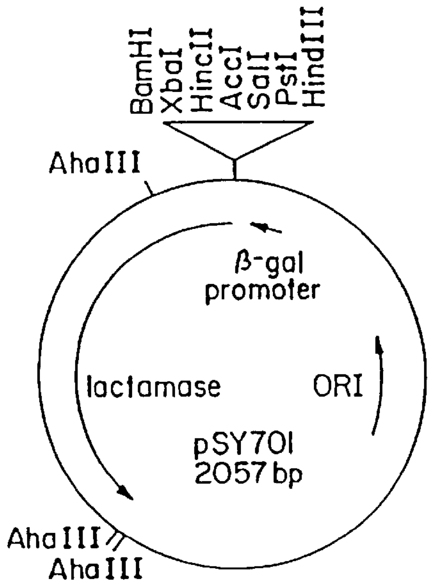
FIG._1

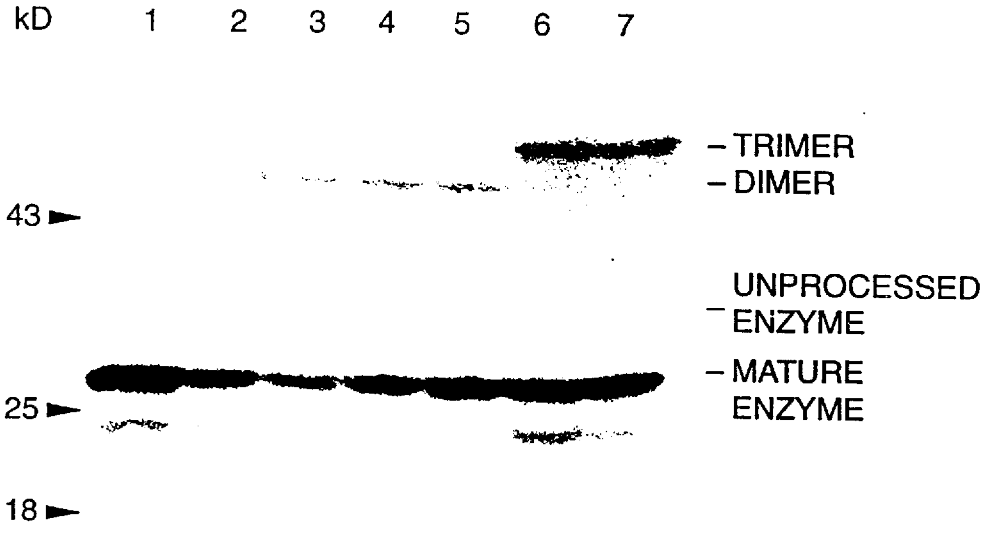
FIG._2A
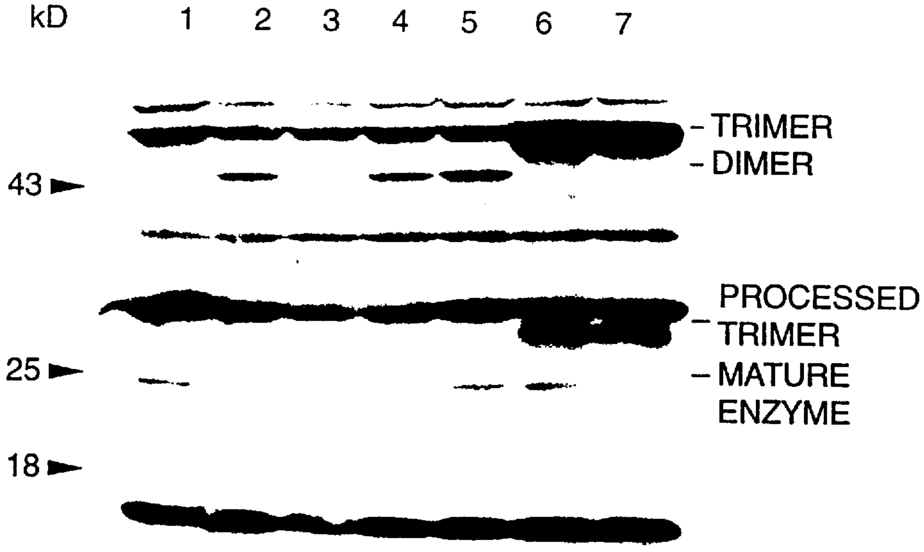
FIG._2B

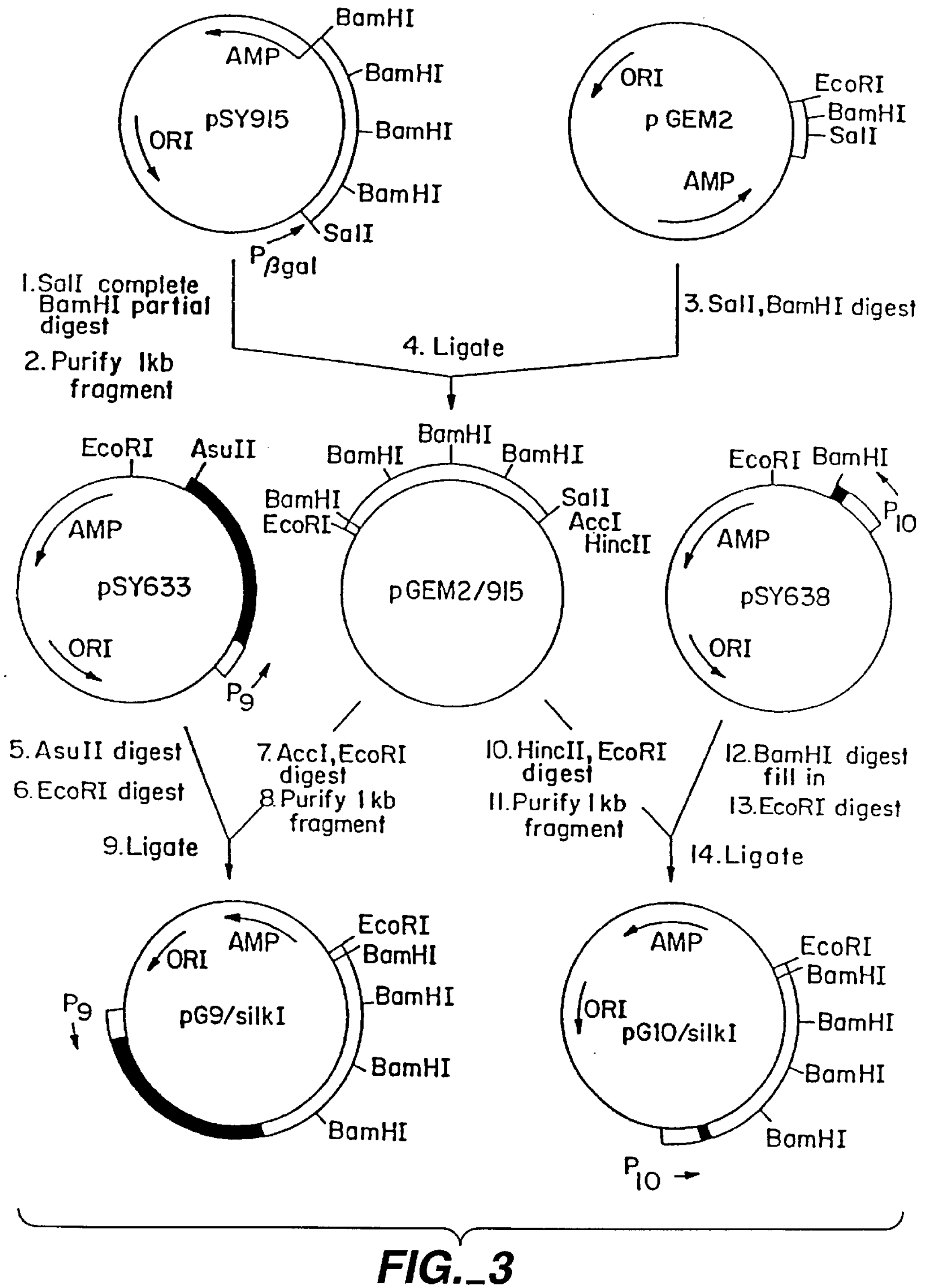
FIG._3

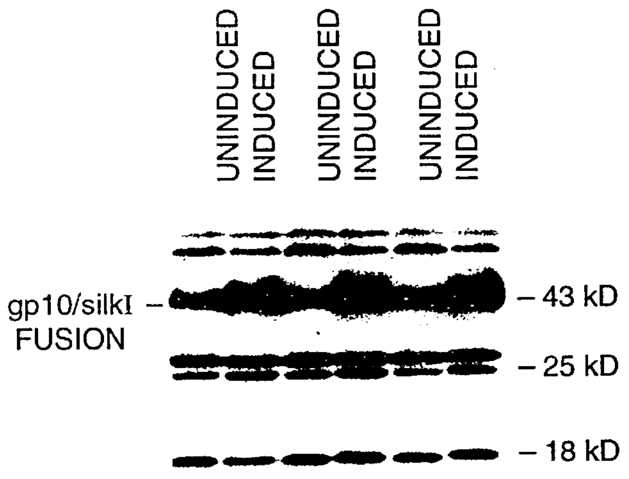
FIG._4A
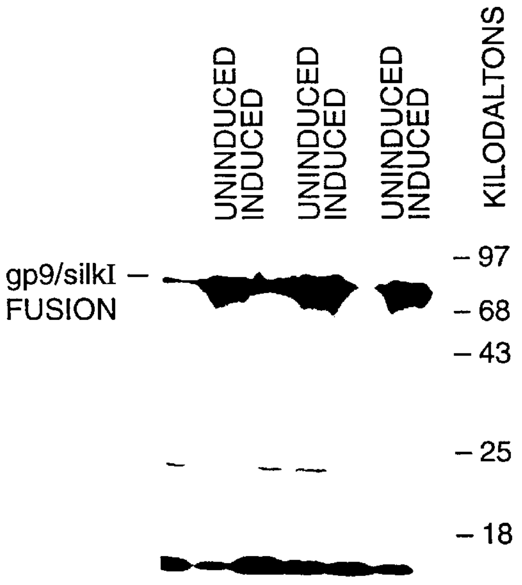
FIG._4B
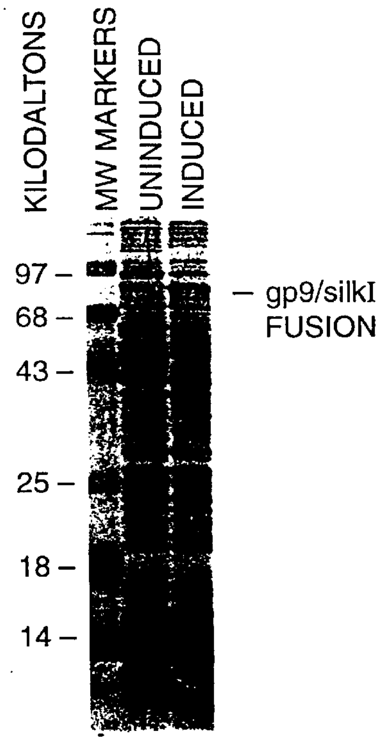
FIG._4C

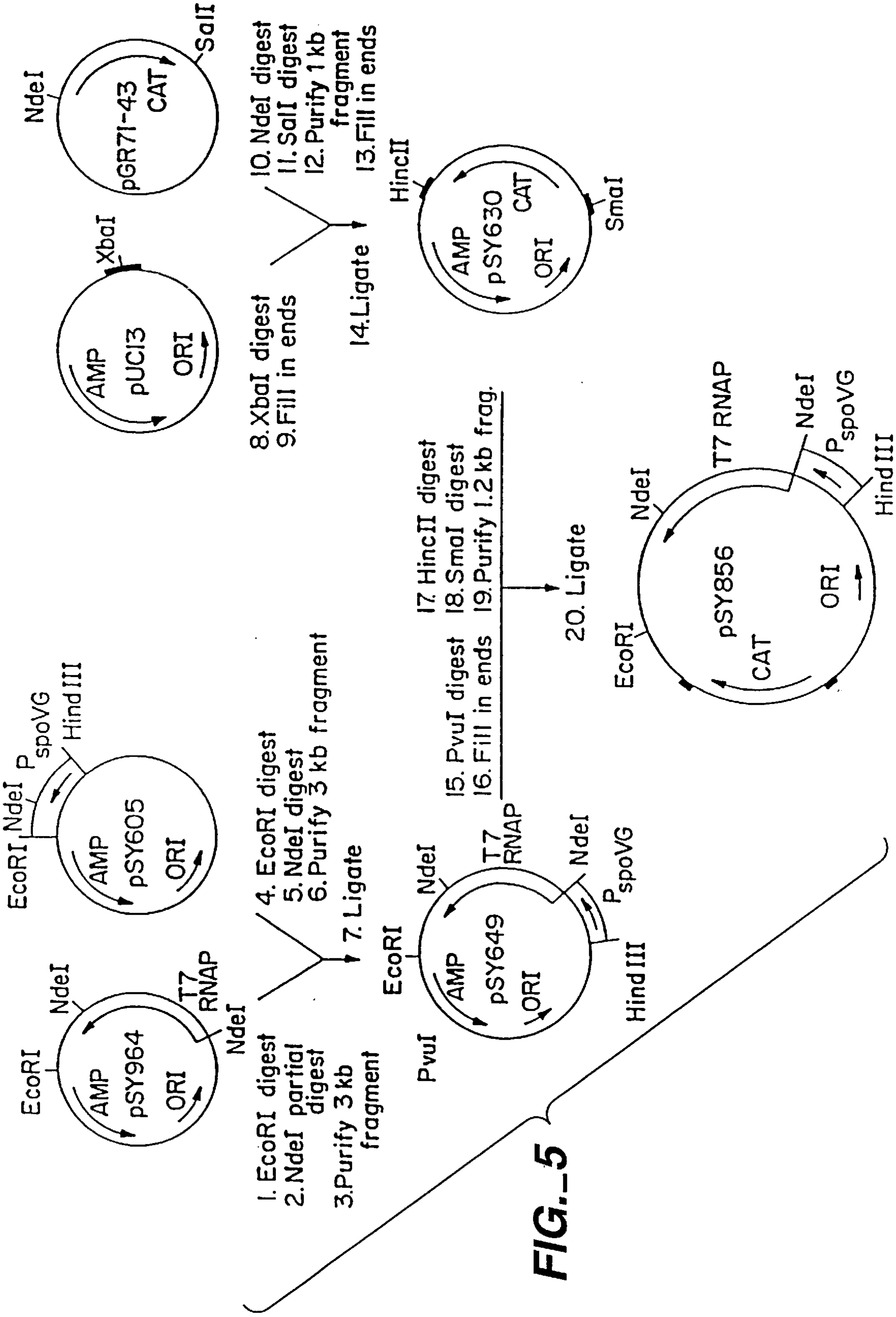
FIG._5

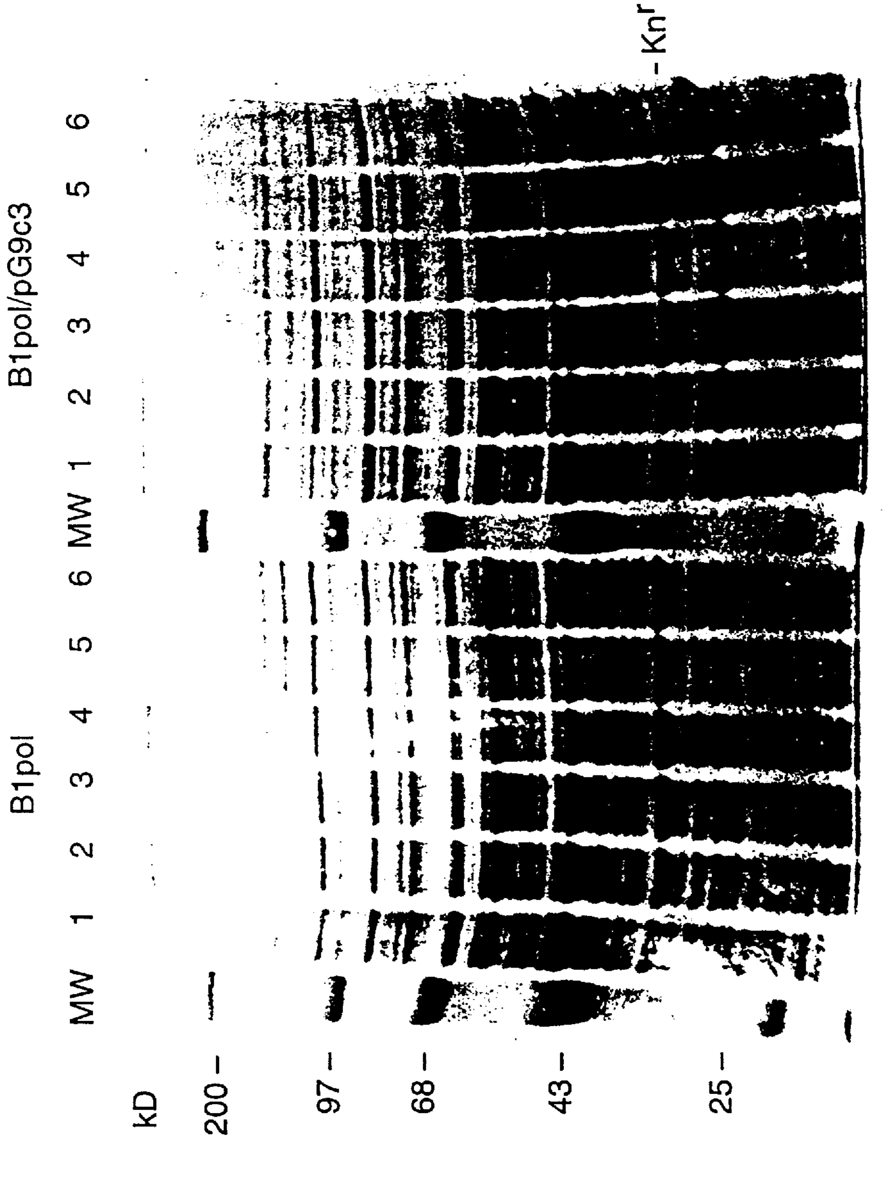
FIG._6

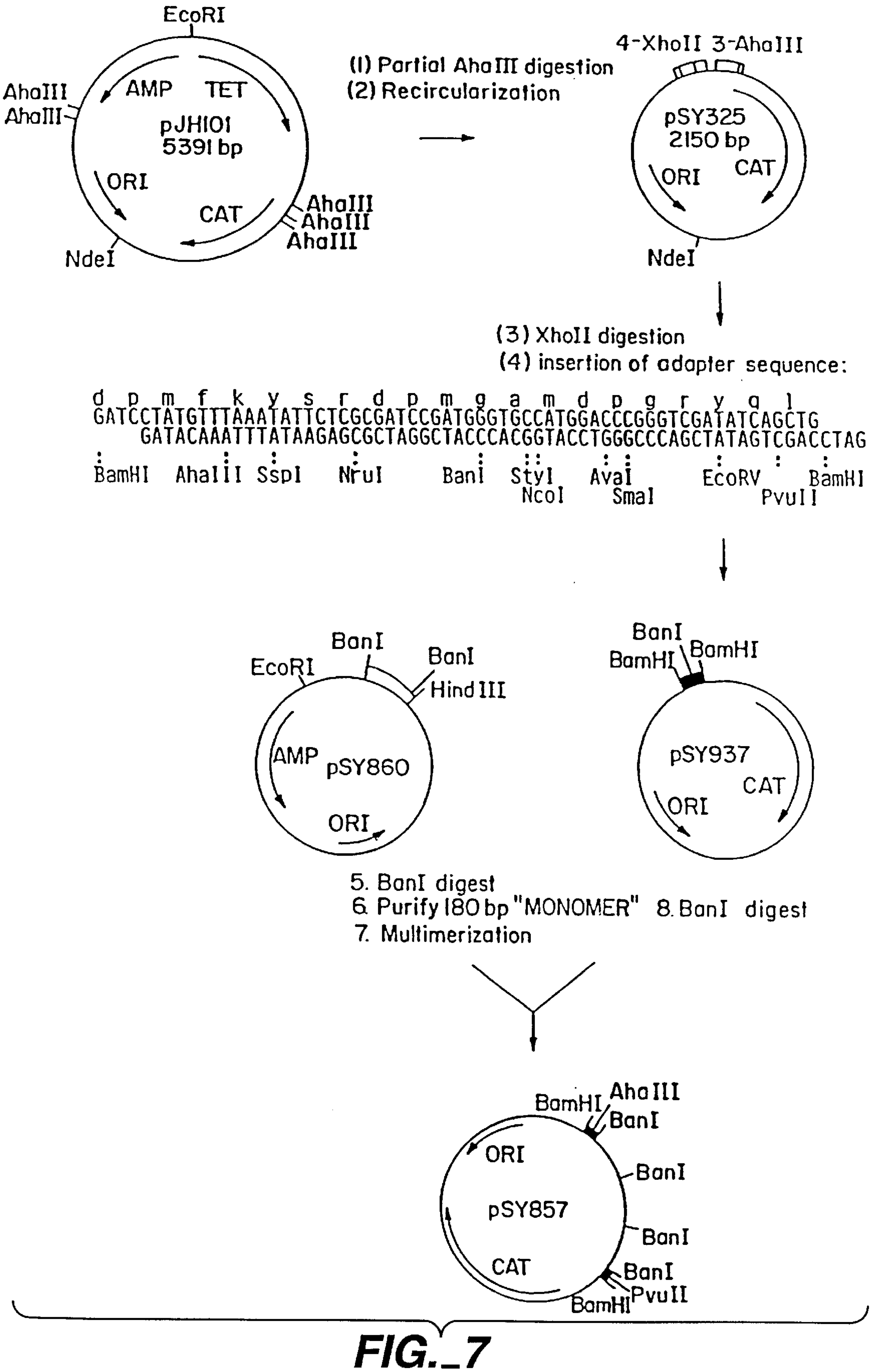
FIG._7

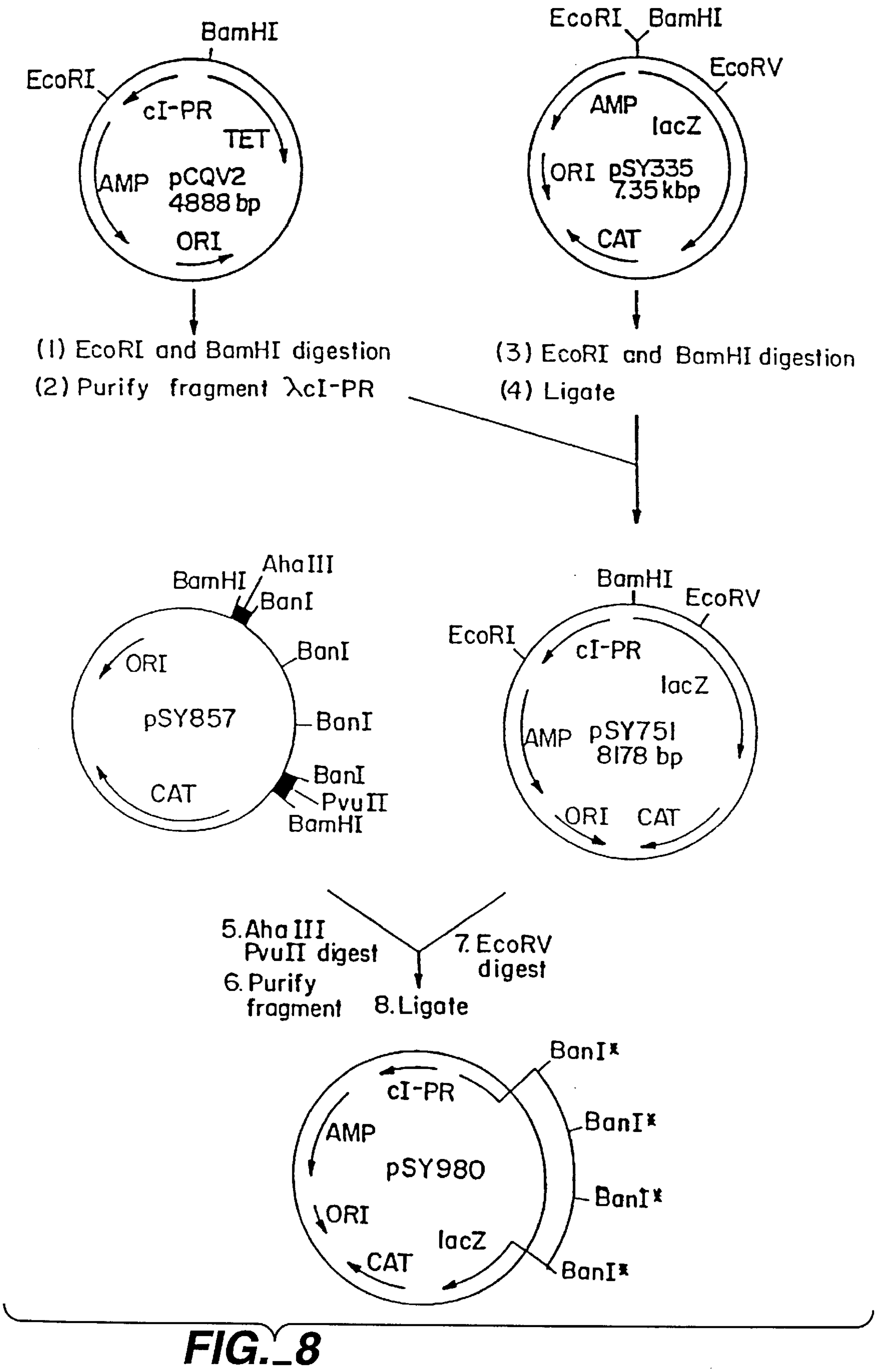
FIG._8

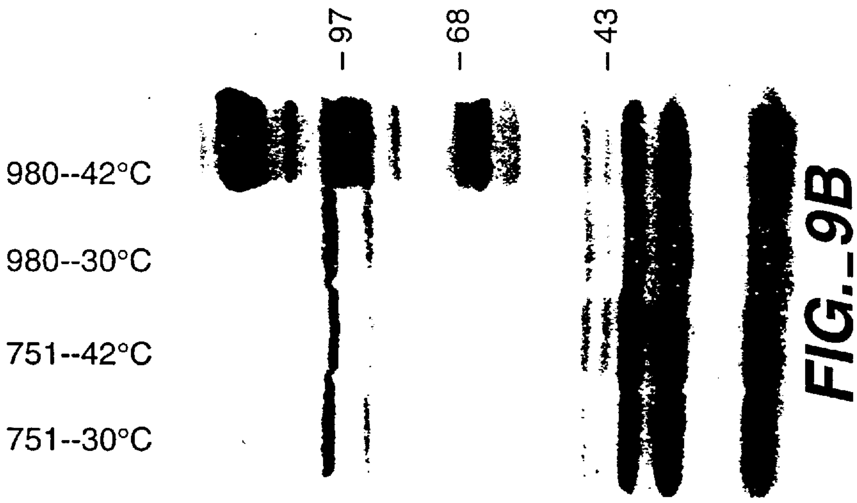
FIG._9B
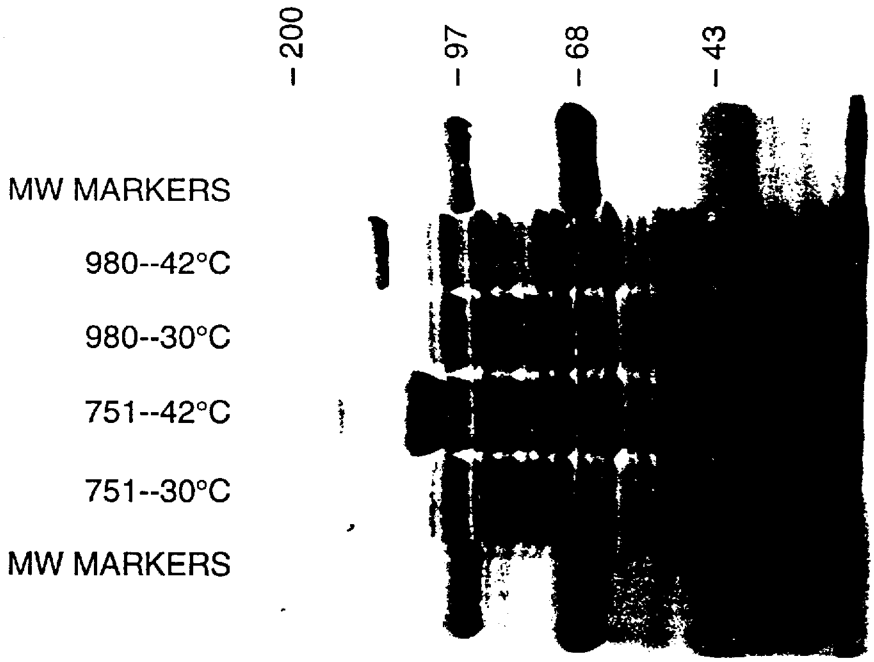
FIG._9A

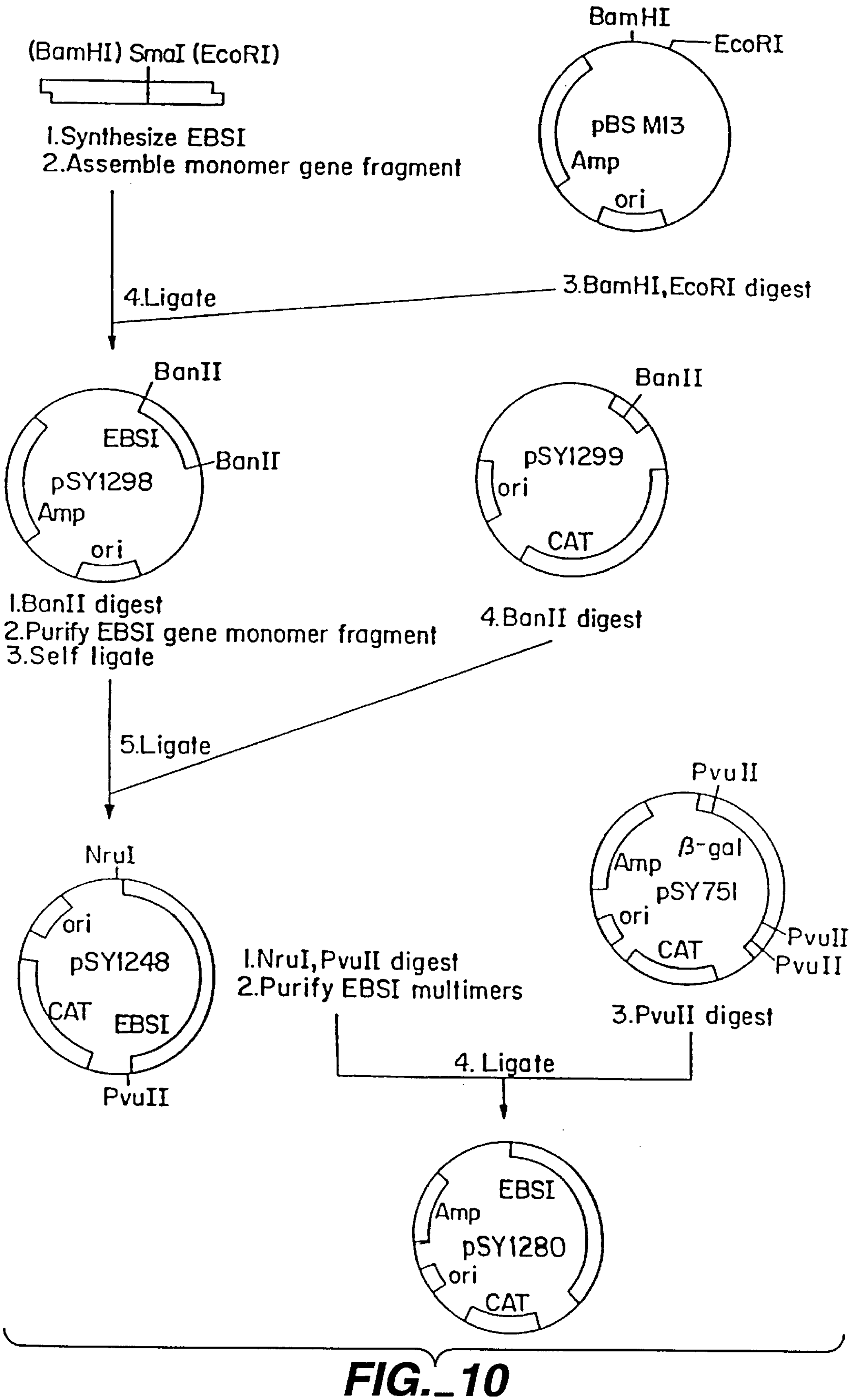
FIG._10

SEQUENCE LISTING ( 1 ) GENERAL INFORMATION:

( i i i ) NUMBER OF SEQUENCES: 112

( 2 ) INFORMATION FOR SEQ ID NO:1:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Pro Thr Thr Thr Lys
1 5

( 2 ) INFORMATION FOR SEQ ID NO:2:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Ala Lys Pro Ser Tyr Pro Pro Thr Tyr Lys
1 5 10

( 2 ) INFORMATION FOR SEQ ID NO:3:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

Pro Pro Val Tyr Lys
1 5

( 2 ) INFORMATION FOR SEQ ID NO:4:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

Thr Thr Thr Pro Asp Val
1 5

( 2 ) INFORMATION FOR SEQ ID NO:5:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

Gly Gly Leu Gly Tyr
1 5

( 2 ) INFORMATION FOR SEQ ID NO:6:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:6:

Ala Pro Ala Ala Pro
1 5

( 2 ) INFORMATION FOR SEQ ID NO:7:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

Pro Glu Pro Lys
1

( 2 ) INFORMATION FOR SEQ ID NO:8:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

Pro Met Pro Lys
1

( 2 ) INFORMATION FOR SEQ ID NO:9:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

Ser Pro Pro Pro Pro
1 5

( 2 ) INFORMATION FOR SEQ ID NO:10:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:10:

Pro Glu Pro Met Pro Lys
1 5

( 2 ) INFORMATION FOR SEQ ID NO:11:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:11:

Pro Pro Val Tyr Lys Pro Pro Val Gln Lys
1 5 10

( 2 ) INFORMATION FOR SEQ ID NO:12:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

Pro Pro Val Lys
1

( 2 ) INFORMATION FOR SEQ ID NO:13:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:13:

Pro Pro Val Glu Lys
1 5

( 2 ) INFORMATION FOR SEQ ID NO:14:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

Pro Gly Val Gly Val
1 5

( 2 ) INFORMATION FOR SEQ ID NO:15:

( i ) SEQUENCE CHARACTERISTICS:
( A ) LENGTH: 6 amino acids
( B ) TYPE: amino acid
( C ) STRANDEDNESS: single
( D ) TOPOLOGY: linear -continued ( i i ) MOLECULE TYPE: peptide ( x i ) SEQUENCE DESCRIPTION: SEQ ID NO:15:

Val Gly Val Ala Pro Gly
1 5

( 2 ) INFORMATION FOR SEQ ID NO:16:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:16:

Ser Pro Pro Pro Pro Ser Pro Lys Tyr Val Tyr Lys
1 5 10

( 2 ) INFORMATION FOR SEQ ID NO:17:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:17:

Ser Pro Pro Pro Pro Tyr Tyr Tyr Lys Ser Pro Pro Pro Pro Ser Pro
1 5 10 15

( 2 ) INFORMATION FOR SEQ ID NO:18:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:18:

Ser Pro Pro Pro Pro Pro Thr Pro Ser Tyr Gly His Pro Lys Thr Pro
1 5 10 15

( 2 ) INFORMATION FOR SEQ ID NO:19:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:19:

Ser Ser Pro Pro Pro Pro Ser Pro Ser Pro Pro Pro Pro Thr Tyr Tyr
1 5 10 15

Tyr ( 2 ) INFORMATION FOR SEQ ID NO:20:

( i ) SEQUENCE CHARACTERISTICS:
( A ) LENGTH: 13 amino acids
( B ) TYPE: amino acid
( C ) STRANDEDNESS: single (D) TOPOLOGY: linear (ii) MOLECULE TYPE: peptide (xi) SEQUENCE DESCRIPTION: SEQ ID NO:20:

Lys Ser Pro Val Pro Lys Ser Pro Val Glu Glu Lys Gly
1 5 10

(2) INFORMATION FOR SEQ ID NO:21:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:21:

Ser Gly Ala Gly Ala Gly
1 5

(2) INFORMATION FOR SEQ ID NO:22:

(i) SEQUENCE CHARACTERISTICS:
(A) LENGTH: 59 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:22:

Gly Ala Gly Ala Gly Ser Gly Ala Gly Ala Gly Ser Gly Ala Gly Ala
1 5 10 15

Gly Ser Gly Ala Gly Ala Gly Ser Gly Ala Gly Ala Gly Ser Gly Ala
20 25 30

Gly Ala Gly Ser Gly Ala Gly Ala Gly Ser Gly Ala Gly Ala Gly Ser
35 40 45

Gly Ala Gly Ala Gly Ser Gly Ala Ala Gly Tyr
50 55

(2) INFORMATION FOR SEQ ID NO:23:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:23:

Gly Val Gly Val Pro
1 5

(2) INFORMATION FOR SEQ ID NO:24:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:24:

Val Pro Gly Val Gly 1 5

( 2 ) INFORMATION FOR SEQ ID NO:25:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:25:

Ala Pro Gly Val Gly Val
1 5

( 2 ) INFORMATION FOR SEQ ID NO:26:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:26:

Arg Glu Asp Val
1

( 2 ) INFORMATION FOR SEQ ID NO:27:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:27:

Tyr Ile Gly Ser Arg
1 5

( 2 ) INFORMATION FOR SEQ ID NO:28:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:28:

Gly Ala Gly Cys
1

( 2 ) INFORMATION FOR SEQ ID NO:29:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:29:

Gly Cys Cys Val

1

( 2 ) INFORMATION FOR SEQ ID NO:30:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:30:

Val Ser Pro Asp
1

( 2 ) INFORMATION FOR SEQ ID NO:31:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:31:

Val Cys Asp Pro
1

( 2 ) INFORMATION FOR SEQ ID NO:32:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:32:

Asp Pro Gly Lys
1

( 2 ) INFORMATION FOR SEQ ID NO:33:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:33:

Asp Pro Gly Lys Gly Xaa Tyr
1 5

( 2 ) INFORMATION FOR SEQ ID NO:34:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:34:

Glu Pro Gly Tyr Ile Gly Ser Arg Cys Asp Ala Gly Tyr 1 5 10

( 2 ) INFORMATION FOR SEQ ID NO:35:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:35:

Pro Lys Gly Asp Arg Gly Asp Ala Gly Pro Lys
1 5 10

( 2 ) INFORMATION FOR SEQ ID NO:36:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:36:

Ala Val Thr Gly Arg Gly Asp Ser Pro Ala Ser
1 5 10

( 2 ) INFORMATION FOR SEQ ID NO:37:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:37:

Gly Arg Gly Gly Ser Phe Gly Gly Ser Ser Tyr Gly Gly Gly Ser
1 5 10 15

( 2 ) INFORMATION FOR SEQ ID NO:38:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:38:

Gly Ala Gly Cys Gly Asp Pro Gly Lys Gly Cys Cys Val Ala
1 5 10

( 2 ) INFORMATION FOR SEQ ID NO:39:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:39:

Val Cys Asp Arg Gly Tyr Ile Gly Ser Arg Cys Asp

-continued 1 5 10

( 2 ) INFORMATION FOR SEQ ID NO:40:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:40:

Pro Lys Gly Asp Arg Ala Asp Ala Gly Pro Lys
1 5 10

( 2 ) INFORMATION FOR SEQ ID NO:41:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:41:

Gly Ala Gly Ala Gly Ser
1 5

( 2 ) INFORMATION FOR SEQ ID NO:42:

( i ) SEQUENCE CHARACTERISTICS:
( A ) LENGTH: 53 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:42:

Gly Ala Gly Ala Gly Ser Gly Ala Gly Ala Gly Ser Gly Ala Gly Ala
1 5 10 15

Gly Ser Gly Ala Gly Ala Gly Ser Gly Ala Gly Ala Gly Ser Gly Ala
20 25 30

Gly Ala Gly Ser Gly Ala Gly Ala Gly Ser Gly Ala Gly Ala Gly Ser
35 40 45

Gly Ala Ala Gly Tyr
50

( 2 ) INFORMATION FOR SEQ ID NO:43:

( i ) SEQUENCE CHARACTERISTICS:
( A ) LENGTH: 40 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:43:

Val Pro Gly Val Gly Val Pro Gly Val Gly Val Pro Gly Val Gly Val
1 5 10 15

Pro Gly Val Gly Val Pro Gly Val Gly Val Pro Gly Val Gly Val Pro
20 25 30

Gly Val Gly Val Pro Gly Val Gly
35 40

( 2 ) INFORMATION FOR SEQ ID NO:44:

( i ) SEQUENCE CHARACTERISTICS:
( A ) LENGTH: 26 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:44:

Tyr Thr Ile Thr Val Tyr Ala Val Thr Gly Arg Gly Asp Ser Pro Ala
1 5 10 15

Ser Ser Lys Pro Ile Ser Ile Asn Tyr Cys
20 25

( 2 ) INFORMATION FOR SEQ ID NO:45:

( i ) SEQUENCE CHARACTERISTICS:
( A ) LENGTH: 33 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:45:

Gly Ala Pro Gly Ala Pro Gly Ser Gln Gly Ala Pro Gly Leu Gln Gly
1 5 10 15

Ala Pro Gly Ala Pro Gly Ser Gln Gly Ala Pro Gly Leu Gln Tyr Met
20 25 30

Lys ( 2 ) INFORMATION FOR SEQ ID NO:46:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:46:

GGTGCGGGCG CAGGAAGT 18

( 2 ) INFORMATION FOR SEQ ID NO:47:

( i ) SEQUENCE CHARACTERISTICS:
( A ) LENGTH: 18 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:47:

ACCACTTCCT GCGCCCGC 18

( 2 ) INFORMATION FOR SEQ ID NO:48:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:48:

Ala Gly Ala Gly Ser Gly
1 5

( 2 ) INFORMATION FOR SEQ ID NO:49:

( i ) SEQUENCE CHARACTERISTICS:
( A ) LENGTH: 290 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:49:

AAGCTTGGGC TGCAGGTCAC CCGGGCGGGC GCAGGAAGTG GTGCGGGCGC AGGAAGTGGT 60

GCGGGCGCAG GAAGTGGTGC GGGCGCAGGA AGTGGTGCGG GCGCAGGAAG TGGTGCGGGC 120

GCAGGAAGTG GTGCGGGCGC AGGAAGTGGT GCGGGCGCAG GAAGTGGTGC GGGCGCAGGA 180

AGTGGTGCGG GCGCAGGAAG TGGTGCGGGC GCAGGAAGTG GTGCGGGCGC AGGAAGTGGT 240

GCGGGCGCAG GAAGTGGGAC TCTAGAGGAT CCCCGGGCGA GCTCGAATTC 290

( 2 ) INFORMATION FOR SEQ ID NO:50:

( i ) SEQUENCE CHARACTERISTICS:
( A ) LENGTH: 97 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:50:

Lys Leu Gly Leu Gln Val Thr Arg Ala Gly Ala Gly Ser Gly Ala Gly
1 5 10 15

Ala Gly Ser Gly Ala Gly Ala Gly Ser Gly Ala Gly Ala Gly Ser Gly
20 25 30

Ala Gly Ala Gly Ser Gly Ala Gly Ala Gly Ser Gly Ala Gly Ala Gly
35 40 45

Ser Gly Ala Gly Ala Gly Ser Gly Ala Gly Ala Gly Ser Gly Ala Gly
50 55 60

Ala Gly Ser Gly Ala Gly Ala Gly Ser Gly Ala Gly Ala Gly Ser Gly
65 70 75 80

Ala Gly Ala Gly Ser Gly Thr Leu Glu Asp Pro Arg Ala Ser Ser Asn
85 90 95

Ser ( 2 ) INFORMATION FOR SEQ ID NO:51:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:51:

Met Thr Met Ile Thr Pro Ser Leu Gly Cys Arg Ser Thr Leu Glu Asp
1 5 10 15

Pro His Phe Arg Val Ala Leu Ile Pro Phe Phe Ala Ala Phe Cys Leu 20 25 30

Pro Val Phe Ala His
35

(2) INFORMATION FOR SEQ ID NO:52:

(i) SEQUENCE CHARACTERISTICS:
(A) LENGTH: 84 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:52:

Arg Ala Gly Ala Gly Ser Gly Ala Gly Ala Gly Ser Gly Ala Gly Ala
1 5 10 15

Gly Ser Gly Ala Gly Ala Gly Ser Gly Ala Gly Ala Gly Ser Gly Ala
20 25 30

Gly Ala Gly Ser Gly Ala Gly Ala Gly Ser Gly Ala Gly Ala Gly Ser
35 40 45

Gly Ala Gly Ala Gly Ser Gly Ala Gly Ala Gly Ser Gly Ala Gly Ala
50 55 60

Gly Ser Gly Ala Gly Ala Gly Ser Gly Ala Gly Ala Gly Ser Gly Thr
65 70 75 80

Leu Glu Asp Pro (2) INFORMATION FOR SEQ ID NO:53:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:53:

Thr Ala Ala Ala Thr Gly
1 5

(2) INFORMATION FOR SEQ ID NO:54:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:54:

Cys Ala Thr Ala Thr Gly
1 5

(2) INFORMATION FOR SEQ ID NO:55:

(i) SEQUENCE CHARACTERISTICS:
(A) LENGTH: 61 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:55:

```
GGTGCCGGCA  GCGGTGCAGG  AGCCGGTTCT  GGAGCTGGCG  CGGGCTCTGG  CGCGGGCGCA         60

G                                                                               61
```

( 2 ) INFORMATION FOR SEQ ID NO:56:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:56:

```
GATCCTGCGC  CCGCGCCAGA  GCCCGCGCCA  GCTCCAGAAC  CGGCTCCTGC  ACCGCTGCCG         60

GCACC                                                                           65
```

( 2 ) INFORMATION FOR SEQ ID NO:57:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:57:

```
Gly  Ala  Gly  Ser  Gly  Ala  Gly  Ala  Gly  Ser  Gly  Ala  Gly  Ala  Gly  Ser
 1                   5                            10                       15

Gly  Ala  Gly  Ala  Gly  Ser
                20
```

( 2 ) INFORMATION FOR SEQ ID NO:58:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:58:

```
GATCCGGCGC  AGGCGCTGGT  TCTGGCGCAG  GGGCAGGCTC  TGGCGCAGGA  GCGGGGTCTG         60

GAGCTGCA                                                                        68
```

( 2 ) INFORMATION FOR SEQ ID NO:59:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:59:

```
GCTCCAGACC  CCGCTCCTGC  GCCAGAGCCT  GCCCCTGCGC  CAGAACCAGC  GCCTGCGCCG         60
```

( 2 ) INFORMATION FOR SEQ ID NO:60:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:60:

Gly Ser Gly Ala Gly Ala Gly Ser Gly Ala Gly Ala Gly Ser Gly Ala
1 5 10 15

Gly Ala Gly Ser Gly Ala Ala
20

( 2 ) INFORMATION FOR SEQ ID NO:61:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:61:

GGCTATGGAG CTGGCGCTGG CTCAGGTGCT GGAGCAGGAA GCGGAGCGGG TGCCA 55

( 2 ) INFORMATION FOR SEQ ID NO:62:

( i ) SEQUENCE CHARACTERISTICS:
( A ) LENGTH: 69 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:62:

AGCTTGGCAC CCGCTCCGCT TCCTGCTCCA GCACCTGAGC CAGCGCCAGC GCCAGCTCCA 60

TAGCCTGCA 69

( 2 ) INFORMATION FOR SEQ ID NO:63:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:63:

Ala Gly Tyr Gly Ala Gly Ala Gly Ser Gly Ala Gly Ala Gly Ser Gly
1 5 10 15

Ala Gly Ala ( 2 ) INFORMATION FOR SEQ ID NO:64:

( i ) SEQUENCE CHARACTERISTICS:
( A ) LENGTH: 1177 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:64:

Asp Pro Val Val Leu Gln Arg Arg Asp Trp Glu Asn Pro Gly Val Thr
1 5 10 15

Gln Leu Asn Arg Leu Ala Ala His Pro Pro Phe Ala Ser Asp Pro Met
20 25 30

-continued

Gly Ala Gly Ser Gly Ala Gly Ala Gly Ser Gly Ala Gly Ala Gly Ser
35 40 45

Gly Ala Gly Ala Gly Ser Gly Ala Gly Ala Gly Ser Gly Ala Gly Ala
50 55 60

Gly Ser Gly Ala Gly Ala Gly Ser Gly Ala Ala Gly Tyr Gly Ala Gly
65 70 75 80

Ala Gly Ser Gly Ala Gly Ala Gly Ser Gly Ala Gly Ala Gly Ser Gly
85 90 95

Ala Gly Ala Gly Ser Gly Ala Gly Ala Gly Ser Gly Ala Gly Ala Gly
100 105 110

Ser Gly Ala Gly Ala Gly Ser Gly Ala Gly Ala Gly Ser Gly Ala Gly
115 120 125

Ala Gly Ser Gly Ala Ala Gly Tyr Gly Ala Gly Ala Gly Ser Gly Ala
130 135 140

Gly Ala Gly Ser Gly Ala Gly Ala Gly Ser Gly Ala Gly Ala Gly Ser
145 150 155 160

Gly Ala Gly Ala Gly Ser Gly Ala Gly Ala Gly Ser Gly Ala Gly Ala
165 170 175

Gly Ser Gly Ala Gly Ala Gly Ser Gly Ala Gly Ala Gly Ser Gly Ala
180 185 190

Ala Gly Tyr Gly Ala Gly Ala Gly Ser Gly Ala Gly Ala Gly Ser Gly
195 200 205

Ala Gly Ala Gly Ser Gly Ala Gly Ala Gly Ser Gly Ala Gly Ala Gly
210 215 220

Ser Gly Ala Gly Ala Gly Ser Gly Ala Gly Ala Gly Ser Gly Ala Gly
225 230 235 240

Ala Gly Ser Gly Ala Gly Ala Gly Ser Gly Ala Ala Gly Tyr Gly Ala
245 250 255

Gly Ala Gly Ser Gly Ala Gly Ala Gly Ser Gly Ala Gly Ala Gly Ser
260 265 270

Gly Ala Gly Ala Gly Ser Gly Ala Gly Ala Gly Ser Gly Ala Gly Ala
275 280 285

Gly Ser Gly Ala Gly Ala Gly Ser Gly Ala Gly Ala Gly Ser Gly Ala
290 295 300

Gly Ala Gly Ser Gly Ala Ala Gly Tyr Gly Ala Gly Ala Gly Ser Gly
305 310 315 320

Ala Gly Ala Gly Ser Gly Ala Gly Ala Gly Ser Gly Ala Gly Ala Gly
325 330 335

Ser Gly Ala Gly Ala Gly Ser Gly Ala Gly Ala Gly Ser Gly Ala Gly
340 345 350

Ala Gly Ser Gly Ala Gly Ala Gly Ser Gly Ala Gly Ala Gly Ser Gly
355 360 365

Ala Ala Gly Tyr Gly Ala Gly Ala Gly Ser Gly Ala Gly Ala Gly Ser
370 375 380

Gly Ala Gly Ala Gly Ser Gly Ala Gly Ala Gly Ser Gly Ala Gly Ala
385 390 395 400

Gly Ser Gly Ala Gly Ala Gly Ser Gly Ala Gly Ala Gly Ser Gly Ala
405 410 415

Gly Ala Gly Ser Gly Ala Gly Ala Gly Ser Gly Ala Ala Gly Tyr Gly
420 425 430

Ala Gly Ala Gly Ser Gly Ala Gly Ala Gly Ser Gly Ala Gly Ala Gly
435 440 445

Ser Gly Ala Gly Ala Gly Ser Gly Ala Gly Ala Gly Ser Gly Ala Gly
450 455 460

-continued

Ala Gly Ser Gly Ala Gly Ala Gly Ser Gly Ala Gly Ala Gly Ser Gly
465 470 475 480

Ala Gly Ala Gly Ser Gly Ala Ala Gly Tyr Gly Ala Gly Ala Gly Ser
485 490 495

Gly Ala Gly Ala Gly Ser Gly Ala Gly Ala Gly Ser Gly Ala Gly Ala
500 505 510

Gly Ser Gly Ala Gly Ala Gly Ser Gly Ala Gly Ala Gly Ser Gly Ala
515 520 525

Gly Ala Gly Ser Gly Ala Gly Ala Gly Ser Gly Ala Gly Ala Gly Ser
530 535 540

Gly Ala Ala Gly Tyr Gly Ala Gly Ala Gly Ser Gly Ala Gly Ala Gly
545 550 555 560

Ser Gly Ala Gly Ala Gly Ser Gly Ala Gly Ala Gly Ser Gly Ala Gly
565 570 575

Ala Gly Ser Gly Ala Gly Ala Gly Ser Gly Ala Gly Ala Gly Ser Gly
580 585 590

Ala Gly Ala Gly Ser Gly Ala Gly Ala Gly Ser Gly Ala Ala Gly Tyr
595 600 605

Gly Ala Gly Ala Gly Ser Gly Ala Gly Ala Gly Ser Gly Ala Gly Ala
610 615 620

Gly Ser Gly Ala Gly Ala Gly Ser Gly Ala Gly Ala Gly Ser Gly Ala
625 630 635 640

Gly Ala Gly Ser Gly Ala Gly Ala Gly Ser Gly Ala Gly Ala Gly Ser
645 650 655

Gly Ala Gly Ala Gly Ser Gly Ala Ala Gly Tyr Gly Ala Gly Ala Gly
660 665 670

Ser Gly Ala Gly Ala Gly Ser Gly Ala Gly Ala Gly Ser Gly Ala Gly
675 680 685

Ala Gly Ser Gly Ala Gly Ala Gly Ser Gly Ala Gly Ala Gly Ser Gly
690 695 700

Ala Gly Ala Gly Ser Gly Ala Gly Ala Gly Ser Gly Ala Gly Ala Gly
705 710 715 720

Ser Gly Ala Ala Gly Tyr Gly Ala Gly Ala Gly Ser Gly Ala Gly Ala
725 730 735

Gly Ser Gly Ala Gly Ala Gly Ser Gly Ala Gly Ala Gly Ser Gly Ala
740 745 750

Gly Ala Gly Ser Gly Ala Gly Ala Gly Ser Gly Ala Gly Ala Gly Ser
755 760 765

Gly Ala Gly Ala Gly Ser Gly Ala Gly Ala Gly Ser Gly Ala Ala Gly
770 775 780

Tyr Gly Ala Gly Ala Gly Ser Gly Ala Gly Ala Gly Ser Gly Ala Gly
785 790 795 800

Ala Gly Ser Gly Ala Gly Ala Gly Ser Gly Ala Gly Ala Gly Ser Gly
805 810 815

Ala Gly Ala Gly Ser Gly Ala Gly Ala Gly Ser Gly Ala Gly Ala Gly
820 825 830

Ser Gly Ala Gly Ala Gly Ser Gly Ala Ala Gly Tyr Gly Ala Gly Ala
835 840 845

Gly Ser Gly Ala Gly Ala Gly Ser Gly Ala Gly Ala Gly Ser Gly Ala
850 855 860

Gly Ala Gly Ser Gly Ala Gly Ala Gly Ser Gly Ala Gly Ala Gly Ser
865 870 875 880

Gly Ala Gly Ala Gly Ser Gly Ala Gly Ala Gly Ser Gly Ala Gly Ala

-continued

```
                        885                                     890                                     895

Gly Ser Gly Ala Ala Gly Tyr Gly Ala Gly Ala Gly Ser Gly Ala Gly
                900                                     905                                     910

Ala Gly Ser Gly Ala Gly Ala Gly Ser Gly Ala Gly Ala Gly Ser Gly
            915                                     920                                     925

Ala Gly Ala Gly Ser Gly Ala Gly Ala Gly Ser Gly Ala Gly Ala Gly
        930                                     935                                     940

Ser Gly Ala Gly Ala Gly Ser Gly Ala Gly Ala Gly Ser Gly Ala Ala
945                                     950                                     955                                     960

Gly Tyr Gly Ala Gly Ala Gly Ser Gly Ala Gly Ala Gly Ser Gly Ala
                        965                                     970                                     975

Gly Ala Gly Ser Gly Ala Gly Ala Gly Ser Gly Ala Gly Ala Gly Ser
                980                                     985                                     990

Gly Ala Gly Ala Gly Ser Gly Ala Gly Ala Gly Ser Gly Ala Gly Ala
            995                                     1000                                    1005

Gly Ser Gly Ala Gly Ala Gly Ser Gly Ala Ala Gly Tyr Gly Ala Gly
        1010                                    1015                                    1020

Ala Gly Ser Gly Ala Gly Ala Gly Ser Gly Ala Gly Ala Gly Ser Gly
1025                                    1030                                    1035                                    1040

Ala Gly Ala Gly Ser Gly Ala Gly Ala Gly Ser Gly Ala Gly Ala Gly
                        1045                                    1050                                    1055

Ser Gly Ala Gly Ala Gly Ser Gly Ala Gly Ala Gly Ser Gly Ala Gly
                1060                                    1065                                    1070

Ala Gly Ser Gly Ala Ala Gly Tyr Gly Ala Gly Ala Gly Ser Gly Ala
            1075                                    1080                                    1085

Gly Ala Gly Ser Gly Ala Gly Ala Gly Ser Gly Ala Gly Ala Gly Ser
        1090                                    1095                                    1100

Gly Ala Gly Ala Gly Ser Gly Ala Gly Ala Gly Ser Gly Ala Gly Ala
1105                                    1110                                    1115                                    1120

Gly Ser Gly Ala Gly Ala Gly Ser Gly Ala Gly Ala Gly Ser Gly Ala
                        1125                                    1130                                    1135

Ala Gly Tyr Gly Ala Gly Ala Gly Ser Gly Ala Gly Ala Gly Ser Gly
                1140                                    1145                                    1150

Ala Gly Ala Met Asp Pro Gly Arg Tyr Gln Leu Ser Ala Gly Arg Tyr
            1155                                    1160                                    1165

His Tyr Gln Leu Val Trp Cys Gln Lys
        1170                                    1175
```

( 2 ) INFORMATION FOR SEQ ID NO:65:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:65:

AGCTGGGCTC TGGAGTAGGC CTG 23

( 2 ) INFORMATION FOR SEQ ID NO:66:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:66:

AATTCAGGCC TACTCCAGAG CCC 23

( 2 ) INFORMATION FOR SEQ ID NO:67:

( i ) SEQUENCE CHARACTERISTICS:
( A ) LENGTH: 85 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:67:

AGCTTGGTGC CAGGTGTAGG AGTTCCGGGT GTAGGCGTTC CGGGAGTTGG TGTACCTGGA 60

GTGGGTGTTC CAGGCGTAGG TGTGC 85

( 2 ) INFORMATION FOR SEQ ID NO:68:

( i ) SEQUENCE CHARACTERISTICS:
( A ) LENGTH: 85 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:68:

CCGGGCACAC CTACGCCTGG AACACCCACT CCAGGTACAC CAACTCCCGG AACGCCTACA 60

CCCGGAACTC CTACACCTGG CACCA 85

( 2 ) INFORMATION FOR SEQ ID NO:69:

( i ) SEQUENCE CHARACTERISTICS:
( A ) LENGTH: 83 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:69:

CCGGGGTAGG AGTACCAGGG GTAGGCGTCC CTGGAGCGGG TGCTGGTAGC GGCGCAGGCG 60

CGGGCTCCGG AGTAGGGGTG CCG 83

( 2 ) INFORMATION FOR SEQ ID NO:70:

( i ) SEQUENCE CHARACTERISTICS:
( A ) LENGTH: 83 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:70:

AATTCGGCAC CCCTACTCCG GAGCCCGCGC CTGCGCCGCT ACCAGCACCC GCTCCAGGGA 60

CGCCTACCCC TGGTACTCCT ACC 83

( 2 ) INFORMATION FOR SEQ ID NO:71:

( i ) SEQUENCE CHARACTERISTICS:
( A ) LENGTH: 187 base pairs
( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:71:

AGCTGGGCTC TGGAGTAGGT GTGCCAGGTG TAGGAGTTCC GGGTGTAGGC GTTCCGGGAG 60

TTGGTGTACC TGGAGTGGGT GTTCCAGGCG TAGGTGTGCC CGGGGTAGGA GTACCAGGGG 120

TAGGCGTCCC TGGAGCGGGT GCTGGTAGCG GCGCAGGCGC GGGCTCCGGA GTAGGGGTGC 180

CGAATTC 187

( 2 ) INFORMATION FOR SEQ ID NO:72:

( i ) SEQUENCE CHARACTERISTICS:
( A ) LENGTH: 75 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:72:

GATCCTATGT TTAAATATTC TCGCGAACGT TTTTGTATGG GCTCGATGTG TTACCGTGCG 60

CATGGATATC AGCTG 75

( 2 ) INFORMATION FOR SEQ ID NO:73:

( i ) SEQUENCE CHARACTERISTICS:
( A ) LENGTH: 75 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:73:

GATCCAGCTG ATATCCATGC GCACGGTAAC ACATCGAGCC CATACAAAAA CGTTCGCGAG 60

AATATTTAAA CATAG 75

( 2 ) INFORMATION FOR SEQ ID NO:74:

( i ) SEQUENCE CHARACTERISTICS:
( A ) LENGTH: 1464 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:74:

Met Asp Pro Val Val Leu Gln Arg Arg Asp Trp Glu Asn Pro Gly Val
1 5 10 15

Thr Gln Leu Asn Arg Leu Ala Ala His Pro Pro Phe Ala Ser Glu Arg
20 25 30

Phe Cys Met Gly Ser Gly Val Gly Val Pro Gly Val Gly Val Pro Gly
35 40 45

Val Gly Val Pro Gly Val Gly Val Pro Gly Val Gly Val Pro Gly Val
50 55 60

Gly Val Pro Gly Val Gly Val Pro Gly Val Gly Val Pro Gly Ala Gly
65 70 75 80

Ala Gly Ser Gly Ala Gly Ala Gly Ser Gly Val Gly Val Pro Gly Val
85 90 95

-continued

| | | | | | | | | | | | | | | | |
|---|---|---|---|---|---|---|---|---|---|---|---|---|---|---|---|
| Gly | Val | Pro | Gly | Val | Gly | Val | Pro | Gly | Val | Gly | Val | Pro | Gly | Val | Gly |
| | | | 100 | | | | | 105 | | | | | 110 | | |
| Val | Pro | Gly | Val | Gly | Val | Pro | Gly | Val | Gly | Val | Pro | Gly | Val | Gly | Val |
| | | 115 | | | | | 120 | | | | | 125 | | | |
| Pro | Gly | Ala | Gly | Ala | Gly | Ser | Gly | Ala | Gly | Ala | Gly | Ser | Gly | Val | Gly |
| | 130 | | | | | 135 | | | | | 140 | | | | |
| Val | Pro | Gly | Val | Gly | Val | Pro | Gly | Val | Gly | Val | Pro | Gly | Val | Gly | Val |
| 145 | | | | | 150 | | | | | 155 | | | | | 160 |
| Pro | Gly | Val | Gly | Val | Pro | Gly | Val | Gly | Val | Pro | Gly | Val | Gly | Val | Pro |
| | | | | 165 | | | | | 170 | | | | | 175 | |
| Gly | Val | Gly | Val | Pro | Gly | Ala | Gly | Ala | Gly | Ser | Gly | Ala | Gly | Ala | Gly |
| | | | 180 | | | | | 185 | | | | | 190 | | |
| Ser | Gly | Val | Gly | Val | Pro | Gly | Val | Gly | Val | Pro | Gly | Val | Gly | Val | Pro |
| | | 195 | | | | | 200 | | | | | 205 | | | |
| Gly | Val | Gly | Val | Pro | Gly | Val | Gly | Val | Pro | Gly | Val | Gly | Val | Pro | Gly |
| | 210 | | | | | 215 | | | | | 220 | | | | |
| Val | Gly | Val | Pro | Gly | Val | Gly | Val | Pro | Gly | Ala | Gly | Ala | Gly | Ser | Gly |
| 225 | | | | | 230 | | | | | 235 | | | | | 240 |
| Ala | Gly | Ala | Gly | Ser | Gly | Val | Gly | Val | Pro | Gly | Val | Gly | Val | Pro | Gly |
| | | | | 245 | | | | | 250 | | | | | 255 | |
| Val | Gly | Val | Pro | Gly | Val | Gly | Val | Pro | Gly | Val | Gly | Val | Pro | Gly | Val |
| | | | 260 | | | | | 265 | | | | | 270 | | |
| Gly | Val | Pro | Gly | Val | Gly | Val | Pro | Gly | Val | Gly | Val | Pro | Gly | Ala | Gly |
| | | 275 | | | | | 280 | | | | | 285 | | | |
| Ala | Gly | Ser | Gly | Ala | Gly | Ala | Gly | Ser | Gly | Val | Gly | Val | Pro | Gly | Val |
| | 290 | | | | | 295 | | | | | 300 | | | | |
| Gly | Val | Pro | Gly | Val | Gly | Val | Pro | Gly | Val | Gly | Val | Pro | Gly | Val | Gly |
| 305 | | | | | 310 | | | | | 315 | | | | | 320 |
| Val | Pro | Gly | Val | Gly | Val | Pro | Gly | Val | Gly | Val | Pro | Gly | Val | Gly | Val |
| | | | | 325 | | | | | 330 | | | | | 335 | |
| Pro | Gly | Ala | Gly | Ala | Gly | Ser | Gly | Ala | Gly | Ala | Gly | Ser | Gly | Val | Gly |
| | | | 340 | | | | | 345 | | | | | 350 | | |
| Val | Pro | Gly | Val | Gly | Val | Pro | Gly | Val | Gly | Val | Pro | Gly | Val | Gly | Val |
| | | 355 | | | | | 360 | | | | | 365 | | | |
| Pro | Gly | Val | Gly | Val | Pro | Gly | Val | Gly | Val | Pro | Gly | Val | Gly | Val | Pro |
| | 370 | | | | | 375 | | | | | 380 | | | | |
| Gly | Val | Gly | Val | Pro | Gly | Ala | Gly | Ala | Gly | Ser | Gly | Ala | Gly | Ala | Gly |
| 385 | | | | | 390 | | | | | 395 | | | | | 400 |
| Ser | Gly | Val | Gly | Val | Pro | Gly | Val | Gly | Val | Pro | Gly | Val | Gly | Val | Pro |
| | | | | 405 | | | | | 410 | | | | | 415 | |
| Gly | Val | Gly | Val | Pro | Gly | Val | Gly | Val | Pro | Gly | Val | Gly | Val | Pro | Gly |
| | | | 420 | | | | | 425 | | | | | 430 | | |
| Val | Gly | Val | Pro | Gly | Val | Gly | Val | Pro | Gly | Ala | Gly | Ala | Gly | Ser | Gly |
| | | 435 | | | | | 440 | | | | | 445 | | | |
| Ala | Gly | Ala | Gly | Ser | Gly | Val | Gly | Val | Pro | Gly | Val | Gly | Val | Pro | Gly |
| | 450 | | | | | 455 | | | | | 460 | | | | |
| Val | Gly | Val | Pro | Gly | Val | Gly | Val | Pro | Gly | Val | Gly | Val | Pro | Gly | Val |
| 465 | | | | | 470 | | | | | 475 | | | | | 480 |
| Gly | Val | Pro | Gly | Val | Gly | Val | Pro | Gly | Val | Gly | Val | Pro | Gly | Ala | Gly |
| | | | | 485 | | | | | 490 | | | | | 495 | |
| Ala | Gly | Ser | Gly | Ala | Gly | Ala | Gly | Ser | Gly | Val | Gly | Val | Pro | Gly | Val |
| | | | 500 | | | | | 505 | | | | | 510 | | |
| Gly | Val | Pro | Gly | Val | Gly | Val | Pro | Gly | Val | Gly | Val | Pro | Gly | Val | Gly |
| | | 515 | | | | | 520 | | | | | 525 | | | |

-continued

| | | | | | | | | | | | | | | | |
|---|---|---|---|---|---|---|---|---|---|---|---|---|---|---|---|
| Val | Pro | Gly | Val | Gly | Val | Pro | Gly | Val | Gly | Val | Pro | Gly | Val | Gly | Val |
| | 530 | | | | | 535 | | | | | 540 | | | | |
| Pro | Gly | Ala | Gly | Ala | Gly | Ser | Gly | Ala | Gly | Ala | Gly | Ser | Gly | Val | Gly |
| 545 | | | | | 550 | | | | | 555 | | | | | 560 |
| Val | Pro | Gly | Val | Gly | Val | Pro | Gly | Val | Gly | Val | Pro | Gly | Val | Gly | Val |
| | | | | 565 | | | | | 570 | | | | | 575 | |
| Pro | Gly | Val | Gly | Val | Pro | Gly | Val | Gly | Val | Pro | Gly | Val | Gly | Val | Pro |
| | | | 580 | | | | | 585 | | | | | 590 | | |
| Gly | Val | Gly | Val | Pro | Gly | Ala | Gly | Ala | Gly | Ser | Gly | Ala | Gly | Ala | Gly |
| | | 595 | | | | | 600 | | | | | 605 | | | |
| Ser | Gly | Val | Gly | Val | Pro | Gly | Val | Gly | Val | Pro | Gly | Val | Gly | Val | Pro |
| | 610 | | | | | 615 | | | | | 620 | | | | |
| Gly | Val | Gly | Val | Pro | Gly | Val | Gly | Val | Pro | Gly | Val | Gly | Val | Pro | Gly |
| 625 | | | | | 630 | | | | | 635 | | | | | 640 |
| Val | Gly | Val | Pro | Gly | Val | Gly | Val | Pro | Gly | Ala | Gly | Ala | Gly | Ser | Gly |
| | | | | 645 | | | | | 650 | | | | | 655 | |
| Ala | Gly | Ala | Gly | Ser | Gly | Val | Gly | Val | Pro | Gly | Val | Gly | Val | Pro | Gly |
| | | | 660 | | | | | 665 | | | | | 670 | | |
| Val | Gly | Val | Pro | Gly | Val | Gly | Val | Pro | Gly | Val | Gly | Val | Pro | Gly | Val |
| | | 675 | | | | | 680 | | | | | 685 | | | |
| Gly | Val | Pro | Gly | Val | Gly | Val | Pro | Gly | Val | Gly | Val | Pro | Gly | Ala | Gly |
| | 690 | | | | | 695 | | | | | 700 | | | | |
| Ala | Gly | Ser | Gly | Ala | Gly | Ala | Gly | Ser | Gly | Val | Gly | Val | Pro | Gly | Val |
| 705 | | | | | 710 | | | | | 715 | | | | | 720 |
| Gly | Val | Pro | Gly | Val | Gly | Val | Pro | Gly | Val | Gly | Val | Pro | Gly | Val | Gly |
| | | | | 725 | | | | | 730 | | | | | 735 | |
| Val | Pro | Gly | Val | Gly | Val | Pro | Gly | Val | Gly | Val | Pro | Gly | Val | Gly | Val |
| | | | 740 | | | | | 745 | | | | | 750 | | |
| Pro | Gly | Ala | Gly | Ala | Gly | Ser | Gly | Ala | Gly | Ala | Gly | Ser | Gly | Val | Gly |
| | | 755 | | | | | 760 | | | | | 765 | | | |
| Val | Pro | Gly | Val | Gly | Val | Pro | Gly | Val | Gly | Val | Pro | Gly | Val | Gly | Val |
| | 770 | | | | | 775 | | | | | 780 | | | | |
| Pro | Gly | Val | Gly | Val | Pro | Gly | Val | Gly | Val | Pro | Gly | Val | Gly | Val | Pro |
| 785 | | | | | 790 | | | | | 795 | | | | | 800 |
| Gly | Val | Gly | Val | Pro | Gly | Ala | Gly | Ala | Gly | Ser | Gly | Ala | Gly | Ala | Gly |
| | | | | 805 | | | | | 810 | | | | | 815 | |
| Ser | Gly | Val | Gly | Val | Pro | Gly | Val | Gly | Val | Pro | Gly | Val | Gly | Val | Pro |
| | | | 820 | | | | | 825 | | | | | 830 | | |
| Gly | Val | Gly | Val | Pro | Gly | Val | Gly | Val | Pro | Gly | Val | Gly | Val | Pro | Gly |
| | | 835 | | | | | 840 | | | | | 845 | | | |
| Val | Gly | Val | Pro | Gly | Val | Gly | Val | Pro | Gly | Ala | Gly | Ala | Gly | Ser | Gly |
| | 850 | | | | | 855 | | | | | 860 | | | | |
| Ala | Gly | Ala | Gly | Ser | Gly | Val | Gly | Val | Pro | Gly | Val | Gly | Val | Pro | Gly |
| 865 | | | | | 870 | | | | | 875 | | | | | 880 |
| Val | Gly | Val | Pro | Gly | Val | Gly | Val | Pro | Gly | Val | Gly | Val | Pro | Gly | Val |
| | | | | 885 | | | | | 890 | | | | | 895 | |
| Gly | Val | Pro | Gly | Val | Gly | Val | Pro | Gly | Val | Gly | Val | Pro | Gly | Ala | Gly |
| | | | 900 | | | | | 905 | | | | | 910 | | |
| Ala | Gly | Ser | Gly | Ala | Gly | Ala | Gly | Ser | Gly | Val | Gly | Val | Pro | Gly | Val |
| | | 915 | | | | | 920 | | | | | 925 | | | |
| Gly | Val | Pro | Gly | Val | Gly | Val | Pro | Gly | Val | Gly | Val | Pro | Gly | Val | Gly |
| | 930 | | | | | 935 | | | | | 940 | | | | |
| Val | Pro | Gly | Val | Gly | Val | Pro | Gly | Val | Gly | Val | Pro | Gly | Val | Gly | Val |

-continued 945 950 955 960

Pro Gly Ala Gly Ala Gly Ser Gly Ala Gly Ala Gly Ser Gly Val Gly
965 970 975

Val Pro Gly Val Gly Val Pro Gly Val Gly Val Pro Gly Val Gly Val
980 985 990

Pro Gly Val Gly Val Pro Gly Val Gly Val Pro Gly Val Gly Val Pro
995 1000 1005

Gly Val Gly Val Pro Gly Ala Gly Ala Gly Ser Gly Ala Gly Ala Gly
1010 1015 1020

Ser Gly Val Gly Val Pro Gly Val Gly Val Pro Gly Val Gly Val Pro
1025 1030 1035 1040

Gly Val Gly Val Pro Gly Val Gly Val Pro Gly Val Gly Val Pro Gly
1045 1050 1055

Val Gly Val Pro Gly Val Gly Val Pro Gly Ala Gly Ala Gly Ser Gly
1060 1065 1070

Ala Gly Ala Gly Ser Gly Val Gly Val Pro Gly Val Gly Val Pro Gly
1075 1080 1085

Val Gly Val Pro Gly Val Gly Val Pro Gly Val Gly Val Pro Gly Val
1090 1095 1100

Gly Val Pro Gly Val Gly Val Pro Gly Val Gly Val Pro Gly Ala Gly
1105 1110 1115 1120

Ala Gly Ser Gly Ala Gly Ala Gly Ser Gly Val Gly Val Pro Gly Val
1125 1130 1135

Gly Val Pro Gly Val Gly Val Pro Gly Val Gly Val Pro Gly Val Gly
1140 1145 1150

Val Pro Gly Val Gly Val Pro Gly Val Gly Val Pro Gly Val Gly Val
1155 1160 1165

Pro Gly Ala Gly Ala Gly Ser Gly Ala Gly Ala Gly Ser Gly Val Gly
1170 1175 1180

Val Pro Gly Val Gly Val Pro Gly Val Gly Val Pro Gly Val Gly Val
1185 1190 1195 1200

Pro Gly Val Gly Val Pro Gly Val Gly Val Pro Gly Val Gly Val Pro
1205 1210 1215

Gly Val Gly Val Pro Gly Ala Gly Ala Gly Ser Gly Ala Gly Ala Gly
1220 1225 1230

Ser Gly Val Gly Val Pro Gly Val Gly Val Pro Gly Val Gly Val Pro
1235 1240 1245

Gly Val Gly Val Pro Gly Val Gly Val Pro Gly Val Gly Val Pro Gly
1250 1255 1260

Val Gly Val Pro Gly Val Gly Val Pro Gly Ala Gly Ala Gly Ser Gly
1265 1270 1275 1280

Ala Gly Ala Gly Ser Gly Val Gly Val Pro Gly Val Gly Val Pro Gly
1285 1290 1295

Val Gly Val Pro Gly Val Gly Val Pro Gly Val Gly Val Pro Gly Val
1300 1305 1310

Gly Val Pro Gly Val Gly Val Pro Gly Val Gly Val Pro Gly Ala Gly
1315 1320 1325

Ala Gly Ser Gly Ala Gly Ala Gly Ser Gly Val Gly Val Pro Gly Val
1330 1335 1340

Gly Val Pro Gly Val Gly Val Pro Gly Val Gly Val Pro Gly Val Gly
1345 1350 1355 1360

Val Pro Gly Val Gly Val Pro Gly Val Gly Val Pro Gly Val Gly Val
1365 1370 1375

Pro Gly Ala Gly Ala Gly Ser Gly Ala Gly Ala Gly Ser Gly Val Gly
1380 1385 1390

Val Pro Gly Val Gly Val Pro Gly Val Gly Val Pro Gly Val Gly Val
1395 1400 1405

Pro Gly Val Gly Val Pro Gly Val Gly Val Pro Gly Val Gly Val Pro
1410 1415 1420

Gly Val Gly Val Pro Gly Ala Gly Ala Gly Ser Gly Ala Gly Ala Gly
1425 1430 1435 1440

Ser Met Cys Tyr Arg Ala His Gly Gln Leu Ser Ala Gly Arg Tyr His
1445 1450 1455

Tyr Gln Leu Val Trp Cys Gln Lys
1460

( 2 ) INFORMATION FOR SEQ ID NO:75:

( i ) SEQUENCE CHARACTERISTICS:
( A ) LENGTH: 72 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:75:

AATTCGGTGC CCGGTGTAGG AGTTCCGGGT GTAGGCGTTC CCGGGGTAGG CGTTCCGGGA 60

GTAGGGGTGC CA 72

( 2 ) INFORMATION FOR SEQ ID NO:76:

( i ) SEQUENCE CHARACTERISTICS:
( A ) LENGTH: 73 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:76:

GCCACGGGCC ACATCCTCAA GGCCCACATC CGCCAAGGGC CCCATCCGCA AGGCCCTCAT 60

CCCCACGGTT CGA 73

( 2 ) INFORMATION FOR SEQ ID NO:77:

( i ) SEQUENCE CHARACTERISTICS:
( A ) LENGTH: 859 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:77:

Met Asp Pro Val Val Leu Gln Arg Arg Asp Trp Glu Asn Pro Gly Val
1 5 10 15

Thr Gln Leu Asn Arg Leu Ala Ala His Pro Pro Phe Ala Arg Asn Ile
20 25 30

Leu Ala Ile Arg Trp Val Pro Gly Val Gly Val Pro Gly Val Gly Val
35 40 45

Pro Gly Val Gly Val Pro Gly Val Gly Val Pro Gly Val Gly Val Pro
50 55 60

Gly Val Gly Val Pro Gly Val Gly Val Pro Gly Val Gly Val Pro Gly
65 70 75 80

Val Gly Val Pro Gly Val Gly Val Pro Gly Val Gly Val Pro Gly Val
85 90 95

Gly Val Pro Gly Val Gly Val Pro Gly Val Gly Val Pro Gly Val Gly
100 105 110

Val Pro Gly Val Gly Val Pro Gly Val Gly Val Pro Gly Val Gly Val
115 120 125

Pro Gly Val Gly Val Pro Gly Val Gly Val Pro Gly Val Gly Val Pro
130 135 140

Gly Val Gly Val Pro Gly Val Gly Val Pro Gly Val Gly Val Pro Gly
145 150 155 160

Val Gly Val Pro Gly Val Gly Val Pro Gly Val Gly Val Pro Gly Val
165 170 175

Gly Val Pro Gly Val Gly Val Pro Gly Val Gly Val Pro Gly Val Gly
180 185 190

Val Pro Gly Val Gly Val Pro Gly Val Gly Val Pro Gly Val Gly Val
195 200 205

Pro Gly Val Gly Val Pro Gly Val Gly Val Pro Gly Val Gly Val Pro
210 215 220

Gly Val Gly Val Pro Gly Val Gly Val Pro Gly Val Gly Val Pro Gly
225 230 235 240

Val Gly Val Pro Gly Val Gly Val Pro Gly Val Gly Val Pro Gly Val
245 250 255

Gly Val Pro Gly Val Gly Val Pro Gly Val Gly Val Pro Gly Val Gly
260 265 270

Val Pro Gly Val Gly Val Pro Gly Val Gly Val Pro Gly Val Gly Val
275 280 285

Pro Gly Val Gly Val Pro Gly Val Gly Val Pro Gly Val Gly Val Pro
290 295 300

Gly Val Gly Val Pro Gly Val Gly Val Pro Gly Val Gly Val Pro Gly
305 310 315 320

Val Gly Val Pro Gly Val Gly Val Pro Gly Val Gly Val Pro Gly Val
325 330 335

Gly Val Pro Gly Val Gly Val Pro Gly Val Gly Val Pro Gly Val Gly
340 345 350

Val Pro Gly Val Gly Val Pro Gly Val Gly Val Pro Gly Val Gly Val
355 360 365

Pro Gly Val Gly Val Pro Gly Val Gly Val Pro Gly Val Gly Val Pro
370 375 380

Gly Val Gly Val Pro Gly Val Gly Val Pro Gly Val Gly Val Pro Gly
385 390 395 400

Val Gly Val Pro Gly Val Gly Val Pro Gly Val Gly Val Pro Gly Val
405 410 415

Gly Val Pro Gly Val Gly Val Pro Gly Val Gly Val Pro Gly Val Gly
420 425 430

Val Pro Gly Val Gly Val Pro Gly Val Gly Val Pro Gly Val Gly Val
435 440 445

Pro Gly Val Gly Val Pro Gly Val Gly Val Pro Gly Val Gly Val Pro
450 455 460

Gly Val Gly Val Pro Gly Val Gly Val Pro Gly Val Gly Val Pro Gly
465 470 475 480

Val Gly Val Pro Gly Val Gly Val Pro Gly Val Gly Val Pro Gly Val
485 490 495

Gly Val Pro Gly Val Gly Val Pro Gly Val Gly Val Pro Gly Val Gly
500 505 510

-continued

Val Pro Gly Val Gly Val Pro Gly Val Gly Val Pro Gly Val Gly Val
515 520 525

Pro Gly Val Gly Val Pro Gly Val Gly Val Pro Gly Val Gly Val Pro
530 535 540

Gly Val Gly Val Pro Gly Val Gly Val Pro Gly Val Gly Val Pro Gly
545 550 555 560

Val Gly Val Pro Gly Val Gly Val Pro Gly Val Gly Val Pro Gly Val
565 570 575

Gly Val Pro Gly Val Gly Val Pro Gly Val Gly Val Pro Gly Val Gly
580 585 590

Val Pro Gly Val Gly Val Pro Gly Val Gly Val Pro Gly Val Gly Val
595 600 605

Pro Gly Val Gly Val Pro Gly Val Gly Val Pro Gly Val Gly Val Pro
610 615 620

Gly Val Gly Val Pro Gly Val Gly Val Pro Gly Val Gly Val Pro Gly
625 630 635 640

Val Gly Val Pro Gly Val Gly Val Pro Gly Val Gly Val Pro Gly Val
645 650 655

Gly Val Pro Gly Val Gly Val Pro Gly Val Gly Val Pro Gly Val Gly
660 665 670

Val Pro Gly Val Gly Val Pro Gly Val Gly Val Pro Gly Val Gly Val
675 680 685

Pro Gly Val Gly Val Pro Gly Val Gly Val Pro Gly Val Gly Val Pro
690 695 700

Gly Val Gly Val Pro Gly Val Gly Val Pro Gly Val Gly Val Pro Gly
705 710 715 720

Val Gly Val Pro Gly Val Gly Val Pro Gly Val Gly Val Pro Gly Val
725 730 735

Gly Val Pro Gly Val Gly Val Pro Gly Val Gly Val Pro Gly Val Gly
740 745 750

Val Pro Gly Val Gly Val Pro Gly Val Gly Val Pro Gly Val Gly Val
755 760 765

Pro Gly Val Gly Val Pro Gly Val Gly Val Pro Gly Val Gly Val Pro
770 775 780

Gly Val Gly Val Pro Gly Val Gly Val Pro Gly Val Gly Val Pro Gly
785 790 795 800

Val Gly Val Pro Gly Val Gly Val Pro Gly Val Gly Val Pro Gly Val
805 810 815

Gly Val Pro Gly Val Gly Val Pro Gly Val Gly Val Pro Gly Val Gly
820 825 830

Val Pro Gly Val Gly Val Pro Trp Thr Arg Val Asp Leu Ser Ala Gly
835 840 845

Arg Tyr His Tyr Gln Leu Val Trp Cys Gln Lys
850 855

( 2 ) INFORMATION FOR SEQ ID NO:78:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:78:

-continued

GTGCGCAGCT GGTACGTAGC TGCA 24

( 2 ) INFORMATION FOR SEQ ID NO:79:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:79:

GCTACGTACC AGCTGCGCAC TGCA 24

( 2 ) INFORMATION FOR SEQ ID NO:80:

( i ) SEQUENCE CHARACTERISTICS:
( A ) LENGTH: 2100 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:80:

Met Asp Pro Val Val Leu Gln Arg Arg Asp Trp Glu Asn Pro Gly Val
1 5 10 15

Thr Gln Leu Asn Arg Leu Ala Ala His Pro Pro Phe Ala Ser Asp Pro
20 25 30

Met Gly Ala Gly Ser Gly Ala Gly Ala Gly Ser Gly Ala Gly Ala Gly
35 40 45

Ser Gly Ala Gly Ala Gly Ser Gly Ala Gly Ala Gly Ser Gly Ala Gly
50 55 60

Ala Gly Ser Gly Ala Gly Ala Gly Ser Gly Ala Ala Val Pro Gly Val
65 70 75 80

Gly Val Pro Gly Val Gly Val Pro Gly Val Gly Val Pro Gly Val Gly
85 90 95

Val Ala Ala Gly Tyr Gly Ala Gly Ala Gly Ser Gly Ala Gly Ala Gly
100 105 110

Ser Gly Ala Gly Ala Gly Ser Gly Ala Gly Ala Gly Ser Gly Ala Gly
115 120 125

Ala Gly Ser Gly Ala Gly Ala Gly Ser Gly Ala Gly Ala Gly Ser Gly
130 135 140

Ala Gly Ala Gly Ser Gly Ala Gly Ala Gly Ser Gly Ala Ala Val Pro
145 150 155 160

Gly Val Gly Val Pro Gly Val Gly Val Pro Gly Val Gly Val Pro Gly
165 170 175

Val Gly Val Ala Ala Gly Tyr Gly Ala Gly Ala Gly Ser Gly Ala Gly
180 185 190

Ala Gly Ser Gly Ala Gly Ala Gly Ser Gly Ala Gly Ala Gly Ser Gly
195 200 205

Ala Gly Ala Gly Ser Gly Ala Gly Ala Gly Ser Gly Ala Gly Ala Gly
210 215 220

Ser Gly Ala Gly Ala Gly Ser Gly Ala Gly Ala Gly Ser Gly Ala Ala
225 230 235 240

Val Pro Gly Val Gly Val Pro Gly Val Gly Val Pro Gly Val Gly Val
245 250 255

Pro Gly Val Gly Val Ala Ala Gly Tyr Gly Ala Gly Ala Gly Ser Gly
260 265 270

-continued

Ala Gly Ala Gly Ser Gly Ala Gly Ala Gly Ser Gly Ala Gly Ala Gly
275 280 285

Ser Gly Ala Gly Ala Gly Ser Gly Ala Gly Ala Gly Ser Gly Ala Gly
290 295 300

Ala Gly Ser Gly Ala Gly Ala Gly Ser Gly Ala Gly Ala Gly Ser Gly
305 310 315 320

Ala Ala Val Pro Gly Val Gly Val Pro Gly Val Gly Val Pro Gly Val
325 330 335

Gly Val Pro Gly Val Gly Val Ala Ala Gly Tyr Gly Ala Gly Ala Gly
340 345 350

Ser Gly Ala Gly Ala Gly Ser Gly Ala Gly Ala Gly Ser Gly Ala Gly
355 360 365

Ala Gly Ser Gly Ala Gly Ala Gly Ser Gly Ala Gly Ala Gly Ser Gly
370 375 380

Ala Gly Ala Gly Ser Gly Ala Gly Ala Gly Ser Gly Ala Gly Ala Gly
385 390 395 400

Ser Gly Ala Ala Val Pro Gly Val Gly Val Pro Gly Val Gly Val Pro
405 410 415

Gly Val Gly Val Pro Gly Val Gly Val Ala Ala Gly Tyr Gly Ala Gly
420 425 430

Ala Gly Ser Gly Ala Gly Ala Gly Ser Gly Ala Gly Ala Gly Ser Gly
435 440 445

Ala Gly Ala Gly Ser Gly Ala Gly Ala Gly Ser Gly Ala Gly Ala Gly
450 455 460

Ser Gly Ala Gly Ala Gly Ser Gly Ala Gly Ala Gly Ser Gly Ala Gly
465 470 475 480

Ala Gly Ser Gly Ala Ala Val Pro Gly Val Gly Val Pro Gly Val Gly
485 490 495

Val Pro Gly Val Gly Val Pro Gly Val Gly Val Ala Ala Gly Tyr Gly
500 505 510

Ala Gly Ala Gly Ser Gly Ala Gly Ala Gly Ser Gly Ala Gly Ala Gly
515 520 525

Ser Gly Ala Gly Ala Gly Ser Gly Ala Gly Ala Gly Ser Gly Ala Gly
530 535 540

Ala Gly Ser Gly Ala Gly Ala Gly Ser Gly Ala Gly Ala Gly Ser Gly
545 550 555 560

Ala Gly Ala Gly Ser Gly Ala Ala Val Pro Gly Val Gly Val Pro Gly
565 570 575

Val Gly Val Pro Gly Val Gly Val Pro Gly Val Gly Val Ala Ala Gly
580 585 590

Tyr Gly Ala Gly Ala Gly Ser Gly Ala Gly Ala Gly Ser Gly Ala Gly
595 600 605

Ala Gly Ser Gly Ala Gly Ala Gly Ser Gly Ala Gly Ala Gly Ser Gly
610 615 620

Ala Gly Ala Gly Ser Gly Ala Gly Ala Gly Ser Gly Ala Gly Ala Gly
625 630 635 640

Ser Gly Ala Gly Ala Gly Ser Gly Ala Ala Val Pro Gly Val Gly Val
645 650 655

Pro Gly Val Gly Val Pro Gly Val Gly Val Pro Gly Val Gly Val Ala
660 665 670

Ala Gly Tyr Gly Ala Gly Ala Gly Ser Gly Ala Gly Ala Gly Ser Gly
675 680 685

Ala Gly Ala Gly Ser Gly Ala Gly Ala Gly Ser Gly Ala Gly Ala Gly

-continued 690 695 700

Ser Gly Ala Gly Ala Gly Ser Gly Ala Gly Ala Gly Ser Gly Ala Gly
705 710 715 720

Ala Gly Ser Gly Ala Gly Ala Gly Ser Gly Ala Ala Val Pro Gly Val
725 730 735

Gly Val Pro Gly Val Gly Val Pro Gly Val Gly Val Pro Gly Val Gly
740 745 750

Val Ala Ala Gly Tyr Gly Ala Gly Ala Gly Ser Gly Ala Gly Ala Gly
755 760 765

Ser Gly Ala Gly Ala Gly Ser Gly Ala Gly Ala Gly Ser Gly Ala Gly
770 775 780

Ala Gly Ser Gly Ala Gly Ala Gly Ser Gly Ala Gly Ala Gly Ser Gly
785 790 795 800

Ala Gly Ala Gly Ser Gly Ala Gly Ala Gly Ser Gly Ala Ala Val Pro
805 810 815

Gly Val Gly Val Pro Gly Val Gly Val Pro Gly Val Gly Val Pro Gly
820 825 830

Val Gly Val Ala Ala Gly Tyr Gly Ala Gly Ala Gly Ser Gly Ala Gly
835 840 845

Ala Gly Ser Gly Ala Gly Ala Gly Ser Gly Ala Gly Ala Gly Ser Gly
850 855 860

Ala Gly Ala Gly Ser Gly Ala Gly Ala Gly Ser Gly Ala Gly Ala Gly
865 870 875 880

Ser Gly Ala Gly Ala Gly Ser Gly Ala Gly Ala Gly Ser Gly Ala Ala
885 890 895

Val Pro Gly Val Gly Val Pro Gly Val Gly Val Pro Gly Val Gly Val
900 905 910

Pro Gly Val Gly Val Ala Ala Gly Tyr Gly Ala Gly Ala Gly Ser Gly
915 920 925

Ala Gly Ala Gly Ser Gly Ala Gly Ala Gly Ser Gly Ala Gly Ala Gly
930 935 940

Ser Gly Ala Gly Ala Gly Ser Gly Ala Gly Ala Gly Ser Gly Ala Gly
945 950 955 960

Ala Gly Ser Gly Ala Gly Ala Gly Ser Gly Ala Gly Ala Gly Ser Gly
965 970 975

Ala Ala Val Pro Gly Val Gly Val Pro Gly Val Gly Val Pro Gly Val
980 985 990

Gly Val Pro Gly Val Gly Val Ala Ala Gly Tyr Gly Ala Gly Ala Gly
995 1000 1005

Ser Gly Ala Gly Ala Gly Ser Gly Ala Gly Ala Gly Ser Gly Ala Gly
1010 1015 1020

Ala Gly Ser Gly Ala Gly Ala Gly Ser Gly Ala Gly Ala Gly Ser Gly
1025 1030 1035 1040

Ala Gly Ala Gly Ser Gly Ala Gly Ala Gly Ser Gly Ala Gly Ala Gly
1045 1050 1055

Ser Gly Ala Ala Val Pro Gly Val Gly Val Pro Gly Val Gly Val Pro
1060 1065 1070

Gly Val Gly Val Pro Gly Val Gly Val Ala Ala Gly Tyr Gly Ala Gly
1075 1080 1085

Ala Gly Ser Gly Ala Gly Ala Gly Ser Gly Ala Gly Ala Gly Ser Gly
1090 1095 1100

Ala Gly Ala Gly Ser Gly Ala Gly Ala Gly Ser Gly Ala Gly Ala Gly
1105 1110 1115 1120

-continued

Ser Gly Ala Gly Ala Gly Ser Gly Ala Gly Ala Gly Ser Gly Ala Gly
1125 1130 1135

Ala Gly Ser Gly Ala Ala Val Pro Gly Val Gly Val Pro Gly Val Gly
1140 1145 1150

Val Pro Gly Val Gly Val Pro Gly Val Gly Val Ala Ala Gly Tyr Gly
1155 1160 1165

Ala Gly Ala Gly Ser Gly Ala Gly Ala Gly Ser Gly Ala Gly Ala Gly
1170 1175 1180

Ser Gly Ala Gly Ala Gly Ser Gly Ala Gly Ala Gly Ser Gly Ala Gly
1185 1190 1195 1200

Ala Gly Ser Gly Ala Gly Ala Gly Ser Gly Ala Gly Ala Gly Ser Gly
1205 1210 1215

Ala Gly Ala Gly Ser Gly Ala Ala Val Pro Gly Val Gly Val Pro Gly
1220 1225 1230

Val Gly Val Pro Gly Val Gly Val Pro Gly Val Gly Val Ala Ala Gly
1235 1240 1245

Tyr Gly Ala Gly Ala Gly Ser Gly Ala Gly Ala Gly Ser Gly Ala Gly
1250 1255 1260

Ala Gly Ser Gly Ala Gly Ala Gly Ser Gly Ala Gly Ala Gly Ser Gly
1265 1270 1275 1280

Ala Gly Ala Gly Ser Gly Ala Gly Ala Gly Ser Gly Ala Gly Ala Gly
1285 1290 1295

Ser Gly Ala Gly Ala Gly Ser Gly Ala Ala Val Pro Gly Val Gly Val
1300 1305 1310

Pro Gly Val Gly Val Pro Gly Val Gly Val Pro Gly Val Gly Val Ala
1315 1320 1325

Ala Gly Tyr Gly Ala Gly Ala Gly Ser Gly Ala Gly Ala Gly Ser Gly
1330 1335 1340

Ala Gly Ala Gly Ser Gly Ala Gly Ala Gly Ser Gly Ala Gly Ala Gly
1345 1350 1355 1360

Ser Gly Ala Gly Ala Gly Ser Gly Ala Gly Ala Gly Ser Gly Ala Gly
1365 1370 1375

Ala Gly Ser Gly Ala Gly Ala Gly Ser Gly Ala Ala Val Pro Gly Val
1380 1385 1390

Gly Val Pro Gly Val Gly Val Pro Gly Val Gly Val Pro Gly Val Gly
1395 1400 1405

Val Ala Ala Gly Tyr Gly Ala Gly Ala Gly Ser Gly Ala Gly Ala Gly
1410 1415 1420

Ser Gly Ala Gly Ala Gly Ser Gly Ala Gly Ala Gly Ser Gly Ala Gly
1425 1430 1435 1440

Ala Gly Ser Gly Ala Gly Ala Gly Ser Gly Ala Gly Ala Gly Ser Gly
1445 1450 1455

Ala Gly Ala Gly Ser Gly Ala Gly Ala Gly Ser Gly Ala Ala Val Pro
1460 1465 1470

Gly Val Gly Val Pro Gly Val Gly Val Pro Gly Val Gly Val Pro Gly
1475 1480 1485

Val Gly Val Ala Ala Gly Tyr Gly Ala Gly Ala Gly Ser Gly Ala Gly
1490 1495 1500

Ala Gly Ser Gly Ala Gly Ala Gly Ser Gly Ala Gly Ala Gly Ser Gly
1505 1510 1515 1520

Ala Gly Ala Gly Ser Gly Ala Gly Ala Gly Ser Gly Ala Gly Ala Gly
1525 1530 1535

Ser Gly Ala Gly Ala Gly Ser Gly Ala Gly Ala Gly Ser Gly Ala Ala
1540 1545 1550

-continued

Val Pro Gly Val Gly Val Pro Gly Val Gly Val Pro Gly Val Gly Val
1555 1560 1565

Pro Gly Val Gly Val Ala Ala Gly Tyr Gly Ala Gly Ala Gly Ser Gly
1570 1575 1580

Ala Gly Ala Gly Ser Gly Ala Gly Ala Gly Ser Gly Ala Gly Ala Gly
1585 1590 1595 1600

Ser Gly Ala Gly Ala Gly Ser Gly Ala Gly Ala Gly Ser Gly Ala Gly
1605 1610 1615

Ala Gly Ser Gly Ala Gly Ala Gly Ser Gly Ala Gly Ala Gly Ser Gly
1620 1625 1630

Ala Ala Val Pro Gly Val Gly Val Pro Gly Val Gly Val Pro Gly Val
1635 1640 1645

Gly Val Pro Gly Val Gly Val Ala Ala Gly Tyr Gly Ala Gly Ala Gly
1650 1655 1660

Ser Gly Ala Gly Ala Gly Ser Gly Ala Gly Ala Gly Ser Gly Ala Gly
1665 1670 1675 1680

Ala Gly Ser Gly Ala Gly Ala Gly Ser Gly Ala Gly Ala Gly Ser Gly
1685 1690 1695

Ala Gly Ala Gly Ser Gly Ala Gly Ala Gly Ser Gly Ala Gly Ala Gly
1700 1705 1710

Ser Gly Ala Ala Val Pro Gly Val Gly Val Pro Gly Val Gly Val Pro
1715 1720 1725

Gly Val Gly Val Pro Gly Val Gly Val Ala Ala Gly Tyr Gly Ala Gly
1730 1735 1740

Ala Gly Ser Gly Ala Gly Ala Gly Ser Gly Ala Gly Ala Gly Ser Gly
1745 1750 1755 1760

Ala Gly Ala Gly Ser Gly Ala Gly Ala Gly Ser Gly Ala Gly Ala Gly
1765 1770 1775

Ser Gly Ala Gly Ala Gly Ser Gly Ala Gly Ala Gly Ser Gly Ala Gly
1780 1785 1790

Ala Gly Ser Gly Ala Ala Val Pro Gly Val Gly Val Pro Gly Val Gly
1795 1800 1805

Val Pro Gly Val Gly Val Pro Gly Val Gly Val Ala Ala Gly Tyr Gly
1810 1815 1820

Ala Gly Ala Gly Ser Gly Ala Gly Ala Gly Ser Gly Ala Gly Ala Gly
1825 1830 1835 1840

Ser Gly Ala Gly Ala Gly Ser Gly Ala Gly Ala Gly Ser Gly Ala Gly
1845 1850 1855

Ala Gly Ser Gly Ala Gly Ala Gly Ser Gly Ala Gly Ala Gly Ser Gly
1860 1865 1870

Ala Gly Ala Gly Ser Gly Ala Ala Val Pro Gly Val Gly Val Pro Gly
1875 1880 1885

Val Gly Val Pro Gly Val Gly Val Pro Gly Val Gly Val Ala Ala Gly
1890 1895 1900

Tyr Gly Ala Gly Ala Gly Ser Gly Ala Gly Ala Gly Ser Gly Ala Gly
1905 1910 1915 1920

Ala Gly Ser Gly Ala Gly Ala Gly Ser Gly Ala Gly Ala Gly Ser Gly
1925 1930 1935

Ala Gly Ala Gly Ser Gly Ala Gly Ala Gly Ser Gly Ala Gly Ala Gly
1940 1945 1950

Ser Gly Ala Gly Ala Gly Ser Gly Ala Ala Val Pro Gly Val Gly Val
1955 1960 1965

Pro Gly Val Gly Val Pro Gly Val Gly Val Pro Gly Val Gly Val Ala

-continued 1970 1975 1980

Ala Gly Tyr Gly Ala Gly Ala Gly Ser Gly Ala Gly Ala Gly Ser Gly
1985 1990 1995 2000

Ala Gly Ala Gly Ser Gly Ala Gly Ala Gly Ser Gly Ala Gly Ala Gly
2005 2010 2015

Ser Gly Ala Gly Ala Gly Ser Gly Ala Gly Ala Gly Ser Gly Ala Gly
2020 2025 2030

Ala Gly Ser Gly Ala Gly Ala Gly Ser Gly Ala Ala Val Pro Gly Val
2035 2040 2045

Gly Val Pro Gly Val Gly Val Pro Gly Val Gly Val Pro Gly Val Gly
2050 2055 2060

Val Ala Ala Gly Tyr Gly Ala Gly Ala Gly Ser Gly Ala Gly Ala Gly
2065 2070 2075 2080

Ser Gly Ala Gly Ala Met Asp Pro Gly Arg Tyr His Tyr Gln Leu Val
2085 2090 2095

Trp Cys Gln Lys
2100

( 2 ) INFORMATION FOR SEQ ID NO:81:

( i ) SEQUENCE CHARACTERISTICS:
( A ) LENGTH: 2055 amino acids
( B ) TYPE: amino acid
( C ) STRANDEDNESS: single
( D ) TOPOLOGY: linear ( i i ) MOLECULE TYPE: cDNA ( x i ) SEQUENCE DESCRIPTION: SEQ ID NO:81:

Met Asp Pro Val Val Leu Gln Arg Arg Asp Trp Glu Asn Pro Gly Val
1 5 10 15

Thr Gln Leu Asn Arg Leu Ala Ala His Pro Pro Phe Ala Ser Asp Pro
20 25 30

Met Gly Ala Gly Ser Gly Ala Gly Ala Gly Ser Gly Ala Gly Ala Gly
35 40 45

Ser Gly Val Gly Val Pro Gly Val Gly Val Pro Gly Val Gly Val Pro
50 55 60

Gly Val Gly Val Pro Gly Val Gly Val Pro Gly Val Gly Val Pro Gly
65 70 75 80

Val Gly Val Pro Gly Val Gly Val Pro Gly Ala Gly Ala Gly Ser Gly
85 90 95

Ala Gly Ala Gly Ser Gly Ala Gly Ala Gly Ser Gly Ala Gly Ala Gly
100 105 110

Ser Gly Ala Gly Ala Gly Ser Gly Ala Gly Ala Gly Ser Gly Ala Ala
115 120 125

Gly Tyr Gly Ala Gly Ala Gly Ser Gly Ala Gly Ala Gly Ser Gly Ala
130 135 140

Gly Ala Gly Ser Gly Ala Gly Ala Gly Ser Gly Ala Gly Ala Gly Ser
145 150 155 160

Gly Val Gly Val Pro Gly Val Gly Val Pro Gly Val Gly Val Pro Gly
165 170 175

Val Gly Val Pro Gly Val Gly Val Pro Gly Val Gly Val Pro Gly Val
180 185 190

Gly Val Pro Gly Val Gly Val Pro Gly Ala Gly Ala Gly Ser Gly Ala
195 200 205

Gly Ala Gly Ser Gly Ala Gly Ala Gly Ser Gly Ala Gly Ala Gly Ser
210 215 220

-continued

Gly Ala Gly Ala Gly Ser Gly Ala Gly Ala Gly Ser Gly Ala Ala Gly
225 230 235 240

Tyr Gly Ala Gly Ala Gly Ser Gly Ala Gly Ala Gly Ser Gly Ala Gly
245 250 255

Ala Gly Ser Gly Ala Gly Ala Gly Ser Gly Ala Gly Ala Gly Ser Gly
260 265 270

Val Gly Val Pro Gly Val Gly Val Pro Gly Val Gly Val Pro Gly Val
275 280 285

Gly Val Pro Gly Val Gly Val Pro Gly Val Gly Val Pro Gly Val Gly
290 295 300

Val Pro Gly Val Gly Val Pro Gly Ala Gly Ala Gly Ser Gly Ala Gly
305 310 315 320

Ala Gly Ser Gly Ala Gly Ala Gly Ser Gly Ala Gly Ala Gly Ser Gly
325 330 335

Ala Gly Ala Gly Ser Gly Ala Gly Ala Gly Ser Gly Ala Ala Gly Tyr
340 345 350

Gly Ala Gly Ala Gly Ser Gly Ala Gly Ala Gly Ser Gly Ala Gly Ala
355 360 365

Gly Ser Gly Ala Gly Ala Gly Ser Gly Ala Gly Ala Gly Ser Gly Val
370 375 380

Gly Val Pro Gly Val Gly Val Pro Gly Val Gly Val Pro Gly Val Gly
385 390 395 400

Val Pro Gly Val Gly Val Pro Gly Val Gly Val Pro Gly Val Gly Val
405 410 415

Pro Gly Val Gly Val Pro Gly Ala Gly Ala Gly Ser Gly Ala Gly Ala
420 425 430

Gly Ser Gly Ala Gly Ala Gly Ser Gly Ala Gly Ala Gly Ser Gly Ala
435 440 445

Gly Ala Gly Ser Gly Ala Gly Ala Gly Ser Gly Ala Ala Gly Tyr Gly
450 455 460

Ala Gly Ala Gly Ser Gly Ala Gly Ala Gly Ser Gly Ala Gly Ala Gly
465 470 475 480

Ser Gly Ala Gly Ala Gly Ser Gly Ala Gly Ala Gly Ser Gly Val Gly
485 490 495

Val Pro Gly Val Gly Val Pro Gly Val Gly Val Pro Gly Val Gly Val
500 505 510

Pro Gly Val Gly Val Pro Gly Val Gly Val Pro Gly Val Gly Val Pro
515 520 525

Gly Val Gly Val Pro Gly Ala Gly Ala Gly Ser Gly Ala Gly Ala Gly
530 535 540

Ser Gly Ala Gly Ala Gly Ser Gly Ala Gly Ala Gly Ser Gly Ala Gly
545 550 555 560

Ala Gly Ser Gly Ala Gly Ala Gly Ser Gly Ala Ala Gly Tyr Gly Ala
565 570 575

Gly Ala Gly Ser Gly Ala Gly Ala Gly Ser Gly Ala Gly Ala Gly Ser
580 585 590

Gly Ala Gly Ala Gly Ser Gly Ala Gly Ala Gly Ser Gly Val Gly Val
595 600 605

Pro Gly Val Gly Val Pro Gly Val Gly Val Pro Gly Val Gly Val Pro
610 615 620

Gly Val Gly Val Pro Gly Val Gly Val Pro Gly Val Gly Val Pro Gly
625 630 635 640

Val Gly Val Pro Gly Ala Gly Ala Gly Ser Gly Ala Gly Ala Gly Ser

-continued

```
                645                 650                 655

Gly Ala Gly Ala Gly Ser Gly Ala Gly Ala Gly Ser Gly Ala Gly Ala
            660                 665                 670

Gly Ser Gly Ala Gly Ala Gly Ser Gly Ala Ala Gly Tyr Gly Ala Gly
        675                 680                 685

Ala Gly Ser Gly Ala Gly Ala Gly Ser Gly Ala Gly Ala Gly Ser Gly
    690                 695                 700

Ala Gly Ala Gly Ser Gly Ala Gly Ala Gly Ser Gly Val Gly Val Pro
705                 710                 715                 720

Gly Val Gly Val Pro Gly Val Gly Val Pro Gly Val Gly Val Pro Gly
                725                 730                 735

Val Gly Val Pro Gly Val Gly Val Pro Gly Val Gly Val Pro Gly Val
            740                 745                 750

Gly Val Pro Gly Ala Gly Ala Gly Ser Gly Ala Gly Ala Gly Ser Gly
        755                 760                 765

Ala Gly Ala Gly Ser Gly Ala Gly Ala Gly Ser Gly Ala Gly Ala Gly
    770                 775                 780

Ser Gly Ala Gly Ala Gly Ser Gly Ala Ala Gly Tyr Gly Ala Gly Ala
785                 790                 795                 800

Gly Ser Gly Ala Gly Ala Gly Ser Gly Ala Gly Ala Gly Ser Gly Ala
                805                 810                 815

Gly Ala Gly Ser Gly Ala Gly Ala Gly Ser Gly Val Gly Val Pro Gly
            820                 825                 830

Val Gly Val Pro Gly Val Gly Val Pro Gly Val Gly Val Pro Gly Val
        835                 840                 845

Gly Val Pro Gly Val Gly Val Pro Gly Val Gly Val Pro Gly Val Gly
    850                 855                 860

Val Pro Gly Ala Gly Ala Gly Ser Gly Ala Gly Ala Gly Ser Gly Ala
865                 870                 875                 880

Gly Ala Gly Ser Gly Ala Gly Ala Gly Ser Gly Ala Gly Ala Gly Ser
                885                 890                 895

Gly Ala Gly Ala Gly Ser Gly Ala Ala Gly Tyr Gly Ala Gly Ala Gly
            900                 905                 910

Ser Gly Ala Gly Ala Gly Ser Gly Ala Gly Ala Gly Ser Gly Ala Gly
        915                 920                 925

Ala Gly Ser Gly Ala Gly Ala Gly Ser Gly Val Gly Val Pro Gly Val
    930                 935                 940

Gly Val Pro Gly Val Gly Val Pro Gly Val Gly Val Pro Gly Val Gly
945                 950                 955                 960

Val Pro Gly Val Gly Val Pro Gly Val Gly Val Pro Gly Val Gly Val
                965                 970                 975

Pro Gly Ala Gly Ala Gly Ser Gly Ala Gly Ala Gly Ser Gly Ala Gly
            980                 985                 990

Ala Gly Ser Gly Ala Gly Ala Gly Ser Gly Ala Gly Ala Gly Ser Gly
        995                 1000                1005

Ala Gly Ala Gly Ser Gly Ala Ala Gly Tyr Gly Ala Gly Ala Gly Ser
    1010                1015                1020

Gly Ala Gly Ala Gly Ser Gly Ala Gly Ala Gly Ser Gly Ala Gly Ala
1025                1030                1035                1040

Gly Ser Gly Ala Gly Ala Gly Ser Gly Val Gly Val Pro Gly Val Gly
                1045                1050                1055

Val Pro Gly Val Gly Val Pro Gly Val Gly Val Pro Gly Val Gly Val
            1060                1065                1070
```

-continued

Pro Gly Val Gly Val Pro Gly Val Gly Val Pro Gly Val Gly Val Pro
1075 1080 1085

Gly Ala Gly Ala Gly Ser Gly Ala Gly Ala Gly Ser Gly Ala Gly Ala
1090 1095 1100

Gly Ser Gly Ala Gly Ala Gly Ser Gly Ala Gly Ala Gly Ser Gly Ala
1105 1110 1115 1120

Gly Ala Gly Ser Gly Ala Ala Gly Tyr Gly Ala Gly Ala Gly Ser Gly
1125 1130 1135

Ala Gly Ala Gly Ser Gly Ala Gly Ala Gly Ser Gly Ala Gly Ala Gly
1140 1145 1150

Ser Gly Ala Gly Ala Gly Ser Gly Val Gly Val Pro Gly Val Gly Val
1155 1160 1165

Pro Gly Val Gly Val Pro Gly Val Gly Val Pro Gly Val Gly Val Pro
1170 1175 1180

Gly Val Gly Val Pro Gly Val Gly Val Pro Gly Val Gly Val Pro Gly
1185 1190 1195 1200

Ala Gly Ala Gly Ser Gly Ala Gly Ala Gly Ser Gly Ala Gly Ala Gly
1205 1210 1215

Ser Gly Ala Gly Ala Gly Ser Gly Ala Gly Ala Gly Ser Gly Ala Gly
1220 1225 1230

Ala Gly Ser Gly Ala Ala Gly Tyr Gly Ala Gly Ala Gly Ser Gly Ala
1235 1240 1245

Gly Ala Gly Ser Gly Ala Gly Ala Gly Ser Gly Ala Gly Ala Gly Ser
1250 1255 1260

Gly Ala Gly Ala Gly Ser Gly Val Gly Val Pro Gly Val Gly Val Pro
1265 1270 1275 1280

Gly Val Gly Val Pro Gly Val Gly Val Pro Gly Val Gly Val Pro Gly
1285 1290 1295

Val Gly Val Pro Gly Val Gly Val Pro Gly Val Gly Val Pro Gly Ala
1300 1305 1310

Gly Ala Gly Ser Gly Ala Gly Ala Gly Ser Gly Ala Gly Ala Gly Ser
1315 1320 1325

Gly Ala Gly Ala Gly Ser Gly Ala Gly Ala Gly Ser Gly Ala Gly Ala
1330 1335 1340

Gly Ser Gly Ala Ala Gly Tyr Gly Ala Gly Ala Gly Ser Gly Ala Gly
1345 1350 1355 1360

Ala Gly Ser Gly Ala Gly Ala Gly Ser Gly Ala Gly Ala Gly Ser Gly
1365 1370 1375

Ala Gly Ala Gly Ser Gly Val Gly Val Pro Gly Val Gly Val Pro Gly
1380 1385 1390

Val Gly Val Pro Gly Val Gly Val Pro Gly Val Gly Val Pro Gly Val
1395 1400 1405

Gly Val Pro Gly Val Gly Val Pro Gly Val Gly Val Pro Gly Ala Gly
1410 1415 1420

Ala Gly Ser Gly Ala Gly Ala Gly Ser Gly Ala Gly Ala Gly Ser Gly
1425 1430 1435 1440

Ala Gly Ala Gly Ser Gly Ala Gly Ala Gly Ser Gly Ala Gly Ala Gly
1445 1450 1455

Ser Gly Ala Ala Gly Tyr Gly Ala Gly Ala Gly Ser Gly Ala Gly Ala
1460 1465 1470

Gly Ser Gly Ala Gly Ala Gly Ser Gly Ala Gly Ala Gly Ser Gly Ala
1475 1480 1485

Gly Ala Gly Ser Gly Val Gly Val Pro Gly Val Gly Val Pro Gly Val
1490 1495 1500

-continued

Gly Val Pro Gly Val Gly Val Pro Gly Val Gly Val Pro Gly Val Gly
1505 1510 1515 1520

Val Pro Gly Val Gly Val Pro Gly Val Gly Val Pro Gly Ala Gly Ala
1525 1530 1535

Gly Ser Gly Ala Gly Ala Gly Ser Gly Ala Gly Ala Gly Ser Gly Ala
1540 1545 1550

Gly Ala Gly Ser Gly Ala Gly Ala Gly Ser Gly Ala Gly Ala Gly Ser
1555 1560 1565

Gly Ala Ala Gly Tyr Gly Ala Gly Ala Gly Ser Gly Ala Gly Ala Gly
1570 1575 1580

Ser Gly Ala Gly Ala Gly Ser Gly Ala Gly Ala Gly Ser Gly Ala Gly
1585 1590 1595 1600

Ala Gly Ser Gly Val Gly Val Pro Gly Val Gly Val Pro Gly Val Gly
1605 1610 1615

Val Pro Gly Val Gly Val Pro Gly Val Gly Val Pro Gly Val Gly Val
1620 1625 1630

Pro Gly Val Gly Val Pro Gly Val Gly Val Pro Gly Ala Gly Ala Gly
1635 1640 1645

Ser Gly Ala Gly Ala Gly Ser Gly Ala Gly Ala Gly Ser Gly Ala Gly
1650 1655 1660

Ala Gly Ser Gly Ala Gly Ala Gly Ser Gly Ala Gly Ala Gly Ser Gly
1665 1670 1675 1680

Ala Ala Gly Tyr Gly Ala Gly Ala Gly Ser Gly Ala Gly Ala Gly Ser
1685 1690 1695

Gly Ala Gly Ala Gly Ser Gly Ala Gly Ala Gly Ser Gly Ala Gly Ala
1700 1705 1710

Gly Ser Gly Val Gly Val Pro Gly Val Gly Val Pro Gly Val Gly Val
1715 1720 1725

Pro Gly Val Gly Val Pro Gly Val Gly Val Pro Gly Val Gly Val Pro
1730 1735 1740

Gly Val Gly Val Pro Gly Val Gly Val Pro Gly Ala Gly Ala Gly Ser
1745 1750 1755 1760

Gly Ala Gly Ala Gly Ser Gly Ala Gly Ala Gly Ser Gly Ala Gly Ala
1765 1770 1775

Gly Ser Gly Ala Gly Ala Gly Ser Gly Ala Gly Ala Gly Ser Gly Ala
1780 1785 1790

Ala Gly Tyr Gly Ala Gly Ala Gly Ser Gly Ala Gly Ala Gly Ser Gly
1795 1800 1805

Ala Gly Ala Gly Ser Gly Ala Gly Ala Gly Ser Gly Ala Gly Ala Gly
1810 1815 1820

Ser Gly Val Gly Val Pro Gly Val Gly Val Pro Gly Val Gly Val Pro
1825 1830 1835 1840

Gly Val Gly Val Pro Gly Val Gly Val Pro Gly Val Gly Val Pro Gly
1845 1850 1855

Val Gly Val Pro Gly Val Gly Val Pro Gly Ala Gly Ala Gly Ser Gly
1860 1865 1870

Ala Gly Ala Gly Ser Gly Ala Gly Ala Gly Ser Gly Ala Gly Ala Gly
1875 1880 1885

Ser Gly Ala Gly Ala Gly Ser Gly Ala Gly Ala Gly Ser Gly Ala Ala
1890 1895 1900

Gly Tyr Gly Ala Gly Ala Gly Ser Gly Ala Gly Ala Gly Ser Gly Ala
1905 1910 1915 1920

Gly Ala Gly Ser Gly Ala Gly Ala Gly Ser Gly Ala Gly Ala Gly Ser

-continued 1925 1930 1935

Gly Val Gly Val Pro Gly Val Gly Val Pro Gly Val Gly Val Pro Gly
1940 1945 1950

Val Gly Val Pro Gly Val Gly Val Pro Gly Val Gly Val Pro Gly Val
1955 1960 1965

Gly Val Pro Gly Val Gly Val Pro Gly Ala Gly Ala Gly Ser Gly Ala
1970 1975 1980

Gly Ala Gly Ser Gly Ala Gly Ala Gly Ser Gly Ala Gly Ala Gly Ser
1985 1990 1995 2000

Gly Ala Gly Ala Gly Ser Gly Ala Gly Ala Gly Ser Gly Ala Ala Gly
2005 2010 2015

Tyr Gly Ala Gly Ala Gly Ser Gly Ala Gly Ala Gly Ser Gly Ala Gly
2020 2025 2030

Ala Met Asp Pro Gly Arg Tyr Gln Leu Ser Ala Gly Arg Tyr His Tyr
2035 2040 2045

Gln Leu Val Trp Cys Gln Lys
2050 2055

( 2 ) INFORMATION FOR SEQ ID NO:82:

( i ) SEQUENCE CHARACTERISTICS:
( A ) LENGTH: 2257 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:82:

Met Asp Pro Val Val Leu Gln Arg Arg Asp Trp Glu Asn Pro Gly Val
1 5 10 15

Thr Gln Leu Asn Arg Leu Ala Ala His Pro Pro Phe Ala Ser Asp Pro
20 25 30

Met Gly Ala Gly Ser Gly Ala Gly Ala Gly Ser Gly Ala Gly Ala Gly
35 40 45

Ser Gly Val Gly Val Pro Gly Val Gly Val Pro Gly Val Gly Val Pro
50 55 60

Gly Val Gly Val Pro Gly Val Gly Val Pro Gly Val Gly Val Pro Gly
65 70 75 80

Val Gly Val Pro Gly Val Gly Val Pro Gly Ala Gly Ala Gly Ser Gly
85 90 95

Ala Gly Ala Gly Ser Gly Ala Gly Ala Gly Ser Gly Ala Gly Ala Gly
100 105 110

Ser Gly Ala Gly Ala Gly Ser Gly Ala Gly Ala Gly Ser Gly Ala Gly
115 120 125

Ala Gly Ser Gly Ala Gly Ala Gly Ser Gly Val Gly Val Pro Gly Val
130 135 140

Gly Val Pro Gly Val Gly Val Pro Gly Val Gly Val Pro Gly Val Gly
145 150 155 160

Val Pro Gly Val Gly Val Pro Gly Val Gly Val Pro Gly Val Gly Val
165 170 175

Pro Gly Ala Gly Ala Gly Ser Gly Ala Gly Ala Gly Ser Gly Ala Gly
180 185 190

Ala Gly Ser Gly Ala Gly Ala Gly Ser Gly Ala Gly Ala Gly Ser Gly
195 200 205

Ala Gly Ala Gly Ser Gly Ala Gly Ala Gly Ser Gly Ala Gly Ala Gly
210 215 220

-continued

| | | | | | | | | | | | | | | | |
|---|---|---|---|---|---|---|---|---|---|---|---|---|---|---|---|
| Ser | Gly | Val | Gly | Val | Pro | Gly | Val | Gly | Val | Pro | Gly | Val | Gly | Val | Pro |
| 225 | | | | | 230 | | | | | 235 | | | | | 240 |
| Gly | Val | Gly | Val | Pro | Gly | Val | Gly | Val | Pro | Gly | Val | Gly | Val | Pro | Gly |
| | | | | 245 | | | | | 250 | | | | | 255 | |
| Val | Gly | Val | Pro | Gly | Val | Gly | Val | Pro | Gly | Ala | Gly | Ala | Gly | Ser | Gly |
| | | | 260 | | | | | 265 | | | | | 270 | | |
| Ala | Gly | Ala | Gly | Ser | Gly | Ala | Gly | Ala | Gly | Ser | Gly | Ala | Gly | Ala | Gly |
| | | 275 | | | | | 280 | | | | | 285 | | | |
| Ser | Gly | Ala | Gly | Ala | Gly | Ser | Gly | Ala | Gly | Ala | Gly | Ser | Gly | Ala | Gly |
| | 290 | | | | | 295 | | | | | 300 | | | | |
| Ala | Gly | Ser | Gly | Ala | Gly | Ala | Gly | Ser | Gly | Val | Gly | Val | Pro | Gly | Val |
| 305 | | | | | 310 | | | | | 315 | | | | | 320 |
| Gly | Val | Pro | Gly | Val | Gly | Val | Pro | Gly | Val | Gly | Val | Pro | Gly | Val | Gly |
| | | | | 325 | | | | | 330 | | | | | 335 | |
| Val | Pro | Gly | Val | Gly | Val | Pro | Gly | Val | Gly | Val | Pro | Gly | Val | Gly | Val |
| | | | 340 | | | | | 345 | | | | | 350 | | |
| Pro | Gly | Ala | Gly | Ala | Gly | Ser | Gly | Ala | Gly | Ala | Gly | Ser | Gly | Ala | Gly |
| | | 355 | | | | | 360 | | | | | 365 | | | |
| Ala | Gly | Ser | Gly | Ala | Gly | Ala | Gly | Ser | Gly | Ala | Gly | Ala | Gly | Ser | Gly |
| | 370 | | | | | 375 | | | | | 380 | | | | |
| Ala | Gly | Ala | Gly | Ser | Gly | Ala | Gly | Ala | Gly | Ser | Gly | Ala | Gly | Ala | Gly |
| 385 | | | | | 390 | | | | | 395 | | | | | 400 |
| Ser | Gly | Val | Gly | Val | Pro | Gly | Val | Gly | Val | Pro | Gly | Val | Gly | Val | Pro |
| | | | | 405 | | | | | 410 | | | | | 415 | |
| Gly | Val | Gly | Val | Pro | Gly | Val | Gly | Val | Pro | Gly | Val | Gly | Val | Pro | Gly |
| | | | 420 | | | | | 425 | | | | | 430 | | |
| Val | Gly | Val | Pro | Gly | Val | Gly | Val | Pro | Gly | Ala | Gly | Ala | Gly | Ser | Gly |
| | | 435 | | | | | 440 | | | | | 445 | | | |
| Ala | Gly | Ala | Gly | Ser | Gly | Ala | Gly | Ala | Gly | Ser | Gly | Ala | Gly | Ala | Gly |
| | 450 | | | | | 455 | | | | | 460 | | | | |
| Ser | Gly | Ala | Gly | Ala | Gly | Ser | Gly | Ala | Gly | Ala | Gly | Ser | Gly | Ala | Gly |
| 465 | | | | | 470 | | | | | 475 | | | | | 480 |
| Ala | Gly | Ser | Gly | Ala | Gly | Ala | Gly | Ser | Gly | Val | Gly | Val | Pro | Gly | Val |
| | | | | 485 | | | | | 490 | | | | | 495 | |
| Gly | Val | Pro | Gly | Val | Gly | Val | Pro | Gly | Val | Gly | Val | Pro | Gly | Val | Gly |
| | | | 500 | | | | | 505 | | | | | 510 | | |
| Val | Pro | Gly | Val | Gly | Val | Pro | Gly | Val | Gly | Val | Pro | Gly | Val | Gly | Val |
| | | 515 | | | | | 520 | | | | | 525 | | | |
| Pro | Gly | Ala | Gly | Ala | Gly | Ser | Gly | Ala | Gly | Ala | Gly | Ser | Gly | Ala | Gly |
| | 530 | | | | | 535 | | | | | 540 | | | | |
| Ala | Gly | Ser | Gly | Ala | Gly | Ala | Gly | Ser | Gly | Ala | Gly | Ala | Gly | Ser | Gly |
| 545 | | | | | 550 | | | | | 555 | | | | | 560 |
| Ala | Gly | Ala | Gly | Ser | Gly | Ala | Gly | Ala | Gly | Ser | Gly | Ala | Gly | Ala | Gly |
| | | | | 565 | | | | | 570 | | | | | 575 | |
| Ser | Gly | Val | Gly | Val | Pro | Gly | Val | Gly | Val | Pro | Gly | Val | Gly | Val | Pro |
| | | | 580 | | | | | 585 | | | | | 590 | | |
| Gly | Val | Gly | Val | Pro | Gly | Val | Gly | Val | Pro | Gly | Val | Gly | Val | Pro | Gly |
| | | 595 | | | | | 600 | | | | | 605 | | | |
| Val | Gly | Val | Pro | Gly | Val | Gly | Val | Pro | Gly | Ala | Gly | Ala | Gly | Ser | Gly |
| | 610 | | | | | 615 | | | | | 620 | | | | |
| Ala | Gly | Ala | Gly | Ser | Gly | Ala | Gly | Ala | Gly | Ser | Gly | Ala | Gly | Ala | Gly |
| 625 | | | | | 630 | | | | | 635 | | | | | 640 |
| Ser | Gly | Ala | Gly | Ala | Gly | Ser | Gly | Ala | Gly | Ala | Gly | Ser | Gly | Ala | Gly |

-continued 645 650 655

Ala Gly Ser Gly Ala Gly Ala Gly Ser Gly Val Gly Val Pro Gly Val
660 665 670

Gly Val Pro Gly Val Gly Val Pro Gly Val Gly Val Pro Gly Val Gly
675 680 685

Val Pro Gly Val Gly Val Pro Gly Val Gly Val Pro Gly Val Gly Val
690 695 700

Pro Gly Ala Gly Ala Gly Ser Gly Ala Gly Ala Gly Ser Gly Ala Gly
705 710 715 720

Ala Gly Ser Gly Ala Gly Ala Gly Ser Gly Ala Gly Ala Gly Ser Gly
725 730 735

Ala Gly Ala Gly Ser Gly Ala Gly Ala Gly Ser Gly Ala Gly Ala Gly
740 745 750

Ser Gly Val Gly Val Pro Gly Val Gly Val Pro Gly Val Gly Val Pro
755 760 765

Gly Val Gly Val Pro Gly Val Gly Val Pro Gly Val Gly Val Pro Gly
770 775 780

Val Gly Val Pro Gly Val Gly Val Pro Gly Ala Gly Ala Gly Ser Gly
785 790 795 800

Ala Gly Ala Gly Ser Gly Ala Gly Ala Gly Ser Gly Ala Gly Ala Gly
805 810 815

Ser Gly Ala Gly Ala Gly Ser Gly Ala Gly Ala Gly Ser Gly Ala Gly
820 825 830

Ala Gly Ser Gly Ala Gly Ala Gly Ser Gly Val Gly Val Pro Gly Val
835 840 845

Gly Val Pro Gly Val Gly Val Pro Gly Val Gly Val Pro Gly Val Gly
850 855 860

Val Pro Gly Val Gly Val Pro Gly Val Gly Val Pro Gly Val Gly Val
865 870 875 880

Pro Gly Ala Gly Ala Gly Ser Gly Ala Gly Ala Gly Ser Gly Ala Gly
885 890 895

Ala Gly Ser Gly Ala Gly Ala Gly Ser Gly Ala Gly Ala Gly Ser Gly
900 905 910

Ala Gly Ala Gly Ser Gly Ala Gly Ala Gly Ser Gly Ala Gly Ala Gly
915 920 925

Ser Gly Val Gly Val Pro Gly Val Gly Val Pro Gly Val Gly Val Pro
930 935 940

Gly Val Gly Val Pro Gly Val Gly Val Pro Gly Val Gly Val Pro Gly
945 950 955 960

Val Gly Val Pro Gly Val Gly Val Pro Gly Ala Gly Ala Gly Ser Gly
965 970 975

Ala Gly Ala Gly Ser Gly Ala Gly Ala Gly Ser Gly Ala Gly Ala Gly
980 985 990

Ser Gly Ala Gly Ala Gly Ser Gly Ala Gly Ala Gly Ser Gly Ala Gly
995 1000 1005

Ala Gly Ser Gly Ala Gly Ala Gly Ser Gly Val Gly Val Pro Gly Val
1010 1015 1020

Gly Val Pro Gly Val Gly Val Pro Gly Val Gly Val Pro Gly Val Gly
1025 1030 1035 1040

Val Pro Gly Val Gly Val Pro Gly Val Gly Val Pro Gly Val Gly Val
1045 1050 1055

Pro Gly Ala Gly Ala Gly Ser Gly Ala Gly Ala Gly Ser Gly Ala Gly
1060 1065 1070

-continued

Ala Gly Ser Gly Ala Gly Ala Gly Ser Gly Ala Gly Ala Gly Ser Gly
1075 1080 1085

Ala Gly Ala Gly Ser Gly Ala Gly Ala Gly Ser Gly Ala Gly Ala Gly
1090 1095 1100

Ser Gly Val Gly Val Pro Gly Val Gly Val Pro Gly Val Gly Val Pro
1105 1110 1115 1120

Gly Val Gly Val Pro Gly Val Gly Val Pro Gly Val Gly Val Pro Gly
1125 1130 1135

Val Gly Val Pro Gly Val Gly Val Pro Gly Ala Gly Ala Gly Ser Gly
1140 1145 1150

Ala Gly Ala Gly Ser Gly Ala Gly Ala Gly Ser Gly Ala Gly Ala Gly
1155 1160 1165

Ser Gly Ala Gly Ala Gly Ser Gly Ala Gly Ala Gly Ser Gly Ala Gly
1170 1175 1180

Ala Gly Ser Gly Ala Gly Ala Gly Ser Gly Val Gly Val Pro Gly Val
1185 1190 1195 1200

Gly Val Pro Gly Val Gly Val Pro Gly Val Gly Val Pro Gly Val Gly
1205 1210 1215

Val Pro Gly Val Gly Val Pro Gly Val Gly Val Pro Gly Val Gly Val
1220 1225 1230

Pro Gly Ala Gly Ala Gly Ser Gly Ala Gly Ala Gly Ser Gly Ala Gly
1235 1240 1245

Ala Gly Ser Gly Ala Gly Ala Gly Ser Gly Ala Gly Ala Gly Ser Gly
1250 1255 1260

Ala Gly Ala Gly Ser Gly Ala Gly Ala Gly Ser Gly Ala Gly Ala Gly
1265 1270 1275 1280

Ser Gly Val Gly Val Pro Gly Val Gly Val Pro Gly Val Gly Val Pro
1285 1290 1295

Gly Val Gly Val Pro Gly Val Gly Val Pro Gly Val Gly Val Pro Gly
1300 1305 1310

Val Gly Val Pro Gly Val Gly Val Pro Gly Ala Gly Ala Gly Ser Gly
1315 1320 1325

Ala Gly Ala Gly Ser Gly Ala Gly Ala Gly Ser Gly Ala Gly Ala Gly
1330 1335 1340

Ser Gly Ala Gly Ala Gly Ser Gly Ala Gly Ala Gly Ser Gly Ala Gly
1345 1350 1355 1360

Ala Gly Ser Gly Ala Gly Ala Gly Ser Gly Val Gly Val Pro Gly Val
1365 1370 1375

Gly Val Pro Gly Val Gly Val Pro Gly Val Gly Val Pro Gly Val Gly
1380 1385 1390

Val Pro Gly Val Gly Val Pro Gly Val Gly Val Pro Gly Val Gly Val
1395 1400 1405

Pro Gly Ala Gly Ala Gly Ser Gly Ala Gly Ala Gly Ser Gly Ala Gly
1410 1415 1420

Ala Gly Ser Gly Ala Gly Ala Gly Ser Gly Ala Gly Ala Gly Ser Gly
1425 1430 1435 1440

Ala Gly Ala Gly Ser Gly Ala Gly Ala Gly Ser Gly Ala Gly Ala Gly
1445 1450 1455

Ser Gly Val Gly Val Pro Gly Val Gly Val Pro Gly Val Gly Val Pro
1460 1465 1470

Gly Val Gly Val Pro Gly Val Gly Val Pro Gly Val Gly Val Pro Gly
1475 1480 1485

Val Gly Val Pro Gly Val Gly Val Pro Gly Ala Gly Ala Gly Ser Gly
1490 1495 1500

-continued

Ala Gly Ala Gly Ser Gly Ala Gly Ala Gly Ser Gly Ala Gly Ala Gly
1505 1510 1515 1520

Ser Gly Ala Gly Ala Gly Ser Gly Ala Gly Ala Gly Ser Gly Ala Gly
1525 1530 1535

Ala Gly Ser Gly Ala Gly Ala Gly Ser Gly Val Gly Val Pro Gly Val
1540 1545 1550

Gly Val Pro Gly Val Gly Val Pro Gly Val Gly Val Pro Gly Val Gly
1555 1560 1565

Val Pro Gly Val Gly Val Pro Gly Val Gly Val Pro Gly Val Gly Val
1570 1575 1580

Pro Gly Ala Gly Ala Gly Ser Gly Ala Gly Ala Gly Ser Gly Ala Gly
1585 1590 1595 1600

Ala Gly Ser Gly Ala Gly Ala Gly Ser Gly Ala Gly Ala Gly Ser Gly
1605 1610 1615

Ala Gly Ala Gly Ser Gly Ala Gly Ala Gly Ser Gly Ala Gly Ala Gly
1620 1625 1630

Ser Gly Val Gly Val Pro Gly Val Gly Val Pro Gly Val Gly Val Pro
1635 1640 1645

Gly Val Gly Val Pro Gly Val Gly Val Pro Gly Val Gly Val Pro Gly
1650 1655 1660

Val Gly Val Pro Gly Val Gly Val Pro Gly Ala Gly Ala Gly Ser Gly
1665 1670 1675 1680

Ala Gly Ala Gly Ser Gly Ala Gly Ala Gly Ser Gly Ala Gly Ala Gly
1685 1690 1695

Ser Gly Ala Gly Ala Gly Ser Gly Ala Gly Ala Gly Ser Gly Ala Gly
1700 1705 1710

Ala Gly Ser Gly Ala Gly Ala Gly Ser Gly Val Gly Val Pro Gly Val
1715 1720 1725

Gly Val Pro Gly Val Gly Val Pro Gly Val Gly Val Pro Gly Val Gly
1730 1735 1740

Val Pro Gly Val Gly Val Pro Gly Val Gly Val Pro Gly Val Gly Val
1745 1750 1755 1760

Pro Gly Ala Gly Ala Gly Ser Gly Ala Gly Ala Gly Ser Gly Ala Gly
1765 1770 1775

Ala Gly Ser Gly Ala Gly Ala Gly Ser Gly Ala Gly Ala Gly Ser Gly
1780 1785 1790

Ala Gly Ala Gly Ser Gly Ala Gly Ala Gly Ser Gly Ala Gly Ala Gly
1795 1800 1805

Ser Gly Val Gly Val Pro Gly Val Gly Val Pro Gly Val Gly Val Pro
1810 1815 1820

Gly Val Gly Val Pro Gly Val Gly Val Pro Gly Val Gly Val Pro Gly
1825 1830 1835 1840

Val Gly Val Pro Gly Val Gly Val Pro Gly Ala Gly Ala Gly Ser Gly
1845 1850 1855

Ala Gly Ala Gly Ser Gly Ala Gly Ala Gly Ser Gly Ala Gly Ala Gly
1860 1865 1870

Ser Gly Ala Gly Ala Gly Ser Gly Ala Gly Ala Gly Ser Gly Ala Gly
1875 1880 1885

Ala Gly Ser Gly Ala Gly Ala Gly Ser Gly Val Gly Val Pro Gly Val
1890 1895 1900

Gly Val Pro Gly Val Gly Val Pro Gly Val Gly Val Pro Gly Val Gly
1905 1910 1915 1920

Val Pro Gly Val Gly Val Pro Gly Val Gly Val Pro Gly Val Gly Val

-continued 1925 1930 1935

Pro Gly Ala Gly Ala Gly Ser Gly Ala Gly Ala Gly Ser Gly Ala Gly
1940 1945 1950

Ala Gly Ser Gly Ala Gly Ala Gly Ser Gly Ala Gly Ala Gly Ser Gly
1955 1960 1965

Ala Gly Ala Gly Ser Gly Ala Gly Ala Gly Ser Gly Ala Gly Ala Gly
1970 1975 1980

Ser Gly Val Gly Val Pro Gly Val Gly Val Pro Gly Val Gly Val Pro
1985 1990 1995 2000

Gly Val Gly Val Pro Gly Val Gly Val Pro Gly Val Gly Val Pro Gly
2005 2010 2015

Val Gly Val Pro Gly Val Gly Val Pro Gly Ala Gly Ala Gly Ser Gly
2020 2025 2030

Ala Gly Ala Gly Ser Gly Ala Gly Ala Gly Ser Gly Ala Gly Ala Gly
2035 2040 2045

Ser Gly Ala Gly Ala Gly Ser Gly Ala Gly Ala Gly Ser Gly Ala Gly
2050 2055 2060

Ala Gly Ser Gly Ala Gly Ala Gly Ser Gly Val Gly Val Pro Gly Val
2065 2070 2075 2080

Gly Val Pro Gly Val Gly Val Pro Gly Val Gly Val Pro Gly Val Gly
2085 2090 2095

Val Pro Gly Val Gly Val Pro Gly Val Gly Val Pro Gly Val Gly Val
2100 2105 2110

Pro Gly Ala Gly Ala Gly Ser Gly Ala Gly Ala Gly Ser Gly Ala Gly
2115 2120 2125

Ala Gly Ser Gly Ala Gly Ala Gly Ser Gly Ala Gly Ala Gly Ser Gly
2130 2135 2140

Ala Gly Ala Gly Ser Gly Ala Gly Ala Gly Ser Gly Ala Gly Ala Gly
2145 2150 2155 2160

Ser Gly Val Gly Val Pro Gly Val Gly Val Pro Gly Val Gly Val Pro
2165 2170 2175

Gly Val Gly Val Pro Gly Val Gly Val Pro Gly Val Gly Val Pro Gly
2180 2185 2190

Val Gly Val Pro Gly Val Gly Val Pro Gly Ala Gly Ala Gly Ser Gly
2195 2200 2205

Ala Gly Ala Gly Ser Gly Ala Gly Ala Gly Ser Gly Ala Gly Ala Gly
2210 2215 2220

Ser Gly Ala Gly Ala Gly Ser Gly Ala Gly Ala Met Asp Pro Gly Arg
2225 2230 2235 2240

Tyr Gln Leu Ser Ala Gly Arg Tyr His Tyr Gln Leu Val Trp Cys Gln
2245 2250 2255

Lys ( 2 ) INFORMATION FOR SEQ ID NO:83:

( i ) SEQUENCE CHARACTERISTICS:
( A ) LENGTH: 1101 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:83:

Met Asp Pro Val Val Leu Gln Arg Arg Asp Trp Glu Asn Pro Gly Val
1 5 10 15

-continued

Thr Gln Leu Asn Arg Leu Ala Ala His Pro Pro Phe Ala Ser Asp Pro
20 25 30

Met Gly Ala Gly Ser Gly Ala Gly Ala Gly Ser Gly Ala Gly Ala Gly
35 40 45

Ser Gly Ala Gly Ala Gly Ser Gly Ala Gly Ala Gly Ser Gly Ala Gly
50 55 60

Ala Gly Ser Gly Ala Gly Ala Gly Ser Gly Ala Gly Ala Gly Ser Gly
65 70 75 80

Ala Gly Ala Gly Ser Gly Ala Gly Ala Gly Ser Gly Ala Gly Ala Gly
85 90 95

Ser Gly Ala Gly Ala Gly Ser Gly Ala Gly Ala Gly Ser Gly Ala Gly
100 105 110

Ala Gly Ser Gly Ala Gly Ala Gly Ser Gly Ala Gly Ala Gly Ser Gly
115 120 125

Ala Gly Ala Gly Ser Gly Ala Gly Ala Gly Ser Gly Ala Gly Ala Gly
130 135 140

Ser Gly Ala Gly Ala Gly Ser Gly Ala Gly Ala Gly Ser Gly Ala Gly
145 150 155 160

Ala Gly Ser Gly Ala Gly Ala Gly Ser Gly Ala Gly Ala Gly Ser Gly
165 170 175

Ala Gly Ala Gly Ser Gly Ala Gly Ala Gly Ser Gly Ala Gly Ala Gly
180 185 190

Ser Gly Ala Gly Ala Gly Ser Gly Ala Gly Ala Gly Ser Gly Ala Gly
195 200 205

Ala Gly Ser Gly Ala Gly Ala Gly Ser Gly Ala Gly Ala Gly Ser Gly
210 215 220

Ala Gly Ala Gly Ser Gly Ala Gly Ala Gly Ser Gly Ala Gly Ala Gly
225 230 235 240

Ser Gly Ala Gly Ala Gly Ser Gly Ala Gly Ala Gly Ser Gly Ala Gly
245 250 255

Ala Gly Ser Gly Ala Gly Ala Gly Ser Gly Ala Gly Ala Gly Ser Gly
260 265 270

Ala Gly Ala Gly Ser Gly Ala Gly Ala Gly Ser Gly Ala Gly Ala Gly
275 280 285

Ser Gly Ala Gly Ala Gly Ser Gly Ala Gly Ala Gly Ser Gly Ala Gly
290 295 300

Ala Gly Ser Gly Ala Gly Ala Gly Ser Gly Ala Gly Ala Gly Ser Gly
305 310 315 320

Ala Gly Ala Gly Ser Gly Ala Gly Ala Gly Ser Gly Ala Gly Ala Gly
325 330 335

Ser Gly Ala Gly Ala Gly Ser Gly Ala Gly Ala Gly Ser Gly Ala Gly
340 345 350

Ala Gly Ser Gly Ala Gly Ala Gly Ser Gly Ala Gly Ala Gly Ser Gly
355 360 365

Ala Gly Ala Gly Ser Gly Ala Gly Ala Gly Ser Gly Ala Gly Ala Gly
370 375 380

Ser Gly Ala Gly Ala Gly Ser Gly Ala Gly Ala Gly Ser Gly Ala Gly
385 390 395 400

Ala Gly Ser Gly Ala Gly Ala Gly Ser Gly Ala Gly Ala Gly Ser Gly
405 410 415

Ala Gly Ala Gly Ser Gly Ala Gly Ala Gly Ser Gly Ala Gly Ala Gly
420 425 430

Ser Gly Ala Gly Ala Gly Ser Gly Ala Gly Ala Gly Ser Gly Ala Gly
435 440 445

-continued

Ala Gly Ser Gly Ala Gly Ala Gly Ser Gly Ala Gly Ala Gly Ser Gly
450 455 460

Ala Gly Ala Gly Ser Gly Ala Gly Ala Gly Ser Gly Ala Gly Ala Gly
465 470 475 480

Ser Gly Ala Gly Ala Gly Ser Gly Ala Gly Ala Gly Ser Gly Ala Gly
485 490 495

Ala Gly Ser Gly Ala Gly Ala Gly Ser Gly Ala Gly Ala Gly Ser Gly
500 505 510

Ala Gly Ala Gly Ser Gly Ala Gly Ala Gly Ser Gly Ala Gly Ala Gly
515 520 525

Ser Gly Ala Gly Ala Gly Ser Gly Ala Gly Ala Gly Ser Gly Ala Gly
530 535 540

Ala Gly Ser Gly Ala Gly Ala Gly Ser Gly Ala Gly Ala Gly Ser Gly
545 550 555 560

Ala Gly Ala Gly Ser Gly Ala Gly Ala Gly Ser Gly Ala Gly Ala Gly
565 570 575

Ser Gly Ala Gly Ala Gly Ser Gly Ala Gly Ala Gly Ser Gly Ala Gly
580 585 590

Ala Gly Ser Gly Ala Gly Ala Gly Ser Gly Ala Gly Ala Gly Ser Gly
595 600 605

Ala Gly Ala Gly Ser Gly Ala Gly Ala Gly Ser Gly Ala Gly Ala Gly
610 615 620

Ser Gly Ala Gly Ala Gly Ser Gly Ala Gly Ala Gly Ser Gly Ala Gly
625 630 635 640

Ala Gly Ser Gly Ala Gly Ala Gly Ser Gly Ala Gly Ala Gly Ser Gly
645 650 655

Ala Gly Ala Gly Ser Gly Ala Gly Ala Gly Ser Gly Ala Gly Ala Gly
660 665 670

Ser Gly Ala Gly Ala Gly Ser Gly Ala Gly Ala Gly Ser Gly Ala Gly
675 680 685

Ala Gly Ser Gly Ala Gly Ala Gly Ser Gly Ala Gly Ala Gly Ser Gly
690 695 700

Ala Gly Ala Gly Ser Gly Ala Gly Ala Gly Ser Gly Ala Gly Ala Gly
705 710 715 720

Ser Gly Ala Gly Ala Gly Ser Gly Ala Gly Ala Gly Ser Gly Ala Gly
725 730 735

Ala Gly Ser Gly Ala Gly Ala Gly Ser Gly Ala Gly Ala Gly Ser Gly
740 745 750

Ala Gly Ala Gly Ser Gly Ala Gly Ala Gly Ser Gly Ala Gly Ala Gly
755 760 765

Ser Gly Ala Gly Ala Gly Ser Gly Ala Gly Ala Gly Ser Gly Ala Gly
770 775 780

Ala Gly Ser Gly Ala Gly Ala Gly Ser Gly Ala Gly Ala Gly Ser Gly
785 790 795 800

Ala Gly Ala Gly Ser Gly Ala Gly Ala Gly Ser Gly Ala Gly Ala Gly
805 810 815

Ser Gly Ala Gly Ala Gly Ser Gly Ala Gly Ala Gly Ser Gly Ala Gly
820 825 830

Ala Gly Ser Gly Ala Gly Ala Gly Ser Gly Ala Gly Ala Gly Ser Gly
835 840 845

Ala Gly Ala Gly Ser Gly Ala Gly Ala Gly Ser Gly Ala Gly Ala Gly
850 855 860

Ser Gly Ala Gly Ala Gly Ser Gly Ala Gly Ala Gly Ser Gly Ala Gly

-continued 865 870 875 880

Ala Gly Ser Gly Ala Gly Ala Gly Ser Gly Ala Gly Ala Gly Ser Gly
885 890 895

Ala Gly Ala Gly Ser Gly Ala Gly Ala Gly Ser Gly Ala Gly Ala Gly
900 905 910

Ser Gly Ala Gly Ala Gly Ser Gly Ala Gly Ala Gly Ser Gly Ala Gly
915 920 925

Ala Gly Ser Gly Ala Gly Ala Gly Ser Gly Ala Gly Ala Gly Ser Gly
930 935 940

Ala Gly Ala Gly Ser Gly Ala Gly Ala Gly Ser Gly Ala Gly Ala Gly
945 950 955 960

Ser Gly Ala Gly Ala Gly Ser Gly Ala Gly Ala Gly Ser Gly Ala Gly
965 970 975

Ala Gly Ser Gly Ala Gly Ala Gly Ser Gly Ala Gly Ala Gly Ser Gly
980 985 990

Ala Gly Ala Gly Ser Gly Ala Gly Ala Gly Ser Gly Ala Gly Ala Gly
995 1000 1005

Ser Gly Ala Gly Ala Gly Ser Gly Ala Gly Ala Gly Ser Gly Ala Gly
1010 1015 1020

Ala Gly Ser Gly Ala Gly Ala Gly Ser Gly Ala Gly Ala Gly Ser Gly
1025 1030 1035 1040

Ala Gly Ala Gly Ser Gly Ala Gly Ala Gly Ser Gly Ala Gly Ala Gly
1045 1050 1055

Ser Gly Ala Gly Ala Gly Ser Gly Ala Gly Ala Gly Ser Gly Ala Gly
1060 1065 1070

Ala Gly Ser Gly Ala Gly Ala Met Asp Pro Gly Arg Tyr Gln Leu Ser
1075 1080 1085

Ala Gly Arg Tyr His Tyr Gln Leu Val Trp Cys Gln Lys
1090 1095 1100

( 2 ) INFORMATION FOR SEQ ID NO:84:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:84:

GTGACTGGCC GTGGTGATAG CCCGGCTAGC GCTGCA 36

( 2 ) INFORMATION FOR SEQ ID NO:85:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:85:

GCGCTAGCCG GGCTATCACC ACGGCCAGTC ACTGCA 36

( 2 ) INFORMATION FOR SEQ ID NO:86:

( i ) SEQUENCE CHARACTERISTICS:
( A ) LENGTH: 219 base pairs
( B ) TYPE: nucleic acid (C) STRANDEDNESS: single
(D) TOPOLOGY: linear (ii) MOLECULE TYPE: cDNA (xi) SEQUENCE DESCRIPTION: SEQ ID NO:86:

GGTGCCGGCA GCGGTGCAGG AGCCGGTTCT GGAGCTGGCG CGGGCTCTGG CGCGGGCGCA 60

GGATCCGGCG CAGGCGCTGG TTCTGGCGCA GGGGCAGGCT CTGGCGCAGG AGCGGGGTCT 120

GGAGCTGCAG TGACTGGCCG TGGTGATAGC CCGGCTAGCG CTGCAGGCTA TGGAGCTGGC 180

GCTGGCTCAG GTGCTGGAGC AGGAAGCGGA GCGGGTGCC 219

(2) INFORMATION FOR SEQ ID NO:87:

(i) SEQUENCE CHARACTERISTICS:
(A) LENGTH: 72 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:87:

Gly Ala Gly Ser Gly Ala Gly Ala Gly Ser Gly Ala Gly Ala Gly Ser
1 5 10 15

Gly Ala Gly Ala Gly Ser Gly Ala Gly Ala Gly Ser Gly Ala Gly Ala
20 25 30

Gly Ser Gly Ala Gly Ala Gly Ser Gly Ala Ala Val Thr Gly Arg Gly
35 40 45

Asp Ser Pro Ala Ser Ala Ala Gly Tyr Gly Ala Gly Ala Gly Ser Gly
50 55 60

Ala Gly Ala Gly Ser Gly Ala Gly
65 70

(2) INFORMATION FOR SEQ ID NO:88:

(i) SEQUENCE CHARACTERISTICS:
(A) LENGTH: 766 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:88:

Asp Pro Val Val Leu Gln Arg Arg Asp Trp Glu Asn Pro Gly Val Thr
1 5 10 15

Gln Leu Asn Arg Leu Ala Ala His Pro Pro Phe Ala Ser Asp Pro Met
20 25 30

Gly Ala Gly Ser Gly Ala Gly Ala Gly Ser Gly Ala Gly Ala Gly Ser
35 40 45

Gly Ala Gly Ala Gly Ser Gly Ala Gly Ala Gly Ser Gly Ala Gly Ala
50 55 60

Gly Ser Gly Ala Gly Ala Gly Ser Gly Ala Ala Val Thr Gly Arg Gly
65 70 75 80

Asp Ser Pro Ala Ser Ala Ala Gly Tyr Gly Ala Gly Ala Gly Ser Gly
85 90 95

Ala Gly Ala Gly Ser Gly Ala Gly Ala Gly Ser Gly Ala Gly Ala Gly
100 105 110

Ser Gly Ala Gly Ala Gly Ser Gly Ala Gly Ala Gly Ser Gly Ala Gly
115 120 125

-continued

```
Ala Gly Ser Gly Ala Gly Ala Gly Ser Gly Ala Gly Ala Gly Ser Gly
    130                 135                 140

Ala Ala Val Thr Gly Arg Gly Asp Ser Pro Ala Ser Ala Ala Gly Tyr
145                 150                 155                 160

Gly Ala Gly Ala Gly Ser Gly Ala Gly Ala Gly Ser Gly Ala Gly Ala
                165                 170                 175

Gly Ser Gly Ala Gly Ala Gly Ser Gly Ala Gly Ala Gly Ser Gly Ala
            180                 185                 190

Gly Ala Gly Ser Gly Ala Gly Ala Gly Ser Gly Ala Gly Ala Gly Ser
        195                 200                 205

Gly Ala Gly Ala Gly Ser Gly Ala Ala Val Thr Gly Arg Gly Asp Ser
    210                 215                 220

Pro Ala Ser Ala Ala Gly Tyr Gly Ala Gly Ala Gly Ser Gly Ala Gly
225                 230                 235                 240

Ala Gly Ser Gly Ala Gly Ala Gly Ser Gly Ala Gly Ala Gly Ser Gly
                245                 250                 255

Ala Gly Ala Gly Ser Gly Ala Gly Ala Gly Ser Gly Ala Gly Ala Gly
            260                 265                 270

Ser Gly Ala Gly Ala Gly Ser Gly Ala Gly Ala Gly Ser Gly Ala Ala
        275                 280                 285

Val Thr Gly Arg Gly Asp Ser Pro Ala Ser Ala Ala Gly Tyr Gly Ala
    290                 295                 300

Gly Ala Gly Ser Gly Ala Gly Ala Gly Ser Gly Ala Gly Ala Gly Ser
305                 310                 315                 320

Gly Ala Gly Ala Gly Ser Gly Ala Gly Ala Gly Ser Gly Ala Gly Ala
                325                 330                 335

Gly Ser Gly Ala Gly Ala Gly Ser Gly Ala Gly Ala Gly Ser Gly Ala
            340                 345                 350

Gly Ala Gly Ser Gly Ala Ala Val Thr Gly Arg Gly Asp Ser Pro Ala
        355                 360                 365

Ser Ala Ala Gly Tyr Gly Ala Gly Ala Gly Ser Gly Ala Gly Ala Gly
    370                 375                 380

Ser Gly Ala Gly Ala Gly Ser Gly Ala Gly Ala Gly Ser Gly Ala Gly
385                 390                 395                 400

Ala Gly Ser Gly Ala Gly Ala Gly Ser Gly Ala Gly Ala Gly Ser Gly
                405                 410                 415

Ala Gly Ala Gly Ser Gly Ala Gly Ala Gly Ser Gly Ala Ala Val Thr
            420                 425                 430

Gly Arg Gly Asp Ser Pro Ala Ser Ala Ala Gly Tyr Gly Ala Gly Ala
        435                 440                 445

Gly Ser Gly Ala Gly Ala Gly Ser Gly Ala Gly Ala Gly Ser Gly Ala
    450                 455                 460

Gly Ala Gly Ser Gly Ala Gly Ala Gly Ser Gly Ala Gly Ala Gly Ser
465                 470                 475                 480

Gly Ala Gly Ala Gly Ser Gly Ala Gly Ala Gly Ser Gly Ala Gly Ala
                485                 490                 495

Gly Ser Gly Ala Ala Val Thr Gly Arg Gly Asp Ser Pro Ala Ser Ala
            500                 505                 510

Ala Gly Tyr Gly Ala Gly Ala Gly Ser Gly Ala Gly Ala Gly Ser Gly
        515                 520                 525

Ala Gly Ala Gly Ser Gly Ala Gly Ala Gly Ser Gly Ala Gly Ala Gly
    530                 535                 540

Ser Gly Ala Gly Ala Gly Ser Gly Ala Gly Ala Gly Ser Gly Ala Gly
545                 550                 555                 560
```

-continued

| | | | | | | | | | | | | | | | |
|---|---|---|---|---|---|---|---|---|---|---|---|---|---|---|---|
| Ala | Gly | Ser | Gly | Ala | Gly | Ala | Gly | Ser | Gly | Ala | Ala | Val | Thr | Gly | Arg |
| | | | | 565 | | | | | 570 | | | | | 575 | |
| Gly | Asp | Ser | Pro | Ala | Ser | Ala | Ala | Gly | Tyr | Gly | Ala | Gly | Ala | Gly | Ser |
| | | | 580 | | | | | 585 | | | | | 590 | | |
| Gly | Ala | Gly | Ala | Gly | Ser | Gly | Ala | Gly | Ala | Gly | Ser | Gly | Ala | Gly | Ala |
| | | 595 | | | | | 600 | | | | | 605 | | | |
| Gly | Ser | Gly | Ala | Gly | Ala | Gly | Ser | Gly | Ala | Gly | Ala | Gly | Ser | Gly | Ala |
| | 610 | | | | | 615 | | | | | 620 | | | | |
| Gly | Ala | Gly | Ser | Gly | Ala | Gly | Ala | Gly | Ser | Gly | Ala | Gly | Ala | Gly | Ser |
| 625 | | | | | 630 | | | | | 635 | | | | | 640 |
| Gly | Ala | Ala | Val | Thr | Gly | Arg | Gly | Asp | Ser | Pro | Ala | Ser | Ala | Ala | Gly |
| | | | | 645 | | | | | 650 | | | | | 655 | |
| Tyr | Gly | Ala | Gly | Ala | Gly | Ser | Gly | Ala | Gly | Ala | Gly | Ser | Gly | Ala | Gly |
| | | | 660 | | | | | 665 | | | | | 670 | | |
| Ala | Gly | Ser | Gly | Ala | Gly | Ala | Gly | Ser | Gly | Ala | Gly | Ala | Gly | Ser | Gly |
| | | 675 | | | | | 680 | | | | | 685 | | | |
| Ala | Gly | Ala | Gly | Ser | Gly | Ala | Gly | Ala | Gly | Ser | Gly | Ala | Gly | Ala | Gly |
| | 690 | | | | | 695 | | | | | 700 | | | | |
| Ser | Gly | Ala | Gly | Ala | Gly | Ser | Gly | Ala | Ala | Val | Thr | Gly | Arg | Gly | Asp |
| 705 | | | | | 710 | | | | | 715 | | | | | 720 |
| Ser | Pro | Ala | Ser | Ala | Ala | Gly | Tyr | Gly | Ala | Gly | Ala | Gly | Ser | Gly | Ala |
| | | | | 725 | | | | | 730 | | | | | 735 | |
| Gly | Ala | Gly | Ser | Gly | Ala | Gly | Ala | Met | Asp | Pro | Gly | Arg | Tyr | Gln | Leu |
| | | | 740 | | | | | 745 | | | | | 750 | | |
| Ser | Ala | Gly | Arg | Tyr | His | Tyr | Gln | Leu | Val | Trp | Cys | Gln | Lys | | |
| | | 755 | | | | | 760 | | | | | 765 | | | |

( 2 ) INFORMATION FOR SEQ ID NO:89:

( i ) SEQUENCE CHARACTERISTICS:
( A ) LENGTH: 979 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:89:

| | | | | | | | | | | | | | | | |
|---|---|---|---|---|---|---|---|---|---|---|---|---|---|---|---|
| Asp | Pro | Val | Val | Leu | Gln | Arg | Arg | Asp | Trp | Glu | Asn | Pro | Gly | Val | Thr |
| 1 | | | | 5 | | | | | 10 | | | | | 15 | |
| Gln | Leu | Asn | Arg | Leu | Ala | Ala | His | Pro | Pro | Phe | Ala | Ser | Asp | Pro | Met |
| | | | 20 | | | | | 25 | | | | | 30 | | |
| Gly | Ala | Gly | Ser | Gly | Ala | Gly | Ala | Gly | Ser | Gly | Ala | Gly | Ala | Gly | Ser |
| | | 35 | | | | | 40 | | | | | 45 | | | |
| Gly | Ala | Gly | Ala | Gly | Ser | Gly | Ala | Gly | Ala | Gly | Ser | Gly | Ala | Gly | Ala |
| | 50 | | | | | 55 | | | | | 60 | | | | |
| Gly | Ser | Gly | Ala | Gly | Ala | Gly | Ser | Gly | Ala | Ala | Val | Thr | Gly | Arg | Gly |
| 65 | | | | | 70 | | | | | 75 | | | | | 80 |
| Asp | Ser | Pro | Ala | Ser | Ala | Ala | Gly | Tyr | Gly | Ala | Gly | Ala | Gly | Ser | Gly |
| | | | | 85 | | | | | 90 | | | | | 95 | |
| Ala | Gly | Ala | Gly | Ser | Gly | Ala | Gly | Ala | Gly | Ser | Gly | Ala | Gly | Ala | Gly |
| | | | 100 | | | | | 105 | | | | | 110 | | |
| Ser | Gly | Ala | Gly | Ala | Gly | Ser | Gly | Ala | Gly | Ala | Gly | Ser | Gly | Ala | Gly |
| | | 115 | | | | | 120 | | | | | 125 | | | |
| Ala | Gly | Ser | Gly | Ala | Gly | Ala | Gly | Ser | Gly | Ala | Gly | Ala | Gly | Ser | Gly |
| | 130 | | | | | 135 | | | | | 140 | | | | |

-continued

| | | | | | | | | | | | | | | | |
|---|---|---|---|---|---|---|---|---|---|---|---|---|---|---|---|
| Ala | Ala | Val | Thr | Gly | Arg | Gly | Asp | Ser | Pro | Ala | Ser | Ala | Ala | Gly | Tyr |
| 145 | | | | | 150 | | | | | 155 | | | | | 160 |
| Gly | Ala | Gly | Ala | Gly | Ser | Gly | Ala | Gly | Ala | Gly | Ser | Gly | Ala | Gly | Ala |
| | | | | 165 | | | | | 170 | | | | | 175 | |
| Gly | Ser | Gly | Ala | Gly | Ala | Gly | Ser | Gly | Ala | Gly | Ala | Gly | Ser | Gly | Ala |
| | | | 180 | | | | | 185 | | | | | 190 | | |
| Gly | Ala | Gly | Ser | Gly | Ala | Gly | Ala | Gly | Ser | Gly | Ala | Gly | Ala | Gly | Ser |
| | | 195 | | | | | 200 | | | | | 205 | | | |
| Gly | Ala | Gly | Ala | Gly | Ser | Gly | Ala | Ala | Val | Thr | Gly | Arg | Gly | Asp | Ser |
| | 210 | | | | | 215 | | | | | 220 | | | | |
| Pro | Ala | Ser | Ala | Ala | Gly | Tyr | Gly | Ala | Gly | Ala | Gly | Ser | Gly | Ala | Gly |
| 225 | | | | | 230 | | | | | 235 | | | | | 240 |
| Ala | Gly | Ser | Gly | Ala | Gly | Ala | Gly | Ser | Gly | Ala | Gly | Ala | Gly | Ser | Gly |
| | | | | 245 | | | | | 250 | | | | | 255 | |
| Ala | Gly | Ala | Gly | Ser | Gly | Ala | Gly | Ala | Gly | Ser | Gly | Ala | Gly | Ala | Gly |
| | | | 260 | | | | | 265 | | | | | 270 | | |
| Ser | Gly | Ala | Gly | Ala | Gly | Ser | Gly | Ala | Gly | Ala | Gly | Ser | Gly | Ala | Ala |
| | | 275 | | | | | 280 | | | | | 285 | | | |
| Val | Thr | Gly | Arg | Gly | Asp | Ser | Pro | Ala | Ser | Ala | Ala | Gly | Tyr | Gly | Ala |
| | 290 | | | | | 295 | | | | | 300 | | | | |
| Gly | Ala | Gly | Ser | Gly | Ala | Gly | Ala | Gly | Ser | Gly | Ala | Gly | Ala | Gly | Ser |
| 305 | | | | | 310 | | | | | 315 | | | | | 320 |
| Gly | Ala | Gly | Ala | Gly | Ser | Gly | Ala | Gly | Ala | Gly | Ser | Gly | Ala | Gly | Ala |
| | | | | 325 | | | | | 330 | | | | | 335 | |
| Gly | Ser | Gly | Ala | Gly | Ala | Gly | Ser | Gly | Ala | Gly | Ala | Gly | Ser | Gly | Ala |
| | | | 340 | | | | | 345 | | | | | 350 | | |
| Gly | Ala | Gly | Ser | Gly | Ala | Ala | Val | Thr | Gly | Arg | Gly | Asp | Ser | Pro | Ala |
| | | 355 | | | | | 360 | | | | | 365 | | | |
| Ser | Ala | Ala | Gly | Tyr | Gly | Ala | Gly | Ala | Gly | Ser | Gly | Ala | Gly | Ala | Gly |
| | 370 | | | | | 375 | | | | | 380 | | | | |
| Ser | Gly | Ala | Gly | Ala | Gly | Ser | Gly | Ala | Gly | Ala | Gly | Ser | Gly | Ala | Gly |
| 385 | | | | | 390 | | | | | 395 | | | | | 400 |
| Ala | Gly | Ser | Gly | Ala | Gly | Ala | Gly | Ser | Gly | Ala | Gly | Ala | Gly | Ser | Gly |
| | | | | 405 | | | | | 410 | | | | | 415 | |
| Ala | Gly | Ala | Gly | Ser | Gly | Ala | Gly | Ala | Gly | Ser | Gly | Ala | Ala | Val | Thr |
| | | | 420 | | | | | 425 | | | | | 430 | | |
| Gly | Arg | Gly | Asp | Ser | Pro | Ala | Ser | Ala | Ala | Gly | Tyr | Gly | Ala | Gly | Ala |
| | | 435 | | | | | 440 | | | | | 445 | | | |
| Gly | Ser | Gly | Ala | Gly | Ala | Gly | Ser | Gly | Ala | Gly | Ala | Gly | Ser | Gly | Ala |
| | 450 | | | | | 455 | | | | | 460 | | | | |
| Gly | Ala | Gly | Ser | Gly | Ala | Gly | Ala | Gly | Ser | Gly | Ala | Gly | Ala | Gly | Ser |
| 465 | | | | | 470 | | | | | 475 | | | | | 480 |
| Gly | Ala | Gly | Ala | Gly | Ser | Gly | Ala | Gly | Ala | Gly | Ser | Gly | Ala | Gly | Ala |
| | | | | 485 | | | | | 490 | | | | | 495 | |
| Gly | Ser | Gly | Ala | Ala | Val | Thr | Gly | Arg | Gly | Asp | Ser | Pro | Ala | Ser | Ala |
| | | | 500 | | | | | 505 | | | | | 510 | | |
| Ala | Gly | Tyr | Gly | Ala | Gly | Ala | Gly | Ser | Gly | Ala | Gly | Ala | Gly | Ser | Gly |
| | | 515 | | | | | 520 | | | | | 525 | | | |
| Ala | Gly | Ala | Gly | Ser | Gly | Ala | Gly | Ala | Gly | Ser | Gly | Ala | Gly | Ala | Gly |
| | 530 | | | | | 535 | | | | | 540 | | | | |
| Ser | Gly | Ala | Gly | Ala | Gly | Ser | Gly | Ala | Gly | Ala | Gly | Ser | Gly | Ala | Gly |
| 545 | | | | | 550 | | | | | 555 | | | | | 560 |
| Ala | Gly | Ser | Gly | Ala | Gly | Ala | Gly | Ser | Gly | Ala | Ala | Val | Thr | Gly | Arg |
| | | | | 565 | | | | | 570 | | | | | 575 | |

-continued

Gly Asp Ser Pro Ala Ser Ala Ala Gly Tyr Gly Ala Gly Ala Gly Ser
580 585 590

Gly Ala Gly Ala Gly Ser Gly Ala Gly Ala Gly Ser Gly Ala Gly Ala
595 600 605

Gly Ser Gly Ala Gly Ala Gly Ser Gly Ala Gly Ala Gly Ser Gly Ala
610 615 620

Gly Ala Gly Ser Gly Ala Gly Ala Gly Ser Gly Ala Gly Ala Gly Ser
625 630 635 640

Gly Ala Ala Val Thr Gly Arg Gly Asp Ser Pro Ala Ser Ala Ala Gly
645 650 655

Tyr Gly Ala Gly Ala Gly Ser Gly Ala Gly Ala Gly Ser Gly Ala Gly
660 665 670

Ala Gly Ser Gly Ala Gly Ala Gly Ser Gly Ala Gly Ala Gly Ser Gly
675 680 685

Ala Gly Ala Gly Ser Gly Ala Gly Ala Gly Ser Gly Ala Gly Ala Gly
690 695 700

Ser Gly Ala Gly Ala Gly Ser Gly Ala Ala Val Thr Gly Arg Gly Asp
705 710 715 720

Ser Pro Ala Ser Ala Ala Gly Tyr Gly Ala Gly Ala Gly Ser Gly Ala
725 730 735

Gly Ala Gly Ser Gly Ala Gly Ala Gly Ser Gly Ala Gly Ala Gly Ser
740 745 750

Gly Ala Gly Ala Gly Ser Gly Ala Gly Ala Gly Ser Gly Ala Gly Ala
755 760 765

Gly Ser Gly Ala Gly Ala Gly Ser Gly Ala Gly Ala Gly Ser Gly Ala
770 775 780

Ala Val Thr Gly Arg Gly Asp Ser Pro Ala Ser Ala Ala Gly Tyr Gly
785 790 795 800

Ala Gly Ala Gly Ser Gly Ala Gly Ala Gly Ser Gly Ala Gly Ala Gly
805 810 815

Ser Gly Ala Gly Ala Gly Ser Gly Ala Gly Ala Gly Ser Gly Ala Gly
820 825 830

Ala Gly Ser Gly Ala Gly Ala Gly Ser Gly Ala Gly Ala Gly Ser Gly
835 840 845

Ala Gly Ala Gly Ser Gly Ala Ala Val Thr Gly Arg Gly Asp Ser Pro
850 855 860

Ala Ser Ala Ala Gly Tyr Gly Ala Gly Ala Gly Ser Gly Ala Gly Ala
865 870 875 880

Gly Ser Gly Ala Gly Ala Gly Ser Gly Ala Gly Ala Gly Ser Gly Ala
885 890 895

Gly Ala Gly Ser Gly Ala Gly Ala Gly Ser Gly Ala Gly Ala Gly Ser
900 905 910

Gly Ala Gly Ala Gly Ser Gly Ala Gly Ala Gly Ser Gly Ala Ala Val
915 920 925

Thr Gly Arg Gly Asp Ser Pro Ala Ser Ala Ala Gly Tyr Gly Ala Gly
930 935 940

Ala Gly Ser Gly Ala Gly Ala Gly Ser Gly Ala Gly Ala Met Asp Pro
945 950 955 960

Gly Arg Tyr Gln Leu Ser Ala Gly Arg Tyr His Tyr Gln Leu Val Trp
965 970 975

Cys Gln Lys ( 2 ) INFORMATION FOR SEQ ID NO:90:

-continued ( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:90:

GTGCTGCGGA TGCTCGAGAT GGTGCATGCA TGTACATCCG AGTACTTCGA T 51

( 2 ) INFORMATION FOR SEQ ID NO:91:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:91:

ATCGAAGTAC TCGGATGTAC ATGCATGCAC CATCTCGAGC ATCCGCA 47

( 2 ) INFORMATION FOR SEQ ID NO:92:

( i ) SEQUENCE CHARACTERISTICS:
( A ) LENGTH: 24 base pairs
( B ) TYPE: nucliec acid
( C ) STRANDEDNESS: single
( D ) TOPOLOGY: linear ( i i ) MOLECULE TYPE: cDNA ( x i ) SEQUENCE DESCRIPTION: SEQ ID NO:92:

CTACATGTGT TACACATCCC GTGC 24

( 2 ) INFORMATION FOR SEQ ID NO:93:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:93:

GCACGGGATG TGTAACACAT GTAGAGCC 28

( 2 ) INFORMATION FOR SEQ ID NO:94:

( i ) SEQUENCE CHARACTERISTICS:
( A ) LENGTH: 1011 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:94:

Met Asp Pro Val Val Leu Gln Arg Arg Asp Trp Glu Asn Pro Gly Val
1 5 10 15

Thr Gln Leu Asn Arg Leu Ala Ala His Pro Pro Phe Ala Ser Asp Pro
20 25 30

Met Gly Ala Gly Ser Gly Ala Gly Ala Gly Ser Gly Ala Gly Ala Gly
35 40 45

-continued

Ser Gly Val Gly Val Pro Gly Val Gly Val Pro Gly Val Gly Val Pro
50 55 60

Gly Val Gly Val Pro Gly Val Gly Val Pro Gly Val Gly Val Pro Gly
65 70 75 80

Val Gly Val Pro Gly Val Gly Val Pro Gly Ala Gly Ala Gly Ser Gly
85 90 95

Ala Gly Ala Gly Ser Gly Ala Gly Ala Gly Ser Gly Ala Gly Ala Gly
100 105 110

Ser Gly Ala Gly Ala Gly Ser Gly Ala Gly Ala Gly Ser Gly Ala Gly
115 120 125

Ala Gly Ser Gly Ala Gly Ala Gly Ser Gly Ala Gly Ala Gly Ser Gly
130 135 140

Ala Gly Ala Gly Ser Gly Ala Gly Ala Gly Ser Gly Ala Gly Ala Gly
145 150 155 160

Ser Gly Ala Ala Val Thr Gly Arg Gly Asp Ser Pro Ala Ser Ala Ala
165 170 175

Gly Tyr Gly Ala Gly Ala Gly Ser Gly Ala Gly Ala Gly Ser Gly Ala
180 185 190

Gly Ala Gly Ser Gly Ala Gly Ala Gly Ser Gly Ala Gly Ala Gly Ser
195 200 205

Gly Val Gly Val Pro Gly Val Gly Val Pro Gly Val Gly Val Pro Gly
210 215 220

Val Gly Val Pro Gly Val Gly Val Pro Gly Val Gly Val Pro Gly Val
225 230 235 240

Gly Val Pro Gly Val Gly Val Pro Gly Ala Gly Ala Gly Ser Gly Ala
245 250 255

Gly Ala Gly Ser Gly Ala Gly Ala Gly Ser Gly Ala Gly Ala Gly Ser
260 265 270

Gly Ala Gly Ala Gly Ser Gly Ala Gly Ala Gly Ser Gly Ala Gly Ala
275 280 285

Gly Ser Gly Ala Gly Ala Gly Ser Gly Ala Gly Ala Gly Ser Gly Ala
290 295 300

Gly Ala Gly Ser Gly Ala Gly Ala Gly Ser Gly Ala Gly Ala Gly Ser
305 310 315 320

Gly Ala Ala Val Thr Gly Arg Gly Asp Ser Pro Ala Ser Ala Ala Gly
325 330 335

Tyr Gly Ala Gly Ala Gly Ser Gly Ala Gly Ala Gly Ser Gly Ala Gly
340 345 350

Ala Gly Ser Gly Ala Gly Ala Gly Ser Gly Ala Gly Ala Gly Ser Gly
355 360 365

Val Gly Val Pro Gly Val Gly Val Pro Gly Val Gly Val Pro Gly Val
370 375 380

Gly Val Pro Gly Val Gly Val Pro Gly Val Gly Val Pro Gly Val Gly
385 390 395 400

Val Pro Gly Val Gly Val Pro Gly Ala Gly Ala Gly Ser Gly Ala Gly
405 410 415

Ala Gly Ser Gly Ala Gly Ala Gly Ser Gly Ala Gly Ala Gly Ser Gly
420 425 430

Ala Gly Ala Gly Ser Gly Ala Gly Ala Gly Ser Gly Ala Gly Ala Gly
435 440 445

Ser Gly Ala Gly Ala Gly Ser Gly Ala Gly Ala Gly Ser Gly Ala Gly
450 455 460

Ala Gly Ser Gly Ala Gly Ala Gly Ser Gly Ala Gly Ala Gly Ser Gly
465 470 475 480

-continued

Ala Ala Val Thr Gly Arg Gly Asp Ser Pro Ala Ser Ala Ala Gly Tyr
485 490 495

Gly Ala Gly Ala Gly Ser Gly Ala Gly Ala Gly Ser Gly Ala Gly Ala
500 505 510

Gly Ser Gly Ala Gly Ala Gly Ser Gly Ala Gly Ala Gly Ser Gly Val
515 520 525

Gly Val Pro Gly Val Gly Val Pro Gly Val Gly Val Pro Gly Val Gly
530 535 540

Val Pro Gly Val Gly Val Pro Gly Val Gly Val Pro Gly Val Gly Val
545 550 555 560

Pro Gly Val Gly Val Pro Gly Ala Gly Ala Gly Ser Gly Ala Gly Ala
565 570 575

Gly Ser Gly Ala Gly Ala Gly Ser Gly Ala Gly Ala Gly Ser Gly Ala
580 585 590

Gly Ala Gly Ser Gly Ala Gly Ala Gly Ser Gly Ala Gly Ala Gly Ser
595 600 605

Gly Ala Gly Ala Gly Ser Gly Ala Gly Ala Gly Ser Gly Ala Gly Ala
610 615 620

Gly Ser Gly Ala Gly Ala Gly Ser Gly Ala Gly Ala Gly Ser Gly Ala
625 630 635 640

Ala Val Thr Gly Arg Gly Asp Ser Pro Ala Ser Ala Ala Gly Tyr Gly
645 650 655

Ala Gly Ala Gly Ser Gly Ala Gly Ala Gly Ser Gly Ala Gly Ala Gly
660 665 670

Ser Gly Ala Gly Ala Gly Ser Gly Ala Gly Ala Gly Ser Gly Val Gly
675 680 685

Val Pro Gly Val Gly Val Pro Gly Val Gly Val Pro Gly Val Gly Val
690 695 700

Pro Gly Val Gly Val Pro Gly Val Gly Val Pro Gly Val Gly Val Pro
705 710 715 720

Gly Val Gly Val Pro Gly Ala Gly Ala Gly Ser Gly Ala Gly Ala Gly
725 730 735

Ser Gly Ala Gly Ala Gly Ser Gly Ala Gly Ala Gly Ser Gly Ala Gly
740 745 750

Ala Gly Ser Gly Ala Gly Ala Gly Ser Gly Ala Gly Ala Gly Ser Gly
755 760 765

Ala Gly Ala Gly Ser Gly Ala Gly Ala Gly Ser Gly Ala Gly Ala Gly
770 775 780

Ser Gly Ala Gly Ala Gly Ser Gly Ala Gly Ala Gly Ser Gly Ala Ala
785 790 795 800

Val Thr Gly Arg Gly Asp Ser Pro Ala Ser Ala Ala Gly Tyr Gly Ala
805 810 815

Gly Ala Gly Ser Gly Ala Gly Ala Gly Ser Gly Ala Gly Ala Gly Ser
820 825 830

Gly Ala Gly Ala Gly Ser Gly Ala Gly Ala Gly Ser Gly Val Gly Val
835 840 845

Pro Gly Val Gly Val Pro Gly Val Gly Val Pro Gly Val Gly Val Pro
850 855 860

Gly Val Gly Val Pro Gly Val Gly Val Pro Gly Val Gly Val Pro Gly
865 870 875 880

Val Gly Val Pro Gly Ala Gly Ala Gly Ser Gly Ala Gly Ala Gly Ser
885 890 895

Gly Ala Gly Ala Gly Ser Gly Ala Gly Ala Gly Ser Gly Ala Gly Ala

-continued

| | | | | | | | | | | | | | | | |
|---|---|---|---|---|---|---|---|---|---|---|---|---|---|---|---|
| | | | 900 | | | | | | 905 | | | | | 910 | |
| Gly | Ser | Gly | Ala | Gly | Ala | Gly | Ser | Gly | Ala | Gly | Ala | Gly | Ser | Gly | Ala |
| | | 915 | | | | | 920 | | | | | 925 | | | |
| Gly | Ala | Gly | Ser | Gly | Ala | Gly | Ala | Gly | Ser | Gly | Ala | Gly | Ala | Gly | Ser |
| | 930 | | | | | 935 | | | | | 940 | | | | |
| Gly | Ala | Gly | Ala | Gly | Ser | Gly | Ala | Gly | Ala | Gly | Ser | Gly | Ala | Ala | Val |
| 945 | | | | | 950 | | | | | 955 | | | | | 960 |
| Thr | Gly | Arg | Gly | Asp | Ser | Pro | Ala | Ser | Ala | Ala | Gly | Tyr | Gly | Ala | Gly |
| | | | | 965 | | | | | 970 | | | | | 975 | |
| Ala | Gly | Ser | Gly | Ala | Gly | Ala | Gly | Ser | Gly | Ala | Gly | Ala | Met | Asp | Pro |
| | | | 980 | | | | | 985 | | | | | 990 | | |
| Gly | Arg | Tyr | Gln | Leu | Ser | Ala | Gly | Arg | Tyr | His | Tyr | Gln | Leu | Val | Trp |
| | | 995 | | | | | 1000 | | | | | 1005 | | | |
| Cys | Gln | Lys | | | | | | | | | | | | | |
| | 1010 | | | | | | | | | | | | | | |

( 2 ) INFORMATION FOR SEQ ID NO:95:

( i ) SEQUENCE CHARACTERISTICS:
( A ) LENGTH: 63 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:95:

GCTATGTTTA AACCACGTGT TCGCGATCCG GGTGCCGATC CAGGCCTGCG ATATCAGTAC 60

GTA 63

( 2 ) INFORMATION FOR SEQ ID NO:96:

( i ) SEQUENCE CHARACTERISTICS:
( A ) LENGTH: 63 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:96:

TACGTACTGA TATCGCAGGC CTGGATCGGC ACCCGGATCG CGAACACGTC CTTTAAACAT 60

AGC 63

( 2 ) INFORMATION FOR SEQ ID NO:97:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:97:

| | | | | | | | | | | | | | | | |
|---|---|---|---|---|---|---|---|---|---|---|---|---|---|---|---|
| Ala | Met | Phe | Lys | Pro | Arg | Val | Arg | Asp | Pro | Gly | Ala | Asp | Pro | Gly | Leu |
| 1 | | | | 5 | | | | | 10 | | | | | 15 | |
| Arg | Tyr | Gln | Tyr | Val | | | | | | | | | | | |
| | | | 20 | | | | | | | | | | | | |

( 2 ) INFORMATION FOR SEQ ID NO:98:

( i ) SEQUENCE CHARACTERISTICS:

( A ) LENGTH: 226 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:98:

ATGGCAGCGA AAGGGGACCG GTGCCCCGGG TACTCCTGGT CCACAAGGTC TGCCGGGAAG 60

CCCAGGGGCT CCGGGTACTC CAGGTCCGCA AGGCCTGCCG GGTTCACCGG GTGCTCCGGG 120

AACTCCTGGC CCGCAGGGCT TGCCGGGATC CCCAGGTGCA CCAGGAACGC CGGGACCTCA 180

GGGTCTTCCG GGTAGCCCTG GTGCCTTTCC GCTAAAGTCC TGCCGT 226

( 2 ) INFORMATION FOR SEQ ID NO:99:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:99:

AAGAAGGAGA TATCATATGG CAGCGAAAGG GGACC 35

( 2 ) INFORMATION FOR SEQ ID NO:100:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:100:

AAAGCGATTT CAGGACGGCA TTAAATTTCT AGACGC 36

( 2 ) INFORMATION FOR SEQ ID NO:101:

( i ) SEQUENCE CHARACTERISTICS:
( A ) LENGTH: 186 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:101:

GGTGCCCCGG GTACTCCTGG TCCACAAGGT CTGCCGGGAA GCCCAGGGGC TCCGGGTACT 60

CCAGGTCCGC AAGGCCTGCC GGGTTCACCG GGTGCTCCGG GAACTCCTGG CCCGCAGGGC 120

TTGCCGGGAT CCCCAGGTGC ACCAGGAACG CCGGGACCTC AGGGTCTTCC GGGTAGCCCT 180

GGTGCC 186

( 2 ) INFORMATION FOR SEQ ID NO:102:

( i ) SEQUENCE CHARACTERISTICS:
( A ) LENGTH: 61 amino acids
( B ) TYPE: amino acid
( C ) STRANDEDNESS: single
( D ) TOPOLOGY: linear ( i i ) MOLECULE TYPE: peptide ( i x ) FEATURE:

-continued ( A ) NAME/KEY: Peptide
( B ) LOCATION: 1..61
( D ) OTHER INFORMATION: /note= "X = G or A"

( x i ) SEQUENCE DESCRIPTION: SEQ ID NO:102:

Gly Ala Pro Gly Thr Pro Gly Pro Gln Gly Leu Pro Gly Ser Pro Gly
1 5 10 15

Ala Pro Gly Thr Pro Gly Pro Gln Gly Leu Pro Gly Ser Pro Gly Ala
20 25 30

Pro Gly Thr Pro Gly Pro Gln Gly Leu Pro Gly Ser Pro Gly Ala Pro
35 40 45

Gly Thr Pro Gly Pro Gln Gly Leu Pro Gly Ser Pro Xaa
50 55 60

( 2 ) INFORMATION FOR SEQ ID NO:103:

( i ) SEQUENCE CHARACTERISTICS:
( A ) LENGTH: 837 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:103:

Met Asp Pro Val Val Leu Gln Arg Arg Asp Trp Glu Asn Pro Gly Val
1 5 10 15

Thr Gln Leu Asn Arg Leu Ala Ala His Pro Pro Phe Ala Ser Asp Pro
20 25 30

Met Gly Ala Pro Gly Thr Pro Gly Pro Gln Gly Leu Pro Gly Ser Pro
35 40 45

Gly Ala Pro Gly Thr Pro Gly Pro Gln Gly Leu Pro Gly Ser Pro Gly
50 55 60

Ala Pro Gly Thr Pro Gly Pro Gln Gly Leu Pro Gly Ser Pro Gly Ala
65 70 75 80

Pro Gly Thr Pro Gly Pro Gln Gly Leu Pro Gly Ser Pro Gly Ala Pro
85 90 95

Gly Thr Pro Gly Pro Gln Gly Leu Pro Gly Ser Pro Gly Ala Pro Gly
100 105 110

Thr Pro Gly Pro Gln Gly Leu Pro Gly Ser Pro Gly Ala Pro Gly Thr
115 120 125

Pro Gly Pro Gln Gly Leu Pro Gly Ser Pro Gly Ala Pro Gly Thr Pro
130 135 140

Gly Pro Gln Gly Leu Pro Gly Ser Pro Gly Ala Pro Gly Thr Pro Gly
145 150 155 160

Pro Gln Gly Leu Pro Gly Ser Pro Gly Ala Pro Gly Thr Pro Gly Pro
165 170 175

Gln Gly Leu Pro Gly Ser Pro Gly Ala Pro Gly Thr Pro Gly Pro Gln
180 185 190

Gly Leu Pro Gly Ser Pro Gly Ala Pro Gly Thr Pro Gly Pro Gln Gly
195 200 205

Leu Pro Gly Ser Pro Gly Ala Pro Gly Thr Pro Gly Pro Gln Gly Leu
210 215 220

Pro Gly Ser Pro Gly Ala Pro Gly Thr Pro Gly Pro Gln Gly Leu Pro
225 230 235 240

Gly Ser Pro Gly Ala Pro Gly Thr Pro Gly Pro Gln Gly Leu Pro Gly
245 250 255

Ser Pro Gly Ala Pro Gly Thr Pro Gly Pro Gln Gly Leu Pro Gly Ser

-continued

```
            260                           265                           270

Pro Gly Ala Pro Gly Thr Pro Gly Pro Gln Gly Leu Pro Gly Ser Pro
        275                 280                 285

Gly Ala Pro Gly Thr Pro Gly Pro Gln Gly Leu Pro Gly Ser Pro Gly
    290                 295                 300

Ala Pro Gly Thr Pro Gly Pro Gln Gly Leu Pro Gly Ser Pro Gly Ala
305                 310                 315                 320

Pro Gly Thr Pro Gly Pro Gln Gly Leu Pro Gly Ser Pro Gly Ala Pro
                325                 330                 335

Gly Thr Pro Gly Pro Gln Gly Leu Pro Gly Ser Pro Gly Ala Pro Gly
            340                 345                 350

Thr Pro Gly Pro Gln Gly Leu Pro Gly Ser Pro Gly Ala Pro Gly Thr
        355                 360                 365

Pro Gly Pro Gln Gly Leu Pro Gly Ser Pro Gly Ala Pro Gly Thr Pro
    370                 375                 380

Gly Pro Gln Gly Leu Pro Gly Ser Pro Gly Ala Pro Gly Thr Pro Gly
385                 390                 395                 400

Pro Gln Gly Leu Pro Gly Ser Pro Gly Ala Pro Gly Thr Pro Gly Pro
                405                 410                 415

Gln Gly Leu Pro Gly Ser Pro Gly Ala Pro Gly Thr Pro Gly Pro Gln
            420                 425                 430

Gly Leu Pro Gly Ser Pro Gly Ala Pro Gly Thr Pro Gly Pro Gln Gly
        435                 440                 445

Leu Pro Gly Ser Pro Gly Ala Pro Gly Thr Pro Gly Pro Gln Gly Leu
    450                 455                 460

Pro Gly Ser Pro Gly Ala Pro Gly Thr Pro Gly Pro Gln Gly Leu Pro
465                 470                 475                 480

Gly Ser Pro Gly Ala Pro Gly Thr Pro Gly Pro Gln Gly Leu Pro Gly
                485                 490                 495

Ser Pro Gly Ala Pro Gly Thr Pro Gly Pro Gln Gly Leu Pro Gly Ser
            500                 505                 510

Pro Gly Ala Pro Gly Thr Pro Gly Pro Gln Gly Leu Pro Gly Ser Pro
        515                 520                 525

Gly Ala Pro Gly Thr Pro Gly Pro Gln Gly Leu Pro Gly Ser Pro Gly
    530                 535                 540

Ala Pro Gly Thr Pro Gly Pro Gln Gly Leu Pro Gly Ser Pro Gly Ala
545                 550                 555                 560

Pro Gly Thr Pro Gly Pro Gln Gly Leu Pro Gly Ser Pro Gly Ala Pro
                565                 570                 575

Gly Thr Pro Gly Pro Gln Gly Leu Pro Gly Ser Pro Gly Ala Pro Gly
            580                 585                 590

Thr Pro Gly Pro Gln Gly Leu Pro Gly Ser Pro Gly Ala Pro Gly Thr
        595                 600                 605

Pro Gly Pro Gln Gly Leu Pro Gly Ser Pro Gly Ala Pro Gly Thr Pro
    610                 615                 620

Gly Pro Gln Gly Leu Pro Gly Ser Pro Gly Ala Pro Gly Thr Pro Gly
625                 630                 635                 640

Pro Gln Gly Leu Pro Gly Ser Pro Gly Ala Pro Gly Thr Pro Gly Pro
                645                 650                 655

Gln Gly Leu Pro Gly Ser Pro Gly Ala Pro Gly Thr Pro Gly Pro Gln
            660                 665                 670

Gly Leu Pro Gly Ser Pro Gly Ala Pro Gly Thr Pro Gly Pro Gln Gly
        675                 680                 685
```

-continued

Leu Pro Gly Ser Pro Gly Ala Pro Gly Thr Pro Gly Pro Gln Gly Leu
690 695 700

Pro Gly Ser Pro Gly Ala Pro Gly Thr Pro Gly Pro Gln Gly Leu Pro
705 710 715 720

Gly Ser Pro Gly Ala Pro Gly Thr Pro Gly Pro Gln Gly Leu Pro Gly
725 730 735

Ser Pro Gly Ala Pro Gly Thr Pro Gly Pro Gln Gly Leu Pro Gly Ser
740 745 750

Pro Gly Ala Pro Gly Thr Pro Gly Pro Gln Gly Leu Pro Gly Ser Pro
755 760 765

Gly Ala Pro Gly Thr Pro Gly Pro Gln Gly Leu Pro Gly Ser Pro Gly
770 775 780

Ala Pro Gly Thr Pro Gly Pro Gln Gly Leu Pro Gly Ser Pro Gly Ala
785 790 795 800

Pro Gly Thr Pro Gly Pro Gln Gly Leu Pro Gly Ser Pro Gly Ala Met
805 810 815

Asp Pro Gly Arg Tyr Gln Leu Ser Ala Gly Arg Tyr His Tyr Gln Leu
820 825 830

Val Trp Cys Gln Lys
835

( 2 ) INFORMATION FOR SEQ ID NO:104:

( i ) SEQUENCE CHARACTERISTICS:
( A ) LENGTH: 417 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:104:

Met Asp Pro Val Val Leu Gln Arg Arg Asp Trp Glu Asn Pro Gly Val
1 5 10 15

Thr Gln Leu Asn Arg Leu Ala Ala His Pro Pro Phe Ala Ser Asp Pro
20 25 30

Met Gly Ala Pro Gly Thr Pro Gly Pro Gln Gly Leu Pro Gly Ser Pro
35 40 45

Gly Ala Pro Gly Thr Pro Gly Pro Gln Gly Leu Pro Gly Ser Pro Gly
50 55 60

Ala Pro Gly Thr Pro Gly Pro Gln Gly Leu Pro Gly Ser Pro Gly Ala
65 70 75 80

Pro Gly Thr Pro Gly Pro Gln Gly Leu Pro Gly Ser Pro Gly Ala Pro
85 90 95

Gly Thr Pro Gly Pro Gln Gly Leu Pro Gly Ser Pro Gly Ala Pro Gly
100 105 110

Thr Pro Gly Pro Gln Gly Leu Pro Gly Ser Pro Gly Ala Pro Gly Thr
115 120 125

Pro Gly Pro Gln Gly Leu Pro Gly Ser Pro Gly Ala Pro Gly Thr Pro
130 135 140

Gly Pro Gln Gly Leu Pro Gly Ser Pro Gly Ala Pro Gly Thr Pro Gly
145 150 155 160

Pro Gln Gly Leu Pro Gly Ser Pro Gly Ala Pro Gly Thr Pro Gly Pro
165 170 175

Gln Gly Leu Pro Gly Ser Pro Gly Ala Pro Gly Thr Pro Gly Pro Gln
180 185 190

Gly Leu Pro Gly Ser Pro Gly Ala Pro Gly Thr Pro Gly Pro Gln Gly

-continued

| | | | | | | | | | | | | | | | |
|---|---|---|---|---|---|---|---|---|---|---|---|---|---|---|---|
| | | 195 | | | | | 200 | | | | | 205 | | | |
| Leu | Pro | Gly | Ser | Pro | Gly | Ala | Pro | Gly | Thr | Pro | Gly | Pro | Gln | Gly | Leu |
| | 210 | | | | | 215 | | | | | 220 | | | | |
| Pro | Gly | Ser | Pro | Gly | Ala | Pro | Gly | Thr | Pro | Gly | Pro | Gln | Gly | Leu | Pro |
| 225 | | | | | 230 | | | | | 235 | | | | | 240 |
| Gly | Ser | Pro | Gly | Ala | Pro | Gly | Thr | Pro | Gly | Pro | Gln | Gly | Leu | Pro | Gly |
| | | | | 245 | | | | | 250 | | | | | 255 | |
| Ser | Pro | Gly | Ala | Pro | Gly | Thr | Pro | Gly | Pro | Gln | Gly | Leu | Pro | Gly | Ser |
| | | | 260 | | | | | 265 | | | | | 270 | | |
| Pro | Gly | Ala | Pro | Gly | Thr | Pro | Gly | Pro | Gln | Gly | Leu | Pro | Gly | Ser | Pro |
| | | 275 | | | | | 280 | | | | | 285 | | | |
| Gly | Ala | Pro | Gly | Thr | Pro | Gly | Pro | Gln | Gly | Leu | Pro | Gly | Ser | Pro | Gly |
| | 290 | | | | | 295 | | | | | 300 | | | | |
| Ala | Pro | Gly | Thr | Pro | Gly | Pro | Gln | Gly | Leu | Pro | Gly | Ser | Pro | Gly | Ala |
| 305 | | | | | 310 | | | | | 315 | | | | | 320 |
| Pro | Gly | Thr | Pro | Gly | Pro | Gln | Gly | Leu | Pro | Gly | Ser | Pro | Gly | Ala | Pro |
| | | | | 325 | | | | | 330 | | | | | 335 | |
| Gly | Thr | Pro | Gly | Pro | Gln | Gly | Leu | Pro | Gly | Ser | Pro | Gly | Ala | Pro | Gly |
| | | | 340 | | | | | 345 | | | | | 350 | | |
| Thr | Pro | Gly | Pro | Gln | Gly | Leu | Pro | Gly | Ser | Pro | Gly | Ala | Pro | Gly | Thr |
| | | 355 | | | | | 360 | | | | | 365 | | | |
| Pro | Gly | Pro | Gln | Gly | Leu | Pro | Gly | Ser | Pro | Gly | Ala | Pro | Gly | Thr | Pro |
| | 370 | | | | | 375 | | | | | 380 | | | | |
| Gly | Pro | Gln | Gly | Leu | Pro | Gly | Ser | Pro | Gly | Ala | Met | Asp | Pro | Gly | Arg |
| 385 | | | | | 390 | | | | | 395 | | | | | 400 |
| Tyr | Gln | Leu | Ser | Ala | Gly | Arg | Tyr | His | Tyr | Gln | Leu | Val | Trp | Cys | Gln |
| | | | | 405 | | | | | 410 | | | | | 415 | |
| Lys | | | | | | | | | | | | | | | |

( 2 ) INFORMATION FOR SEQ ID NO:105:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..7
( D ) OTHER INFORMATION: /note= "X = a basic or acidic amino acid, particularly K or E."

( x i ) SEQUENCE DESCRIPTION: SEQ ID NO:105:

| | | | | | | |
|---|---|---|---|---|---|---|
| Lys | Leu | Xaa | Leu | Ala | Glu | Ala |
| 1 | | | | 5 | | |

( 2 ) INFORMATION FOR SEQ ID NO:106:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:106:

| | | | |
|---|---|---|---|
| Xaa | Pro | Pro | Pro |
| 1 | | | |

( 2 ) INFORMATION FOR SEQ ID NO:107:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:107:

His Cys Cys His
1

( 2 ) INFORMATION FOR SEQ ID NO:108:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:108:

Cys His His Cys
1

( 2 ) INFORMATION FOR SEQ ID NO:109:

( i ) SEQUENCE CHARACTERISTICS:
( A ) LENGTH: 111 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:109:

ATGACCATGA TTACGCCAAG CTTGGGCTGC AGGTCGACTC TAGAGGATCC CCATTTCCGT 60

GTCGCCCTTA TTCCCTTTTT TGCGGCATTT TGCCTTCCTG TTTTTGCTCA C 111

( 2 ) INFORMATION FOR SEQ ID NO:110:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:110:

Met Thr Met Ile Thr Pro Ser Leu Gly Cys Arg Ser Thr Leu Glu Asp
1 5 10 15

Pro His Phe Arg Val Ala Leu Ile Pro Phe Phe Ala Ala Phe Cys Leu
20 25 30

Pro Val Pro Ala His
35

( 2 ) INFORMATION FOR SEQ ID NO:111:

( i ) SEQUENCE CHARACTERISTICS:
( A ) LENGTH: 67 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:111:

GATCCTATGT TTAAATATTC TCGCGATCCG ATGGGTGCCA TGGACCCGGG TCGATATCAG 60

CTGGATC 67

( 2 ) INFORMATION FOR SEQ ID NO:112:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:112:

Asp Pro Met Phe Lys Tyr Ser Arg Asp Pro Met Gly Ala Met Asp Pro
1 5 10 15

Gly Arg Tyr Gln Leu
20

PEPTIDES COMPRISING REPETITIVE UNITS OF AMINO ACIDS AND DNA SEQUENCES ENCODING THE SAME

CROSS-REFERENCE TO RELATED APPLICATIONS

This application is a continuation-in-part of application Ser. No. 08/175,155, filed Dec. 29, 1993, now U.S. Pat. No. 5,641,648, issued Jun. 24, 1997, which application is a continuation-in-part of application Ser. No. 08/053,049, filed Apr. 22, 1993, now abandoned, which application is continuation of application Ser. No. 07/114,618, filed Oct. 29, 1987, now U.S. Pat. No. 5,243,038 issued Sept. 7,1993, which application is a continuation-in-part of application Ser. No. 927,258, filed Nov. 4, 1986, now abandoned.

The government has certain rights in this invention as a result of support provided by the Department of the Navy for the work leading to the present invention.

INTRODUCTION

1. Technical Field

The field is high-molecular-weight polymers, either nucleic acids or the protein expression products of the nucleic acids.

2. Background

Proteins are a broad and diverse class of molecules which "play crucial roles in virtually all biological processes." Stryer, Biochemistry (1988) p. 15. Proteins play active roles in: enzyme catalysis; transport and storage of ions and small molecules; coordinated motion; mechanical support; immune protection; signal transduction; and modulation of growth and differentiation. As the science of protein characterization has progressed, a large number of proteins have been sequenced. Of this large number of sequenced proteins, there is a finite subset in which the amino acids that make up the protein are arranged in repetitive units, where the repetitive units provide a motif to the amino acid sequence of the protein. Many of the structural proteins fall within this subset. In the series of tandem units, the naturally occurring proteins have a significant number of substitutions to vary the pattern, while still substantially retaining the pattern of repeat units.

Because of the crucial role proteins play in a variety of biological processes, there has been considerable interest in the development of technologies which may be employed to produce naturally occurring proteins in a controlled fashion, often in purer form and/or in larger quantities than the protein is produced in nature. Also, there is an interest in producing proteins which build upon the structural properties of the naturally occurring proteins, while providing for enhanced or novel properties.

Recombinant DNA technology has been applied in the isolation of natural genes and the expression of these genes in a variety of host cells. Typically, this technology has had utility in producing biologically active polypeptides, such as cytokines or peptide hormones, which were impractical to produce in useful amounts by other means. It was also possible to produce modified proteins by isolating natural genes and utilizing the techniques of site specific, in vitro mutagenesis to alter these genes and thereby change the polypeptides produced. Other polypeptides have been created by combining sections of various native genes to produce new polypeptides that are chimeric molecules of the several naturally occurring molecules.

For the most part, the peptides which have been produced by recombinant techniques have not involved long regions of repeating units involving the same nucleic acid sequences. Where there are extended repetitive sequences in a gene, there is the opportunity to loop out portions of the gene, to form secondary and tertiary structures, to create frame shifts, and to have substantial intracellular instability of the gene. There was, therefore, some uncertainty as to the ability to produce proteins dependent upon the synthesis and expression of extended repetitive regions.

There are many applications where structural proteins may find use and the naturally occurring proteins are not adequate for the required purpose. Also, with many proteins there are the issues of source, purity, availability, and economics. The opportunity to produce proteins which, while based on naturally occurring motifs, provide for modifications of the naturally occurring protein in providing for greater identity of the repetitive units, introduction of unnatural intervening sequences, combinations of motifs, and the like, is of great interest. This opportunity allows for the production of proteins with unique properties in a background of the properties afforded the naturally occurring protein by the repetitive motif.

BRIEF DESCRIPTION OF THE RELEVANT LITERATURE

The cloning of multiple lactose operators up to four in tandem is disclosed by Sadler et al., *Gene* (1980) 8:279–300. Hybrid bacterial plasmids containing highly repeated satellite DNA is disclosed by Brutlag et al., *Cell* (1977) 10:509–519. The synthesis of a poly(aspartyl-phenylalanine) in bacteria is disclosed by Doel et al., *Nucleic Acids Research*, (1980) 8:4575–4592. A method for enriching for proline content by cloning a plasmid which codes for the production of a proline polymer was disclosed by Kangas et al., *Applied and Environmental Microbiology* (1982) 43:629–635. The biological limitations on the length of highly repetitive DNA sequences that may be stably maintained within plasmid replicons is discussed by Gupta et al. in Bio/Technology, p. 602–609,September 1983.

Other references of interest include Davanloo, P. et aL, *Proc. Natl. Acad. Sci.USA* (1984) 81:2035–2039.

SUMMARY OF THE INVENTION

Novel recombinant proteins comprising one or more small repetitive units are provided, where the repetitive units are based on naturally occurring repetitive units. The proteins provide for a variety of physical properties, differing in their properties from the natural proteins in their identical repeat units, variations in novel combinations, and introduction of intervening sequences imparting novel properties to the proteins. By employing motifs associated with naturally occurring proteins, the subject proteins enjoy properties of the naturally occurring protein, as well as unique properties associated with the differences in composition between the naturally occurring protein and the subject recombinant proteins.

BRIEF DESCRIPTION OF THE FIGURES

FIG. 1: Plasmid pSY701 structure (SEQ ID NOS:109 and 110) .

FIG. 2A–B: Immunoblots of polypeptide products using antibody to (a) beta-lactamase or to (b) gly-ala-peptide.

FIG. 3: Construction flowchart for plasmid pG10/SlpI.

FIG. 4A–4C: Immunoblots of polypeptide products (a) T7gp10/SlpI with anti-Slp Ab, (b) T7gp9/SlpI with anti-Slp Ab or (c) staining with Coomassie blue.

FIG. 5: Construction flowchart for plasmid pSY856.

FIG. 6: Time course for accumulation of the kanamycin-resistance gene product with the T7 system.

FIG. 7: Construction flowchart for plasmid pSY857 (SEQ ID NOS: 111 and 112).

FIG. 8: Construction flowchart for plasmid pSY980.

FIG. 9A–B: (A) Amido black stain or gel containing the product of beta-galactosidase/SlpIII gene fusion; (b) immunoblot of same product with anti-Slp antibody.

FIG. 10: Construction flowchart for plasmid pSY1280.

DESCRIPTION OF SPECIFIC EMBODIMENTS

Novel recombinant proteins are provided having naturally occurring repeating units: a single small naturally occurring repeating unit, a combination of small naturally occurring repeating units, as block or random copolymers, or with intervening sequences between blocks of the repeating units. The novel polypeptides find use as fibrous or structural proteins, including crystalline, elastomeric, tough and bony materials, e.g. proteins similar to, but different from, silk, elastin, collagen, keratin or other naturally occurring structural polymers having a repetitive amino acid sequence motif. The gene encoding the repeating-unit-containing peptides is produced to particularly avoid problems previously associated with genes containing multiple repeating units.

Based on a search of reported sequences of naturally occurring proteins, there is a limited number of naturally occurring motifs that find usage. These motifs can be based on a single amino acid which is repeated at a predetermined spacing and the repeating unit has an additional restriction, e.g. collagen, where glycine is repeated every third amino acid and there is a high proportion of proline for the remaining two amino acids; or a single motif, which is used, but is not perfectly repeated in the protein, e.g. fibroin and elastin; or a motif, where the units vary as to a single amino acid, e.g. keratin.

In these naturally occurring proteins, there will be at least about 8, more usually at least about 10 tandem repeats, frequently 20 or more tandem repeats, before there is an intervening sequence, where at least about 50 number % of the amino acids of the naturally occurring protein are members of the repeat units. For the most part, the repeating unit containing proteins are structural proteins and/or adhesive proteins, being present in prokaryotes and eukaryotes, including vertebrates and non-vertebrates.

Amino acids which are popularly used, frequently being repeated twice in the same repeating unit, include G, P, A, S, T and V. The common amino acid may be contiguous or spaced apart. Common did themes include GA, VP, PP, TT, GG, PE, and PM. For the most part the repetitive unit will be of from 3 to 20, generally from 3 to 15, frequently 3 to 12, usually 3 to 9, and more usually 3 to 6 amino acids. For the most part, the repetitive units will have few aromatic amino acids, usually not more than two, more usually not more than one, a common aromatic amino acid being Y.

The polypeptide will for the most part have the following formula:

$$K'_k(W'M_r'X'_xN'_sY'_y)_iL'_1$$

wherein:

W' will have the following formula $$[(D)_n(E)_p]_q$$

wherein:

D is the amino acid sequence encoded for by A (see below for the nucleic acid sequence) and therefore has the numerical limitations based on 3 nucleotides defining a codon that codes for one amino acid;

E is the amino acid sequence encoded for by B, and therefore has the numerical limitations based on 3 nucleotides defining a codon, where each E may be the same or different, depending upon the coding of B;

and, wherein, likewise K', W', M', X', N', Y' and L' is the amino acid sequence encoded for by K, W, M, X, N, Y and L respectively. However, in the case of K' and L', subsequent processing, such as protease treatment, cyanogen bromide treatment, etc., may result in partial or complete removal of the N- or C-terminal non-multimeric chains.

n, p, q, k, r, s, x, i and l have the same definitions as indicated in the formula for the nucleic acids encoding the proteins of the subject invention.

Particular polymeric compositions having amino acid repeating units having the same composition (D) will have the following formula, where x and y are 0, $$K'_k[(D)_n(E)_p]_qL'_l$$

where all of the symbols have been defined previously; and the DNA sequence will have the formula $$K_k[(A)_n(B)_p]_qL_l$$

where all of the symbols are defined below.

The proteins may be homopolymers in the sense of having a single repetitive unit, random copolymers as having two or more repetitive units which do not form an identical repeating pattern, or block copolymers where at least one of the repeating units forms a block of at least 2 repetitive units, more usually at least 3 repetitive units, frequently 4 or more, generally not more than about 50 repetitive units, frequently not more than about 30 repetitive units.

For the most part, the repetitive units of interest will be those units which, when incorporated into the subject polypeptides, impart physical characteristics to the polypeptide that are found in the naturally occurring protein from which the repetitive unit is derived. Characteristics imparted to the polypeptides by the repetitive units will generally be structural, e.g repetitive units which provide for α-helices, β-pleated sheets, or other structural characteristic of interest. The proteins may have the capability of forming or participating in the formation of formed objects, such as films, fibers, gels, membranes, or the like, or may be amorphous, such as in adhesives, coatings, viscous fluids, emulsions and the like.

The compositions of the invention will usually have a molecular weight of at least about 30 kDal, more usually at least about 50 kDal, frequently at least about 60 kdal and usually not exceeding about 250 kDal, more usually not exceeding 150 kDal, frequently not exceeding 125 kDal, preferably being in the range of about 50 to 125 kDal. Generally the repetitive units will include a minimum of 50 number %, usually at least about 65 number %, more usually at least about 75 number %, frequently at least about 80 number % of the total number of amino acids in the protein. The proteins may have non-repetitive termini, generally each terminus not exceeding about 125 amino acids, frequently not exceeding about 75 amino acids, preferably not exceeding about 65 amino acids. These non-repetitive sequences may be present to fulfill specific functions, as a convenience in the synthesis and expression of the gene and the protein, to permit secretion, to permit ease of identification, purification, processing and the like.

Generally, a different N-terminus will be the result of insertion of the gene into a vector in a manner that results in expression of a fusion protein. Any protein which does not interfere with the desired properties of the product may provide the N-terminus. Particularly, endogenous host proteins, e.g. bacteria proteins, may be employed. The choice of protein may depend on the nature of the transcriptional initiation region.

Of particular interest will be polypeptides which comprise repetitive units found in naturally occurring structural proteins. Naturally occurring structural proteins, as opposed to receptors, growth factors, etc., are those proteins which are capable of forming extended three-dimensional structures by themselves or with other structural proteins, either intra- or extracellularly, and are generally, though not necessarily, filamentous or fibrous. Known structural proteins that comprise repetitive amino acid units of from 3–20 amino acids include: Glue polypeptide sgs3 (PTTTK), reported in J.M.O.B.A. (1983) 168:765–790 (SEQ ID NO:01); Glue Protein (AKPSYPPTYK) reported in A.B.B.I.A. (1989) 269:415–422 (SEQ ID NO:02); Hydroxyproline Rich Glycoproteins, such as (PPVYK) reported in P.N.A.S. (1988) 85:1082–1085 (SEQ ID NO:03), (xPPP) reported in P.L.C.E.E. (1989)1:901–912 (SEQ ID NO:106) and (PPVYK) reported in P.L.P.H.A. (1992) 98:919–926 (SEQ ID NO:03); Mucin (TTTPDV) reported in J.B.C.H.A. (1991) 266:22733–22738 (SEQ ID NO:04); Oothecins (GGLGY) reported in B.B.A.C.A. (1984) 422–428 (SEQ ID NO:05); p39 (APAAP) reported in V.I.R.L.A. (1989) 168:354–362 (SEQ ID NO:06); Proline rich proteins, such as (PEPK) and (PMPK) reported in P.M.B.I.D. (1991) 16:663–670 (SEQ ID NOS:07 & 8), (SPPPP) reported in P.M.B.I.D. (1988) 11:483–494 (SEQ ID NO:9), (PEPMPK) reported in P.M.B.I.D. (1991) 16:663–670 (SEQ ID NO:10) and (PPVYKPPVQK) reported in P.L.C.E.E. (1989) 1:945–952 (SEQ ID NO:11); SbPRP1 (PPVYK) reported in P.L.C.E.E. (1989) 1:937–944 (SEQ ID NO:03); SbRPR2 (PPVK) & (PPVEK) (SEQ ID NOS:12 &13) and SbRPR2 and 3 (PPVYK) (SEQ ID NO:03) reported in J.B.C.H.A. (1990) 265:2470–2475; SPAG-1 (PGVGV) and (VGVAPG) reported in M.B.I.P.D. (1992) 53:105–112 (SEQ ID NOS: 14 & 15); Extensins, such as (SPPPPSPKYVYK) (SEQ ID NO:16), (SPPPPYYYKSPPPPSP) (SEQ ID NO:17), (SPPPPPTPSYGHPKTP) (SEQ ID NO:18), and (SSPPPPSPSPPPPTYYY)(SEQ ID NO:19) all reported in P.M.B.I.D. (1992) 20:5–17; and NF-M (KSPVPKSPVEEKG) (SEQ ID NO:20) reported in E.M.J.O.D. (1987) 6:1617–1626.

Of particular interest are polypeptides which have as a repeating unit SGAGAG (SEQ ID NO:21) and GAGAGS (SEQ ID NO: 41) (G=glycine; A=alanine; S=serine). This repeating unit is found in a naturally occurring silk fibroin protein, which can be represented as GAGAG(SGAGAG)$_8$SGAAGY(Y=tyrosine) (SEQ ID NO:22).

A silk-like-protein (Slp) gene may be produced by providing oligomers or multemers of from about 5 to 25 repeat units as described above, more usually of about 6 to 15 repeat units. By having different cohesive ends, the oligomers may be concatemerized to provide for the polymer having 2 or more of the oligomeric units, usually not more than about 50 oligomeric units, more usually not more than about 30 oligomeric units, and frequently not more than about 25 oligomeric units.

The silk-like proteins may be varied by having alternate multimers with the same or different handedness. For example, in the formula, $(B)_p$ may provide an even or odd number of amino acids. In silk, the hydrogens of the glycine may align on one side and the methyls and hydroxyls of alanine and serine on the other. If $(B)_p$ is even, there will be continuous alignment, if odd, there will be alternating alignment of $(A)_n$. Thus, different properties can be achieved by changing the number of amino acids encoded by $(B)_p$.

Of particular interest are polypeptides which mimic the composition and physical properties of silks found in nature, e.g. *Bombyx mori.*

Also of interest are polypeptides which have as a base repeating unit GVGVP(G=glycine, V=valine, P=proline) (SEQ ID NO:23), which may be found in naturally occurring elastin; also VPGVG (SEQ ID NO:24) and/or APGVGV (SEQ ID NO:25) units.

Of particular interest is a block of about 2 to 32, preferably about 4 to 16, units separated by a sequence of about 3 to 120, usually about 3 to 72 amino acids, preferably 10 to 60 amino acids, which may include an internal repeat of from 3 to 12 amino acids different from the other repeating unit. For example, the first repeat sequence could be VPGVG (SEQ ID NO:24) second repeat sequence could be GAGAGS (SEQ ID NO:41), repeated twice. The total number of repeating units in the protein will generally be in the range of about 10 to 500, more usually 30 to 350.

Of particular interest are proteins which comprise the repeat unit of elastin and mimic the properties of elastin and provide for elastomeric properties, and copolymers which impart the elastic properties of elastin in conjunction with the characteristics of other repeating units.

Of particular interest are collagen like proteins which have the sequence $G\alpha\beta$, where $\alpha$ and $\beta$ may be any amino acid, particularly one being proline. Usually in the protein $\alpha$ and $\beta$ will be selected so that the total percent proline in the protein is between about 10 to 45 number % of the amino acids in the protein. The amino acids of particular interest other than glycine and proline are alanine, isoleucine, leucine, valine, serine, threonine, asparagine, glutamine, lysine, arginine, aspartic acid, glutamic acid, histidine. By known procedures after production of the protein, one or more prolines may be oxidized to hydroxyproline.

Also of interest are the polypeptides which have as a repeating unit K-L-(1)-L-A-E-A (SEQ ID NO:105) where 1 is a basic or acidic amino acid, particularly K or E and the repeating units alternate as to whether 1 is a basic or acidic amino acid. This structure is commonly found in keratin.

The copolymer involving repeating units is a powerful method for varying properties, by appropriate choice of the different units, the number of units in each block and the total number of repeat units of the blocks. Thus, by varying the number and arrangement of primary repeating units, a variety of different physical and chemical properties can be achieved.

Exemplary of the use of the block copolymers are combinations of silk units and elastin units to provide products having properties distinctive from polymers only having the same monomeric unit. See, for example, PCT/US95/02772.

Intervening groups may also be provided where the intervening group will be from about 1 to 50, usually from about 1 to 30, more usually from about 3 to 30 amino acids. The intervening group will be other than a repetitive unit, normally having a chemically reactive functionality, e.g. C, S, T, D, E, K or R, a physiologically active functionality, a chelating functionality, a grouping which modifies the conformational structure of the protein, or the like.

For the intervening oligomers or turns between the strands, (where by "strands" is intended an ordered sequence capable of alignment with a second strand or sequence having substantially the same or a complementary sequence, e.g. hydrophobic aligns with hydrophobic and hydrophilic aligns with hydrophilic) various sequences may be used, depending upon the desired purpose of the polymer. Thus, the intervening sequence may be unaligned, flexible, accessible, functional or combinations thereof Thus, the intervening sequence in association with the strand sequence can be designed to provide a wide variety of products which may be formed, fabricated, extruded, spun, woven, coated, or the like. The intervening sequence may provide for a ligand, which may serve to bind to antibodies, naturally occurring receptors, non-amino-acid molecules, or the like. In this way, the polymeric structures may be used to specifically bind a wide variety of molecules serving as affinity columns, use in diagnosis, sensors, cell separation, device coatings having, for example, antithrombogenic properties, cell substrates, and the like.

The intervening sequence may provide chemically active amino acids for chemical crosslink sites, which may serve to covalently attach functional peptides, synthetic or natural polymers or proteins, non-amino acid molecules, and the like. The intervening sequence may be a naturally occurring sequence or a modified naturally occurring sequence. Naturally occurring sequences may be derived from a wide variety of sources with a variety of functions. Such sequences may be a cellular growth inhibitor sequence, e.g., from tenascin (Chiquet-Ehrismann et al., (1988) *Cell* 53:383–390); cell growth promoting attachment factors e.g., from fibronectin, -RGD-, -REDV (SEQ ID NO:26)- (Humphries et al., (1988) *J. Cell Biol.* 103:2637–2647), vitronectin, -RGD- (Suzuki et al., (1985) *EMBO J.* 4:2519–2524), collagen, -RGD-, and as described in WO 89/03392, laminin B1 - YIGSR (SEQ ID NO:27)- (Graf et al., (1987)*Cell* 48:989–996), bacterial adhesive, -SLF-, -ALF-; (Jacobs et al., (1987) *J Bacteriology* 1691:735–741), growth hormones and insulin; inclusion sequences (GAGC and GCCV (SEQ ID NOS:28 & 29), which provide systems for attachment and cross-linking; VSPD, VCDP and DPGK (SEQ ID NO:30–32), which provide an unaligned structure); cellular function activators, such as major histocompatibility complex antigens, Class I and II, particularly the $\alpha_1$, $\alpha_2$, $\beta_1$ and $\beta_2$ regions, e.g., HLA-A2 amino acids 50–80 and 140–170 (Bjorkman et al., (1987) *Nature* 329:512–518) and HLA-D amino acids 1–90 (Todd et al., (1988) *Science* 240:1003–1009); growth factor domains, e.g., EGF, TGF and VGF, IL-1–10, particularly -2, -3 and -4, and erythropoietin; viral attachment sequences, such as human CD4 amino acids 35–60 (Clayton et al., (1988) *Nature* 335:363–366) and 70–95 (Lifson et al., (1988) *Science* 241:712–716); sequences which promote the binding of non-protein molecules, such as the heparin binding domain of vitronectin, metal binding domains, e.g., metallothioneins, H-H, H-C-C-H (SEQ ID NO:107) and C-H-H-C (SEQ ID NO:108), etc. glucose and other sugar binding domains, e.g., lectins, B chains of toxins, such as abrin, ricin, diphtheria toxin, safratoxin, or fragments thereof, etc.; drug or toxin binding domains for detoxification; and chemically active amino acids or amino acid sequences for post-translational modifications, such as N-X-S for N-linked glycosylation and the amino acids, C, M, H, K, R, D, E, W, P, Y, N and Q for chemical modification.

Sequences of specific interest as intervening sequences include:

D P G K G X Y wherein at least one of X and Y is C; (SEQ ID NO:33)

E P G Y I G S R C D A G Y (SEQ ID NO:34);

P K G D R G D A G P K (SEQ ID NO:35);

A V T G R G D S P A S (SEQ ID NO:36);

G R G G S F G G S S Y G G G S (SEQ ID NO:37);

G A G C G D P G K G C C V A (SEQ ID NO:38);

V C D R G Y I G S R C D (SEQ ID NO:39); and

P K G D R A D A G P K (SEQ ID NO:40);

where conservative substitutions may be made other than at the functional site.

For the cysteine product it will be desirable to have two or three cysteines in a multimer unit, preferably having a cysteine proximal to each end of the multimer unit. For chemical cleavage the dipeptide DP or EP is desirable.

The repeating unit(s) and/or the intervening sequences may desirably contain proteolytic enzyme cleavage sequences which may facilitate processing, purification or the physiological resorption rate of the polymer. such sequences are known in the art and need not be exemplified here.

Genes encoding the subject polypeptides produced according to the methods described herein will generally be at least about 900 nt in length, usually at least 1200 nt in length, preferably at least 1500 nt in length, usually not more than about 7.5 knt in length, more usually not more than about 6 knt in length, frequently not more than about 4 knt in length.

The genes of the subject invention generally comprise concatenated monomers of DNA encoding the same amino acid sequence, where only one repeating unit is present to form a homopolymer, where all or a part of two or more different monomers encoding different amino acid repeating units may be joined together to form a new monomer encoding a block or random copolymer. The individual amino acid repeating units will have from 3 to 20 amino acids (9 to 60 nt), generally 3 to 15 amino acids (9 to 45 nt), usually 3 to 12 amino acids (9 to 36 nt), more usually 3 to 9 amino acids (9 to 27 nt) amino acids, usually having the same amino acid appear at least twice in the same unit, generally separated by at least one amino acid. In some instances, the minimum number of amino acids will be 4. Within a monomer, dsDNA encoding the same amino acid repeating unit may involve two or more nucleotide sequences, relying on the codon redundancy to achieve the same amino acid sequence.

The genes of the subject invention comprise regions comprising repeats of the repetitive units, usually a block of at least 2 units, and up to the entire region of repetitive units. Blocks of repetitive units may be interspersed with individual or blocks of other repetitive units, or intervening sequences, as described previously. The repeating units may have the same sequence or there may be 2 or more different sequences employed to encode the repeating unit, using the codon redundancy for a particular amino acid to vary the sequence. Ease of preparation and greater gene stability appear to be obtained with the variation.

For the most part the DNA compositions of this invention may be depicted by the following formula:

$$K_k(W\ M_r X_x N_s Y_y)_i L_l$$

wherein:

K is a DNA sequence encoding an amino acid sequence of from about 1 to 125 amino acids, usually 1 to 65 amino acids, which may be any sequence depending upon the manner of preparation of the construct and the purpose of the protein product, generally being fewer than about 20% of the total number of amino acids, more generally being fewer than about 10% of the total number of amino acids, which may be any sequence, particularly a naturally occurring sequence where the multimer structural gene has been fused to another DNA sequence in reading frame. K, if present, will have the initiation methionine codon. L may be the same or different from K, coming within the definition of K, but lacking the initiation methionine codon.

k and l are the same or different and are 0 or 1;

W has the formula:

$$[(A)_n(B)_p]_q$$

wherein:

A is a DNA sequence coding each time that it appears for the same amino acid repeating unit normally having at least one amino acid appear at least twice in the sequence, where A will generally be from about 9 to 60 nucleotides (nt), more usually for about 9 or 12 to 45 nt, preferably from about 9 or 12 to 36 nt, more preferably from about 9 or 12 to 27 nt;

where there will usually be at least two different A's, usually not more than about twenty different A's, more usually not more than about ten different A's, which code for the same amino acid sequence but differ from each other by at least one nucleotide and may differ by as many as ten nucleotides, usually not differing by more than about five nucleotides from another A sequence, each of the different A's usually being repeated at least twice; for example, at least two different codons can be employed for the same amino acid, e.g., GGC and GGA for glycine, in different A's coding for the same amino acid sequence unit;

n will be an integer of at least 2, usually at least about 4, more usually at least about 8, and not more than about 250, usually not more than about 200, frequently not more than about 125, and in some instances may not exceed about 50;

B is a DNA sequence different from A coding for an amino acid sequence other than the amino acid sequence unit coded by the A unit and serves as a linking unit between oligomers of A units. B will generally have from about 3 to 150 nt, (1 to 50 amino acids) more usually from about 3 to 105 nt (1 to 35 amino acids);

where the B units appearing in the gene may be the same or different, there usually not being more than about 10 different B units, more usually not more than about 5 different B units, where functionally similar B units, particularly encoding the same oligopeptide, may differ from about 1 to 45 nt, more usually from about 1 to 15 nt, where the different B's may code for the same or different amino acid sequence;

p is 0 or 1 and may differ each time there is a successive A unit;

q is an integer of at least 1 and will vary with the number of nucleotides in A and B, as well as the values of n and p. The variable q will be selected so as to provide for at least 900 nt for the multimeric portion of the structural gene, preferably at least about 1250 nt, more preferably at least 1500 nt, and the number of nucleotides will usually not exceed about 7500 nt, more usually not exceeding about 6 knt, generally being in the range of about 900 to 6,000 nt, more usually to about 4 knt; and M is a DNA nucleotide sequence of about 3 to 150 nt, usually being 9 to 150 nt, more usually not more than about 90 nt, which may encode any amino acid sequence, usually encoding a functional sequence which provides for a natural or synthetic sequence resulting in a biological or chemical function or activity (see WO 90/05177, the disclosure of which is herein incorporated by reference);

r and s are the same or different, being 0 to 3, usually 0 to 2, depending on whether an intervening group is present in the polymer, usually being 1 to 2, where different, the same or similar functional groups may be combined in a contiguous manner;

N is the same or different from M and comes within the same definition as M;

X may be the same as or different from W, usually different, and will have the formula:

$$[(A^1)_{n^1}(B^1)_{p^1}]_{q^1}$$

wherein:

$A^1$, $B^1$, $n^1$, $p^1$ and $q^1$ are the same as or different from A, B, n, p and q respectively, at least one being different, wherein the analogous symbols come within the same definition as their counterparts;

x is 0or 1;

Y may be the same as or different from W, usually different, and will have the formula:

$$[(A^2)_{n^2}(B^2)_{p^2}]_{q^2}$$

wherein:

$A^2$, $B^2$, $n^2$, $p^2$ and $q^2$ are the same as or different from A, B, n, p and q respectively, at least one being different, wherein the analogous symbols come within the same definitions as their counterparts.

y is 0 or 1;

i is 1 to 100, usually 1 to 50, more usually 1 to 30, particularly 1, when x, y, r and s are 0;

when x or y are 1, q, $q^1$ and $q^2$ will be a total of at least 2, usually at least 5 and not more than about 50, usually not more than about 33.

Particular DNA sequences encoding copolymeric compositions having a repeating unit of two to three multimeric blocks will have the following formula:

$$K_k"(W"_{w"}M"_{m"}X"_{x"}N"_{n"}Y"_{y"})_{i"}L_l'$$

wherein:

W" is a multimer having the formula $$[(A^3)_{n^3}(B^3)_{p^3}]_{q^3}$$

where $A^3$ is of 3 to 15, usually 3 to 9 codons, otherwise coming within the definition of A;

$n^3$ will be from about 2 to 40, usually 2 to 32;

$B^3$ is of from 1 to 50, usually 3 to 36 codons;

$p^3$is 0 or 1;

$q^3$ is of from about 1 to 50, usually 2 to 40, depending on the value of $n^3$, as discussed previously for n and q;

X" and Y" are the same as or different from W", usually different, coming within the same definitions as W";

M" and N" come within the definitions of M and N;

i"is at least 1, usually at least 5 and not more than about 75, usually not more than about 50, generally not exceeding 30;

where $q^3$ or i"is 1, the sum of $q^3$ and i" will be at least 3;

with the other symbols as defined previously, wherein at least one of x" and y" is 1.

The nucleotide sequences which are employed will be synthesized, where the repetitive units may have different codons for the same amino acid as described above. Desirably, fewer than about 75%, usually fewer than about 60%, frequently fewer than about 25% of the repeats will have the identical nucleic acid sequence. Often, none of the repeats will have the same nucleic acid sequence. Greater nucleic acid sequence diversity will be employed where the initial constructs are experimentally shown to undergo spontaneous recombination events.

The repetitive proteins can find a variety of uses. The Slp proteins may be used in producing fibers having unique properties, as a substitute for silk, and the like. Collagen proteins can be produced, where the collagen is free of the telopeptide. Atelopeptidecollagen should have little if any immunogenicity, so as to be a useful structural element for a variety of prosthetic devices or for use as a collagen substitute in other applications. Similarly, other proteins having repetitive sequences, such as keratin, can also be prepared in accordance with the subject invention. Other useful repetitive proteins can be prepared based on sequences of spider silks and other repetitive animal fibers. Artificial peptides useful for immunization can also be prepared based on repeating sequences present in various surface antigens of disease-causing microorganisms, such as parasites, bacteria, and viruses. Methods have been described in the literature to prepare the subject proteins having extended regions of repetitive units.

Since the original development of the subject inventions, advances in the field of synthesis have allowed the reliable synthesis of longer nucleic acid sequences, which were not previously available. Therefore, the methods have undergone an evolution from using relatively short segments which could be reliably synthesized followed by concatenation and sequencing for verification of sequence to the synthesis of much longer sequences, where concatenation was no longer required.

The methods for production of the synthetic genes encoding the subject polypeptides involve preparation of a dsDNA "monomer", which is an extended segment of DNA principally encoding amino acid repeating units, where the dsDNA monomer is generally a repeating segment of the final product, where the final product will have from 2, frequently at least 3, and up to 50, usually not more than about 30, more usually not more than about 20, monomeric units. There is one exception, to be described below, where the monomer may be the entire final repeating unit gene. The monomer will be a dsDNA whose sequence is, with one exception, established prior to its multimerization to provide the gene.

The size of the dsDNA monomer is dependent upon the desired amino acid monomer sequence as well as the way in which the monomer is obtained. If the monomer is constructed using any newly synthesized and ligated DNA, then the monomer is always sequenced prior to multimerization. If the gene monomer is constructed solely from digestion fragments of previously constructed and sequenced monomers, then the final gene monomer is typically characterized by restriction digests. Therefore, the gene monomer can be as large as the final gene, depending upon the desired amino acid repeating unit sequences and periodicity.

There are three ways to obtain the monomer. The first way relies on synthesis and assembly of single stranded deoxynucleotide oligomers into a dsDNA monomer sequence encoding from about 1 to 12, more usually 2 to 9, frequently 2 to 6, repeating amino acid units. Each repeat unit will have about 3 to 20 codons (9 to 60 bases), generally about 3 to 15 codons, usually about 3 to 12 codons, more usually about 3 to 9 codons. The number of amino acid repeat units in a dsDNA monomer sequence will depend to a substantial degree on the size of the repeating unit. Conveniently, oligomers may be prepared having from about 15 to 120 bases, usually about 21 to 90 bases, more usually about 39 to 72 bases, although oligomers may be prepared with up to 300 bases, more usually up to about 252 bases. For repeating units having a few amino acids, usually in the range of 3 to 12 amino acids, more usually in the range of 3 to 9 amino acids, the single stranded oligomer will conveniently have from about 2 to 10 repeating units.

The number of different single stranded oligomers will usually be at least 2, forming 1 pair, more usually at least 6, forming 3 pairs, or may be 8 or more, forming 4 or more pairs, where the protein polymer has the same repeating unit. Where block copolymers are prepared, the number of oligomers will depend on the number of different blocks and the size of the blocks. Each pair of oligomers are complementary and at least partially overlap, providing blunt or cohesive (protruding) ends, preferably protruding ends, to allow for ease of assembly and ligation of the dsDNA to form a "monomer". By having a multiplicity of dsDNA segments, the termini may be designed that the first segment has a 3'terminus complementary to the 5'terminus of a second segment, and so on, where the termini may have different consensus sequences for different restriction enzymes or not be recognized by any known restriction enzyme. The dsDNA segments formed by the pairs of oligomers of the different ssDNA oligomers may encode the same amino acid sequence or a different amino acid sequence, but where more than one dsDNA segment is synthesized, at least two segments will have different nucleotide sequences. By having different termini at each end of each dsDNA segment, the individual segments cannot oligomerize, even if they have been phosphorylated. In this way, when the different segments are combined, the ends of the combination of the segments may have complementary termini, so that they can be oligomerized.

A first dsDNA segment is desirably cloned in a prokaryotic vector by linearizing a vector having an origin of replication and convenient restriction sites, which may involve a polylinker, for insertion of the dsDNA segment. The vector will also have a marker gene for selection, which will usually impart antibiotic resistance, but may afford another distinguishing characteristic, e.g. chromophore or fluorophore formation. The marker will preferably provide antibiotic resistance, there being a wide variety of antibiotic reagents, e.g. tetracycline, chloramphenicol, actinomycin, neomycin, ampicillin, hygromycin, heavy metals, etc. Other markers include β-galactosidase, which, with the substrate X-gal, provides a blue color. Numerous vectors are commercially available for cloning in *E. coli* and need not be exemplified here. The vector is then introduced into an appropriate cloning host by any convenient means, including calcium phosphate precipitated DNA, fusion, transfection, conjugation or the like. The cells are then grown in an appropriate selective nutrient medium. Surviving cells are harvested, lysed and the plasmid isolated.

After cloning, the first dsDNA segment is characterized, such as by restriction analysis and sequencing. Where the dsDNA segment is relatively small, sequencing can be performed rapidly and substantially error free.

The termini of the dsDNA segments may be selected to have protruding 5' ends, protruding 3' ends, or a protruding 5' and a protruding 3'end on the same strand, either the coding strand or the non-coding strand. Complementation of the protruding ends may destroy the sequence of the restriction site or retain the sequence, when different dsDNA segments are ligated. In selecting DNA sequences, one selects the terminal sequence to allow for linearization of the vector and insertion of the next dsDNA segment, without cleavage within the gene being formed.

Once the first dsDNA segment has been shown to have the correct sequence, the vector may then be used in the next stage in the preparation of the gene. The vector is linearized at the 5' or 3' terminus of the first dsDNA segment cloned. By employing a polylinker in the vector at the 5' and/or 3' terminus of the dsDNA segment cloned, the vector may be digested by using a restriction enzyme which cleaves in the polylinker to provide a terminus at the 5' or 3' terminus of the vector complementary to the 3' or 5' terminus of the next dsDNA segment. Alternatively, one may use restriction enzymes which cleave an asymmetric consensus sequence or cleave distal from the consensus sequence. In this way the vector may be repeatedly cleaved and ligated, without cleavage of the gene. After cloning, the combined dsDNA segments may be characterized as described above. The process may be repeated until all of the dsDNA segments have been inserted and verified for sequence and being in the proper order and reading frame. Alternatively, each dsDNA segment comprising the monomer may be individually cloned and characterized. The individual dsDNA segments are then purified and ligated in a single cloning step to construct the monomer, which is sequenced. By appropriate choice of the restriction enzymes or polylinker, the termini of the monomer may have the same or different terminal restriction sites, but will have complementary ends, if the monomer is to be multimerized.

A second approach depends on the synthesis of a single strand of the monomer. Synthetic techniques allow reasonably accurate oligonucleotide synthesis of 300 bases or more. For the most part the single strand will be in the range of about 100 to 300 bases, usually in the range of about 100 to 250 bases. The single strand is then used to produce a complementary strand, conveniently using the polymerase chain reaction ("PCR") and the resulting dsDNA cloned, purified and sequenced to ensure that it has the correct sequence. Appropriate primers may be employed, which may serve to extend the termini for multimerization by introducing a new restriction site consensus sequence, introduce intervening sequences, or the like. The monomer prepared this way will have the same limitations as to size and the number of amino acid repeating units which are encoded as the monomer prepared by the sequential or simultaneous cloning of dsDNA segments.

After the monomer has been prepared, characterized and the desired sequence confirmed, the monomer may then be excised from the vector and purified in accordance with conventional procedures. At this time the "monomer" synthesis has been completed. The monomer may then be used to produce the gene.

The third approach relies on the use of fully characterized dsDNA which is already present in a monomer, previously prepared by either of the methods described above. Using this approach allows for great flexibility in constructing new monomers, particularly where copolymers comprising different amino acid repeating units are desired. Using the appropriate restriction enzymes, all or part of the dsDNA comprising a monomer may be purified. Then, the desired dsDNA from two or more separate monomers may be combined to construct a new monomer encoding the amino acid repeating units of interest. The digested monomer DNA fragments which are to be combined may have complementary or non-complementary ends. If the termini of the monomer sequences are not complementary, as required, the termini may be made so by employing adapters, filling in, nuclease digestion, or the like. Once the appropriate monomer sequences have been cloned together, either sequentially or simultaneously, to make the new monomer, the monomer is then characterized and sequenced, if necessary. If newly synthesized adapters or filling in reactions or nuclease digestion or the like are employed, the region comprising the modified monomer DNA is sequenced.

When the protein product is a homooligomer of the monomer, desirably the termini have cohesive ends and may retain the same restriction site consensus sequence or result in a sequence other than the consensus sequence.

As evidenced by the above description, the "monomer" is a molecule having a plurality of dsDNA segments, normally having at least two different dsDNA segments, which may or may not encode the same amino acid sequence, but generally providing for blocks of the same pattern of repeat amino acid units throughout the final polymer gene. (The exception is where the monomer is the gene). Thus, the monomer may provide for a homopolymer, copolymer, or polymer having a defined motif, where the amino acid repeating units vary, e.g. collagen.

The monomer is then multimerized by ligation, conveniently employing from about 0.01 to 100 $\mu$g of the monomer under ligating conditions, where multimers having different numbers of monomers are obtained. The multimers may then be segregated by size, selecting multimers of a predetermined size. Any of the original mixture, the partially purified mixture, or size segregated fractions thereof, may then be introduced into a vector. Either an adapter vector or an appropriate expression vector is employed. The adapter vector has a polylinker which will allow for insertion into the polylinker, so as to be capable of being read in any reading frame. In this way one may introduce different unique restriction sites which allow for excision and transfer of the multimer gene from the expression vector. The multimer gene may be characterized and purified before transfer to the expression vector. If the multimer is introduced directly into the expression vector, where the terminal restriction sites are also present internally in the multimer gene, usually at the sites of ligation of the monomers, one cannot conveniently excise the multimer gene intact. One may select a particular sized multimer or a plurality of multimers of different size for expression, so that one has a family of protein polymers, sharing the same repeating motif.

The expression vector will be characterized by having an origin of replication which is functional in an appropriate expression host, usually for episomal maintenance, and a marker for selection. Markers as described above may find use. For unintegrated vectors or constructs, the origin of replication will usually provide for multicopies, usually greater than about 5 copies on the average. The expression vector will also have a promoter which is functional in the expression host. Various promoters can find use, which provide for a high level of transcription, either inducible or constitutive transcription. Illustrative promoters include β-lactamase, β-galactosidase, $\lambda P_L$ or $\lambda P_R$ promoters, trpE promoter, trp-lac promoter, T7 promoter (particularly genes 9 and 10), $cI^{ts}$, etc. The multimer gene and the linearized vector may be combined under hybridizing, usually including ligating, conditions. Where the multimer gene does not have an initiation codon, such a codon can be added. More conveniently, the multimer gene may be inserted into a coding sequence present in the vector, under the transcriptional control of a promoter. The coding sequence in the vector will generally not exceed 375 bp, usually not exceeding about 225 bp, where the site into which the multimer gene is inserted has the coding sequence and multimer gene in proper reading frame. Generally, the coding sequence present in the vector will be not more than about 20%, usually fewer than about 10%, preferably fewer than about 8% of the total number of bases in the coding sequence.

A signal sequence may be present at the 5' terminus of the coding sequence to allow for secretion of the protein polymer into the periplasmic space. Generally, the product will be produced intracellularly.

Instead of a vector, DNA constructs may be employed for transformation of the expression host, with integration of the construct into the genome of the expression host. The construct will differ from the vector primarily by lacking an origin of replication which provides for episomal maintenance. Thus, the construct will provide at least transcriptional and translational initiation and termination regions, the gene encoding the protein polymer between the initiation and termination regions and under their regulatory control, a marker for selection as described above, and other functional sequences, such as homologous sequences for integration into the host genome, sequences for priming for the polymerase chain reaction, restriction sites, and the like.

For the most part, the expression host will normally be unicellular, prokaryotic or eukaryotic, but may be from a multicellular organism. The organism may be selected from bacteria, algae, fungi, insect cells, plant cells, etc. Illustrative hosts include *E. coli, B. subtilis, B. stearothermophilus, S. cerevisiae*, and the like.

The expression host is then grown in accordance with conventional ways in an appropriate medium in culture, e.g. fermentation. After the cells have been grown to an appropriate density, the cells may be harvested, lysed and the product isolated by appropriate means, in accordance with the physical and chemical characteristics of the product. In some instances, the product is insoluble at moderate temperatures in an aqueous medium, and may be purified by detergent extraction at mildly elevated temperatures, above about 60° C. See U.S. Pat. No. 5,235,041. As appropriate, the crude or purified product may then be used for its intended purpose.

The following examples are offered by way of illustration and not with limitation.

EXAMPLE 1

DNA Preparation Methods

1. Preparation of plasmid DNA from *E. coli:*

A. Small scale: Plasmid DNA was prepared from 1.5 ml cultures by either the boiling procedure or the alkaline lysis method (Maniatis, T., Fritsch, E. F. and Sambrook, J. 1982. Molecular Cloning: A Laboratory Manual. Cold Spring Harbor Laboratory, Cold Spring Harbor, N.Y.).

B. Large scale: A plasmid-carrying strain was grown overnight in 1 liter of Luria broth with the appropriate antibiotic. The cells were collected by centrifugation at 10,000xg for 5 min and resuspended in 10 ml of ice cold TE (10 mM Tris-HCI pH 8, 1 mM EDTA). The cells were centrifuged again, resuspended in 4 ml of TES (TE and 25% w/v sucrose) and homogenized by vortexing. The samples were kept on ice for the following steps. Lysozyme (1 ml of 10 mg/ml) was added to the cell suspension and incubated for 5 min before the addition of 2 ml of 0.5M EDTA pH 8. After 10 min incubation, 50 ml of proteinase K (40 mg/ml) were added followed 10 min later with 15 ml of lysing buffer (0.1% Triton X-100, 1mM EDTA, 50 mM tris-HCI pH 8). After 15–20 min, the cell lysate was centrifuged at 35,000xg for 90–120 min. The supernatant (19.8 ml) was transferred to a plastic tube with 20 g of CsCl and 400 μl of ethidium bromide (10 mg/ml). After dissolution, the mixture was divided into two polyallomer ultracentrifuge tubes, sealed with heat and centrifuged in a Beckman Ti 65 rotor at 60,000 rpm for 24 hr. The lower plasmid DNA band was removed from the tube with a hypodermic needle. The ethidium bromide was extracted three times with an equal volume of NaCI-saturated isopropanol. Two volumes of $H_{2O}$ were added to the DNA solution, and then the DNA was precipitated with ethanol.

2. Preparation of double-stranded DNA:

A culture of JM103 was grown to an $OD_{600}$ of about 0.2 and then divided into aliquots of 2 ml. Each aliquot was infected with a fresh plaque of M13 and incubated at 37° C. for about 6 hr with vigorous shaking. Then the cells were pelleted and the supernatant was saved for subsequent infections. The double-stranded phage DNA was extracted by the boiling method (Maniatis et aL).

3. Deproteinization:

Phenol extraction was performed on a convenient volume of DNA sample, typically between 100 μl to 10 ml. The DNA sample was diluted in 0.01M Tris-HCI pH 7.5, 1 mM EDTA and an equal volume of water-saturated phenol was added. The sample was vortexed briefly and placed on ice for 3 min. After centrifugation for 3 min in a microfuge, the aqueous layer was removed to a new tube and extracted once with an equal volume of chloroform:isoamylalcohol (24:1).

4. Ethanol precipitation:

DNA in an aqueous buffer was concentrated by ethanol precipitation. To the DNA sample was added 1/10 volume of 3M sodium acetate pH 7.5 and 2–3 volumes of cold ethanol. The DNA was precipitated for 30 min at −70° C. or overnight at −20° C. and then pelleted by centrifugation in the microfuge for 15 min at 4° C. The pellet was washed once with 200 μl of cold 80% ethanol and pelleted again for 10 min at 4° C. After air drying or lyophilization, the pellets were resuspended in the appropriate buffer.

5. Phosphatase treatment of DNA:

A. Phosphatase treatment of DNA was performed by adding 1 μl (25 units) of calf intestinal phosphatase (Boehringer Mannheim) directly to the restriction enzyme digestion reaction and continuing the incubation for 30 min at 37° C. The phosphatase was inactivated for 60 min at 65° C. prior to deproteinization by phenol extraction.

B. Phosphatase treatment of DNA was also performed by resuspending ethanol precipitated DNA from the restriction enzyme digest in 20 mM Tris-HCI pH 8.0, 10 mM $MgCl_2$ to a final DNA concentration of 20 μg/ml. Shrimp alkaline phosphatase (SAP) was added at 2 U/μg of DNA and the mixture was incubated at 37° C. for one hour, heat inactivated for 20 min at 65° C. and then passed through a Probind filter (Millipore) and subsequently a Bio-Spin column. The DNA was then ethanol precipitated and resuspended in suitable buffer.

6. Phosphorylation of DNA:

Phosphorylation before annealing was performed by using Polynucleotide Kinase 3'-phosphatase-free (Boerhinger Mannheim). The reaction was carried out at 37° C. for 30 min in a 50 μl reaction volume containing: 12.5 μg DNA, 5 μl 10×kinase buffer (0.5M Tris pH 7.5, 10 mM Spermidine, 0.1 M $MgCl_2$, 150 mM DTT, 1 mM EDTA), and 2 μl Polynucleotide Kinase (10 U/μl). After phosphorylation, salts and glycerol were removed from the DNA strands using a Bio-Spin 6 column (BioRad) equilibriated in TEAB.

7. Fill-in reaction with DNA polymerase I:

DNA was resuspended in buffer containing 50 mM Tris-HCl pH 7.4, 50 mM KCl, 5 mM $MgCl_2$, and 400 μM each of the four deoxynucleotide triphosphates. Ten units of Klenow DNA polymerase (BRL) were added, and the reaction was allowed to proceed for 15 min at room temperature. The DNA was then phenol extracted and ethanol precipitated.

8. T4 polynucleotide kinase reaction:

The reaction (10 μl) contained: T4 polynucleotide kinase (BRL), 150 ng of DNA, 1 μl of 10×kinase buffer (0.7M Tris-HCl pH 7.6, 0.1M $MgCl_2$, 50 mM DTT) and [$^{32}P$]-ATP (200–300 nCi). This was incubated at 37° C. for 30 min and then the DNA was purified using a NACS column (Bethesda Research Labs).

9. Digestion with restriction endonucleases:

DNA was digested with restriction endonucleases (REN) in 1 × "AA" buffer [10×AA buffer is 330 mM Tris-acetate, pH 7.9, 660 mM potassium acetate, 100 mM magnesium acetate, 50 mM dithiothreitol (DTT) and 1 mg/ml bovine serum albumin (nuclease free)]. Whenever possible, the concentration of DNA was kept below 1 μg/25 μl. Incubation was at 37° C. for 1–4 hrs for most restriction endonucleases except for BalI, BanI and NaeI digestions which were incubated overnight.

10. Analytical agarose gel electrophoresis of DNA:

To DNA samples for gel analysis we added 0.2 volumes of loading buffer (5×electrophoresis buffer, 0.01% bromphenol blue dye, 50 mM EDTA, and 50% glycerol). Then the samples were loaded into lanes of a horizontal submerged electrophoresis unit containing a 1.0% (w/v) agarose gel. The electrophoresis buffer was either 1×TAC or ½×TBE. The 1×TAC is 40 mM Tris-base, 10 mM EDTA, adjusted to pH 7.8 with acetic acid. The ½×TBE is 0.045M Tris-base, 0.045 M boric acid, 1mM EDTA, pH 8. The gel was run at 40–50 V for 18 hr, then removed and stained with 0.5 μg/ml ethidium bromide for 30 min. The DNA bands were visualized on a long wavelength UV transilluminator.

11. Preparative agarose gel electrophoresis:

The procedures and materials are the same as for the analytical agarose gel electrophoresis. The only difference is the use of low melting point (LMP) agarose, ranging in concentration from 0.5 to 2.5% (w/v) depending on the size of the DNA fragment to be purified. DNA restriction fragments were excised from the LMP agarose gels after visualization with ethidium bromide. For agarose ligation, the buffer used was 1×TAE (50 mM Tris-acetate, pH 7.8).

12. NACS purification:

Gel fragments containing DNA were melted at 70° C. for 5 min and diluted approximately 5 fold with TE1 (10 mM Tris-HCl pH 7.5, 0.2M NaCl). The gel solution was applied to a NACS column (BRL). The column was washed with 5 ml of the same buffer. The bound DNA was eluted with 300 μl of either TE2 (10 mM Tris-HCl pH 7.5, 1.0M NaCl) for DNA fragments smaller than 1000 bp or TE3 (10 mM Tris-HCl pH 7.5, 2M NaCl) for larger fragments. The eluted DNA was concentrated by ethanol precipitation.

13. DNA ligation:

Reactions for ligating cohesive ends contained: 1 μg DNA, 1×AA buffer (see step 9, above) 1 mM ATP and 20 units of T4 DNA ligase (BRL) in a 20 μl final reaction volume. The ligation was allowed to proceed for 16–18 hr at 15° C. or 1–2 hr at room temperature. For blunt-ended ligations the reactions contained 1 μg DNA, 25 mM Tris-HCl pH 7.5, 5 mM $MgCl_2$, 5 mM DTT, 0.25 mM spermidine, 200 mg BSA, 1 mM hexamine cobalt chloride (HCC), 0.5 mM ATP and 400 units T4 DNA ligase (NEB) in a 20 μl reaction volume. The ligation was allowed to proceed for 30 min to 1 hr at room temperature.

14. Agarose DNA Ligation

The agarose was melted at 65° C., the temperature was then lowered to 37° C. and ligation buffer (5×100 mM Tris-HCl, pH 7.5, 50 mM $MgCl_2$, 50 mM DTT, 1 mM ATP) was added; the tube was then placed at room temperature and ligase was added (1000 units T4 DNA ligase (NEB)), the reaction volume was usually 50 μl. The reaction was incubated at 15° C. for 16–18 hours.

15. Use of Filters and Columns for DNA Purification.

A. Ultrafree®-Probind filter unit ("Probind", Millipore): the DNA containing solution was applied to the filter unit and spun at 12,000 RPM for 30 seconds in a Sorvall Microspin 24S.

B. Microcon-30 filter (Amicon): the DNA containing solution was washed by applying to the filter and exchanging twice with $H_2O$ by spinning at 12,000 RPM for 6 min in a microfuge.

C. Bio-Spin 6 column ("Bio-Spin", BioRad): Salts and glycerol were removed from the DNA solution by applying to the column, previously equilibrated in TEAB (triethyl ammonium bicarbonate pH 7.0), and spinning in a Sorvall RC5B centrifuge using an HB4 rotor at 2,500 RPM for 4 min.

16. Agarose DNA Purification Using Ultrafee®-MC Filter Unit:

This procedure can be used for agarose slices up to 400 μl in size. After agarose gel electrophoresis the DNA is visualized by ethidium bromide staining and the agarose block containing the DNA band of interest is excised. The agarose is then frozen at −20° C. for 1 hour; then quickly thawed at 37° C. for 5 minutes. The agarose is then thoroughly macerated. The pieces are then transferred into the sample cup of the filter unit and spun at 5,000×g in a standard microfuge for 20. The agarose is then resuspended in 200 μl of Tris-EDTA, or other buffer, and incubated at room temperature for 30 min to allow for elution of additional DNA from the gel. The mixture is then centrifuged for an additional 20 min at 10,000 RPM. The DNA is, at this point, in the filtrate tube separated from the agarose fragments and ready for subsequent DNA manipulations.

Bacterial Transformation Methods

1. Preparation of transformation-competent *E. coli cells:*

A culture of 200 ml of sterile L broth was inoculated with a small loopful of *E. coli* cells. This was incubated with shaking at 37° C. until the $OD_{600}$ was approximately 0.5. The culture was placed on ice for 10 min and centrifuged at 6,000×g for 10 min. The cell pellet was resuspended in 100 ml of ice-cold 0.1M $MgCl_2$, kept on ice for 30–40 min and centrifuged again. The pellet was resuspended in 2 ml of ice-cold 100mM $CaCl_2$, transferred to a sterile test tube and incubated on ice for 24 hr. The competent cells were then aliquoted and stored at −70° C.

2. Transformation of *E. coli:*

An aliquot of frozen competent cells were thawed on ice. To 50 μl of cells 0.1 to 1 μg of DNA was added and the mixture was incubated on ice for 30 min. The tube was removed from ice and placed in a 42° C. bath for 2 min. L broth (1 ml) was added and the transformation mix incubated with shaking at the desired temperature (usually 30° C. or 37° C.) for 2 hr. Then one-tenth of the transformation was plated on L broth plates containing the appropriate antibiotic and, when necessary, XGAL and IPTG were added.

3. DNA transformation of *B. subtilis:*

*B. subtilis* cells were grown to early stationary phase (change in Klett units of ≦5% in 15 min). Transformation followed established procedures (Anagnostopoulos et al., J. Bacteriol. (1981) 81: 741–746. Cells (0.45 ml) were incubated with 1–10 μg of DNA at 37° C. for 80 min with shaking, and then plated on TBAB agar plates with an appropriate antibiotic.

4. Isolation of plasmid DNA from *B. subtilis:*

Plasmid DNA from *B. subtilis* was obtained by a method similar to the alkalinelysis method except that pelleted cells were resuspended in 8 ml of solution 1 (50 m M glucose, 10 mM EDTA, 25 mM Tris-HCI (pH 8.0), 10 mg/ml lysozyme) and incubated at room temperature for 30 min. Then 16 ml of solution 2 (0.2 N NaOH, 1% (w/v) SDS) was added and incubated on ice for 10 min. Finally, 12 ml of 3M potassium acetate (pH 4.8) was added and incubated an additional 20 min on ice. The lysed cells were centrifuged 15 min at 15,000 rpm in a Sorval SS–34 rotor. The DNA was precipitated by adding an equal volume of isopropyl alcohol and centrifuged at 7,000 rpm. The pellet was resuspended in 5 ml of 10 mM Tris-HCl (pH 7.5), 1 mM EDTA (TE). The solution was phenol extracted once and chloroform extracted. DNA was precipitated with ethanol and resuspended in 3 ml of TE. The volume was adjusted to 5.2 ml by adding 4.2 g CsCl, 400 μl of ethidium bromide at 10 mg/ml and TE. The solution was transferred to a Beckman quickseal polyallomer centrifuge tube and centrifuged at 45,000 rpm in a Beckman vti65 rotor for 18 hr.

Antibody Production, Protein Chemistry and Electrophoresis of Proteins

1. Preparation of antibody to artificially synthesized peptides:

Synthetic peptide of sequence $(GAGAGS)_8GAAGY$ (SEQ ID NO:42) was coupled to BSA using the glutaraldehyde procedure of Kagen and Glick (1979). The degree of coupling was monitored using trace amounts of radioactive iodinated synthetic peptide. Peptide conjugates at a concentration of 1 mg/ml in complete Freund's adjuvant were used to immunize rabbits at day 0. Animals were re-injected with antigen in Freund's incomplete adjuvant at day 30 and titered at day 60. Positive sera was detected using a microtiter RIA using the synthetic peptide as antigen. Kagen and Glick (1979), in Methods of Radioimmunoassay, Jaffe and Berman (eds.), Academic Press, p 328.

A peptide of 53 amino acids corresponding to the SlpIII sequence was prepared on an Applied Biosystems peptide synthesizer. The yield of this material, which has a molecular weight of 3640 was approximately 0.5 grams. The peptide was coupled to bovine serum albumin. The material was sent to Antibodies, Inc. for preparation of antibodies in rabbits. Antisera was obtained that reacted with synthetic peptides of both the SlpI and SlpIII sequences. These antisera have been useful for the detection of fusion peptides containing gly-ala sequences.

Following the procedure described above an antigen was synthesized having the formula $(V\text{-}P\text{-}G\text{-}V\text{-}G)_8$ (SEQ ID NO:43), which was coupled to keyhole limpet hemocyanin. Polyclonal antisera was then prepared as described above which bound to the ELP peptide.

Following the same procedure, additional antigens were synthesized having the formula YTITVYAVTGRGDSPASSKPISINYC (SEQ ID NO:44) of fibronectin (the FCB portion) and the formula $(GAPGAPGSQGAPGLQ)_2YMK$ (SEQ ID NO:45) (a repeat unit of the collagen-like protein (CLP) sequence) which were coupled to keyhole limpet hemocyanin for use as immunogens. Polyclonal antisera were then prepared as described above which bound, respectively, to the FCB peptide, and to the synthetic peptide of the CLP 3.7 sequence.

2. Polyacrvlamide gel electrophoresis of proteins:

Approximately $10^9$ *E. coli* cells from growing cultures were pelleted by centrifugation at 10,000×g for 5 min. The cell pellets were resuspended in 100 to 500 μl of 2×sample buffer (100 mM Tris-HCl pH 6.8, 4% SDS, 10% β-mercaptoethanol, 60% glycerol or sucrose) and sonicated for 30 sec using a Tekmar sonic disruptor. Samples were boiled for approximately 5 min and 20 to 100 μl of the cell lysates were loaded on an SDS-polyacrylamide gel (7.5 to 16% w/v). The gels were prepared following the procedure of Laemmli, U.K. 1970. *Nature* (London), 227:680–685. The proteins in the gels were stained with 2% Coomassie brilliant blue in 10% methanol, 7.5% acetic acid for 1 hr and destained in 10% methanol, 7.5% acetic acid overnight.

3. Protein expression analysis:

An overnight culture which had been grown at 30° C. was used to inoculate 50 ml of the LB media contained in a 250 ml flask. Kanamycin was added at a final concentration of 50 μg/ml and the culture was incubated with agitation (200 RPM) at 30° C. When the culture reached an $OD_{600}$ of 0.8, 40 ml were transferred to a new flask prewarmed at 42° C. and incubated at the same temperature for approximately 2 hours. The cultures (30° C. and 42° C.) were chilled on ice and $OD_6$ was taken. Cells were collected by centrifugation and then divided in 1.0 $OD_{600}$ aliquots and used to perform western analysis using the appropriate antibodies.

4. Immunoblotting of proteins in gels:

After protein electrophoresis, one of the flanking glass plates was removed from the polyacrylamide gel. The gel surface was wetted with transfer buffer (25 mM Tris-HCl, 192 mM glycine, 20% methanol). A piece of nitrocellulose paper (Sartorius, SM11307) was saturated with transfer buffer and laid on the gel. Air bubbles between the filter and the gel were removed. The gel and nitrocellulose filter were placed in the transfer unit as specified by manufacturer (BioRad). Transfer was allowed to proceed at 200 mA for 3–4 hr. Then the nitrocellulose filter was removed and stained with Amido-Schwartz for 3 min (0.05% Amido black, 45% deionized $H_2O$, 45% methanol, 10% acetic acid) and destained in $H_2O$. The filter was incubated for at least 10 min at room temperature in "BLOTTO" (5% w/v nonfat dry milk, 50 mM Tris-HCl pH 7.4, 0.9% w/v NaCl, 0.2% w/v sodium azide). The filter was placed in serum appropriately diluted (1:50 to 1 :500) in 0.5× Blotto (2.5% nonfat dry milk, 50 mM Tris-HCl pH 7.4, 0.9% NaCl, 0.2% sodium azide) and was gently agitated for approximately 16 hr at room temperature. The filter was washed for 1 hr with 5 changes of TSA (50 mM Tris-HCl pH 7.4, 0.9% NaCl, 0.2% sodium azide). The blot was placed in 15 ml of 0.5× BLOTTO solution containing $1\times10^7$ cpm of the $^{125}I$-protein A and gently agitated for 2 hr at room temperature. The filter was washed for 2 hr with a minimum of 7 changes of TSA, rinsed once with deionized $H_2O$ and air dried. The blot was covered with Saran®wrap and autoradiographed.

An alternative to the $^{125}I$-Protein A detection method was also used. This method relied on a chemiluminescent signal activated by horseradish peroxidase (HRP). The chemiluminescent reagents are readily available from several suppliers such as Amersham and DuPont NEN. The western blot was prepared and blocked with BLOTTO. A number of methods were used to introduce the P reporter enzyme including, for example, a hapten/anti-hapten-HRP, a biotinylated antibody/streptavidin-HRP, a secondary reporter such as a goat or mouse anti-rabbit IgG-biotinylated/streptavidin-HRP, or a goat or mouse-anti rabbit IgG-HRP. These reagents were bought from different sources such as BioRad or Amersham and occasionally biotinylated antibodies were prepared in our laboratory using Biotin NHS from Vector Laboratories, Burlingame, Calif. (Cat. #SP-1200) following the procedure accompanying the product. The following is an example of a procedure used to detect the expression of protein polymers.

The blot was placed in 15 ml of BLOTTO solution containing biotinylated goat anti-rabbit IgG (BioRad) diluted in BLOTTO (1:7500) and gently agitated for 2 hrs at room temperature. The filter was then washed for 30 minutes with 3 changes of TSA (50 mM Tris-HCl pH 7.4, 0.9% NaCl, 0.2% sodium azide). The blot was then incubated for 20 minutes at room temperature with gentle rotation, in 20 ml of TBS (100 mM Tris Base, 150 mM NaCl, pH 7.5) HRP-Streptavidin (Amersham) diluted 1:1000 in TBS with 0.1% Tween 20. The blot was then washed three times for 5 minutes each in TBS with 0.3% Tween 20 and then three times for 5 minutes each in TBS with 0.1% Tween 20. The blot was then incubated for 1 minute with gentle agitation in 12 ml of development solutions #1 an #2 (Amersham) equally mixed. The blot was removed from the development solution and autoradiographed.

5. Protein expression analysis

An overnight culture which had been grown at 30° C. was used to inoculate 50 ml of LB media contained in a 250 ml flask. Kanamycin was added at a final concentration of 50 μg per ml and the culture was incubated with agitation (200 rpm) at 30° C. When the culture reached an $OD_{600}$ of 0.8, 40 ml were transferred to a new flask prewarmed at 42° C. and incubated at the same temperature for approximately 2 hours. The cultures (30° and 42°) were chilled on ice and $OD_{600}$ was taken. Cells were collected by centriflugation and then divided in 1.0 $OD_{600}$ aliquots and used to perform western analysis using the appropriate antibodies.

6. Amino Acid Analysis:

Amino acid compositions are determined by the PTC derivitization procedure of Henrickson and Meredith (1984). Protein samples were hydrolysed with 5.7N constant boiling HCl at 108° C. for 24 hours in vacuo. After reaction with PITC, amino acid derivatives were detected at 254 nm by HPLC reverse phase chromatography using a Hewlett Packard 1090 or Waters 600E system and a Supelco C18 column (4.6 mm×25 cm) with a linear gradient of 0–50% acetonitrile in 0.1M $NH_4OAc$ pH 6.78 as a mobile base. Henrickson, R. L. and Meredith, S.C. (1984) Amino Analysis by Reverse Phase High Performance Liquid Chromatography. *Anal. Biochem.* 137:65–74.

7. Amino Acid Sequence Analysis:

The N-terminal amino acid sequence was determined by automated Edman degradation using an Applied Biosystems Model 470A gas phase protein sequenator. The PTH amino acid derivatives were analyzed by reverse phase HPLC using a Hewlett Packard 1090 or Waters 600E system and an Altex C 18 column (2 mm×25 cm) with a complex gradient buffer system.

8. Peptide Synthesis:

Synthetic peptides were prepared by solid phase synthesis on an Applied Biosystems Model 430A Peptide Synthesizer using the standard symmetric anhydride chemistry as provided by the manufacturer. The coupling yield at each step was determined by the quantitative ninhydrin procedure of Sarin et al., (1981). The synthetic peptide was cleaved from the solid support and amino acid blocking groups were removed using anhydrous HF (Stewart and Young, 1984). Crude peptides were desalted by chromatography over Sephadex G-50. Sarin, V. K., Kent, S. B. H., Tam, J. P. and Merrifield, R. B. (1981). *Anal. Biochem.* 237:927–936. Stewart, J. M. and Young, J. D. (1984). Solid Phase Peptide Synthesis, Pierce Chemical Company, Rockford, Ill. pp 85–89.

Synthetic peptides were also prepared on a Rainin/ProteinTechnologies PS3 FMOC peptide synthesizer. Both the synthesis and the cleavage were accomplished using methods supplied by the manufacturer in the instrument manual.

Synthetic DNA Methods

1. In vitro DNA synthesis:

The N,N-diisopropylphosphoramidites or β-cyanoethyl phosphoramidites, controlled-pore glass columns and all synthesis reagents were obtained from Applied Biosystems, Foster City, Calif.

Synthetic oligonucleotides were prepared by the phosphite triester method with an Applied Biosystems Model 380A or 381A DNA synthesizer using a 10-fold excess of protected phosphoramidites and 1 μmole or 0.2 μmole of nucleotide bound to the synthesis support column. The chemistries used for synthesis are the standard protocols recommended for use with the synthesizer and have been described (Matteucci, et al, *Journal Amer. Chem. Soc.,* 103:3185–3319 (1981)). Deprotection and cleavage of the oligomers from the solid support were performed according to standard procedures as described by McBride, et al., Tetrahedron Letters. 24:245–248 (1983). The repetitive yield of the synthesis as measured by the optical density of the removed protecting group as recommended by Applied Biosystems (1984) was greater than 97.5%.

The crude oligonucleotide mixture was purified by preparative gel electrophoresis as described by the Applied Biosystems protocols of Nov. 9, 1984 (User Bulletin No. 13) and as updated in 1992. The acrylamide gel concentration varied from 10 to 20% depending upon the length of the oligomer. If necessary, the purified oligomer was identified by UV shadowing, excised from the gel and extracted by the crush and soak procedure (Smith, *Methods in Enzymology* 65:371–379 (1980)).

For DNA synthesis of oligonucleotides longer then 100 bases, the synthesis cycle was changed from the protocol recommended by Applied Biosystems for the 381A DNA synthesizer. All the reagents used were fresh. All the reagents were supplied by Applied Biosystems except for the acetonitrile (Burdick and Jackson Cat#017-4 with water content less then 0.001 %) and the 2000 Å pore size column (Glen Research). Due to the length of the oligo, interrupt pauses had to be inserted during the synthesis to allow changing the reagent bottles that emptied during synthesis. This interrupt pause was done at the cycle entry step and the pause was kept as short as possible. The washes after detritylation by TCA, through the beginning of each synthesis cycle, were increased from about 2×to 3× over the recommended time. The time allocated for the capping was also increased to limit truncated failure sequences. After the synthesis the deprotection was done at 55° C. for 6 hours. After desalting the synthesized DNA was amplified using PCR.

2. Sequencing of DNA:

DNA sequences were determined by the following methods. Fragments containing the region of interest were cloned into the multiple cloning site of M13mp18 or M13mp19 (Maniatis et al., 1982, and Norrander et al. 1983. *Gene.* 26:101–106). Single-stranded DNA was prepared and sequenced by the primer extension method (Sanger et al. 1977 *Proc. Natl. Acad. Sci. USA* 74:5463–5467 and Biggin et al., 1983 1983. *Proc. Natl. Acad. Sci.USA* 80:3963–3965) using $^{35}S$-deoxyadenosine 5'-(alpha-thio)-triphosphate (New England Nuclear) as label. In some cases, reverse transcriptase (Molecular Genetics) was used to extend the primer, using the dideoxy:deoxynucleoside tri-phosphate ratios utilized by Zagursky et al. Gene Anal. Techn. (1985) 2:89–94. Deoxyadenosine triphosphate labeled with either $^{32}P$ or $^{35}S$ was used in these reactions. Compression artifacts which appeared in some G-C rich sequences were overcome by eliminating deoxyguanosine triphosphate from the G reaction, and using deoxyinosine triphosphate (P-L Biochemicals) at a final concentration of 37.5 $\mu$M instead. In the other mixes, the concentration of dideoxyGTP in the G reaction was 0.5 mM. All sequences were run on 6 or 8% polyacrylamide gels containing 8M urea (Sanger et al. 1978, *FEBS Letters*. 87:107–110.). Primers used for sequencing were purchased from P-L Biochemicals. Storage and analysis of data utilized software from both DNAstar and International Biotechnologies, Inc for IBM personal computer and DNA Strider, DNA Inspection IIe or DNAid for Apple Macintosh personal computer.

3. In vitro mutagenesis of cloned DNA:

Plasmid DNA (1 $\mu$g) containing the sequence to be mutated was digested in two separate reactions. One reaction contained either one or two restriction endonucleases which cleave at sites immediately flanking the region of interest. In the second reaction, the DNA was digested with a restriction endonuclease which cleaves only once at a site distant from the sequence to be mutated. The DNA fragments generated in the first reaction were separated by agarose gel electrophoresis and the large fragment which lacks the sequence to be mutated was excised and purified. DNA from the second reaction, the large fragment of DNA from the first reaction, and a synthetic oligodeoxynucleotide of 20–30 bases in length containing the mutant sequence were mixed in a molar ratio of 1:1:250. The mixture was denatured by heating at 100° C for 3 min in 25 to 100 $\mu$l of 100 mM NaCl, 6.5 mM Tris-HCl pH 7.5, 8 mM $MgCl_2$, and 1 mM β-mercaptoethanol. The denatured mixture was reannealed by gradually lowering the temperature as follows: 37° C. for 30 min, 4° C. for 30 min, and 0° C. for 10 min. The reaction was supplemented with 0.5 mM deoxyribonucleotide triphosphates, 1 mM ATP, 400 units of T4 DNA ligase and 5 units of *E coli* DNA polymerase large fragment and incubated at 15° C. for 12–16 hr. The reaction mixture was then transformed into *E. coli* and antibiotic-resistant colonies were selected.

4. Dideoxy DNA Sequencing of Double Stranded Plasmid DNA:

Plasmid DNA was prepared as described previously (Preparation of plasmid DNA from *E.coli*, Small Scale, Maniatis et al.). Primers were synthesized using a DNA synthesizer as described previously, and were annealed to the plasmid DNA following the procedure described above for M13 sequencing. The sequencing reactions were done using Sequenase (United States Biochemicals) and the conditions were as recommended by the supplier. All sequences were run on polyacrylamide gels as described above.

5. PCR amplification:

The PCR reaction was performed in a 100 $\mu$l volume in a Perkin Elmer thin-walled Gene Amp™ reaction tube. Approximately 1 $\mu$l of each primer DNA (corresponding to a 0.1 $\mu$M final concentration) was added to 1× PCR buffer (supplied by Perkin Elmer as 10× solution), 200 $\mu$M of each dNT, 5U AmpliTaq, and several concentrations of the target DNA. Amplification was performed in a Perkin Elmer DNA Thermal cycler model 480 for 30 cycles with the following step cycles of 12 min each: 95° C., 62° C., and 72° C. Aliquots from the different reactions were analyzed by Agarose Gel Electrophoresis using 1.5% Low Melting Point agarose in 0.5× TA buffer. The reaction mixtures that gave the desired band were pooled and spun through an Ultrafree-Probind filter unit (Millipore) at 12,000 rpm for 30 seconds in a Sorvall Microspin 24S to remove the AmpliTaq enzyme. The buffer was then exchanged with $H_2O$ two times, using a Microcon-30 filter (Amicon) by spinning at 12,000 RPM for 6 min in a microfuge. Salts and glycerol were removed from the amplified dsDNA using a Bio-Spin 6 column (from BioRad) equilibrated in TEAB, in a Sorvall RC5B centrifuge using an HB4 rotor at 2,500 RPM for 4 min. The DNA was then concentrated in vacuo.

Fermentation Conditions

The fermentor is a 15 L Chemap, 10 L working volume. The culture conditions are: temperature=30° C., pH 6.8;NaOH 2.5M is used for pH regulation. The headspace pressure is below 0.1 bar. The dissolved oxygen is regulated at 50%. The air flow varies from 0.5 L/min to 20 L/min. The agitation rate varies between 200 to 1500 rpm. The fermentor is inoculated with a 10% (v/v) inoculum grown in medium A for 15 hours at 30° C. under agitation.

Medium B, C or D was the fermentor medium. The starting volume in the case of 10 liter fermentation, is no less than 3 L, and in the case of a 1 liter fermentation, is no less than 0.5 liters.

If the fermentor starting volume is less than the final volume desired, then when the carbon source concentration reaches 1%, a concentrated solution (5×) of medium B,C, or D, respectively, is added to the fermentor in order to keep the carbon source concentration approximately 1%.

When the culture reached an $OD_{600}$ of 60.0, the temperature was increased to 42° C. for 10 min, then lowered to 39° C. or 40° C. for 2 to 3 hours. The cells were then harvested by centrifugation and frozen at −70° C. until processed.

Other fermentors used for the expression of protein polymers were usually a 15 l MBR, 10 l working volume, or a 13 l Braun Biostat E, 8.5 l working volume. The choice of the fermentor and its size is not critical. Any media used for the growth of *E. coli* can be used. The nitrogen source ranged from NZAmine to inorganic salts and the carbon source generally used was glycerol or glucose. All fermentations were done with the appropriate selection conditions imposed by the plasmid requirements (e.g. kanamycin, ampicillin, etc.). The fermentation method used to express protein polymers in *E. coli* was the fed-batch method. This is the preferred method for the fermentation of recombinant organisms even if other methods can be used.

The fed-batch method exploits the stage of cell growth where the organisms make a transition from exponential to stationary phase. This transition is often the result of either depletion of an essential nutrient or accumulation of a metabolic byproduct. When the transition is the result of nutrient depletion, the addition of nutrients to the system causes cell division to continue. One or more essential nutrients can incrementally be added to the fermentation vessel during the run, with the net volume increasing during the fermentation process. The result is a controlled growth rate where biomass and expression levels can be optimized. When the cell number in the culture has reached or is approaching a maximum, protein polymer production is induced by providing an appropriate physical or chemical signal, depending upon the expression system used. Production will then continue until the accumulated product reaches maximum levels (Fiestchko, J., and Ritch, T., *Chem. Ens. Commun.* 1986, 45: 229–240. Seo, J. H.; Bailey, J. E., Biotechnol. Bioeng. 1986, 28: 1590–1594.

TABLE 1

| Medium Table | |
|---|---|
| Constituent | g/L |
| **Medium A: LB Medium** | |
| NaCl | 10 |
| tryptone | 10 |
| yeast extract | 5 |
| kanamycin | $5 \times 10^{-3}$ |
| **Medium B** | |
| $NH_4Cl$ | 4.5 |
| $KH_2PO_4$ | 0.76 |
| $MgSO_4.7H_2O$ | 0.18 |
| $K_2SO_4$ | 0.09 |
| $CaCl_2$ | $24 \times 10^{-3}$ |
| $FeSO_4.7H_2O$ | $7.6 \times 10^{-3}$ |
| TE | 0.5 ml |
| casamino acids | 25 |
| yeast extract | 5 |
| glucose | 20 |

TABLE 1-continued

| Medium Table | |
|---|---|
| Constituent | g/L |
| kanamycin | $5 \times 10^{3}$ |
| **Medium D** | |
| $(NH_4)SO_4$ | 5.6 |
| $K_2HPO_4$ | 6.7 |
| $MgSO_4.7H_2O$ | 7.8 |
| $NaH_2PO_4.H_2O$ | 3.8 |
| EDTA | 0.98 |
| Trace Elements | 1 ml |
| Yeast Extract or NZ Amine | 50 |
| Glucose or glycerol | 20 |
| Kanamycin or ampicillin | $5 \times 10^{-3}$ |

EXAMPLE 2

Assembly and Expression of the SlpI Gene

1. Summary of the scheme for assembling the SlpI gene:

An 18 bp DNA sequence that codes for the most frequent repeating oligopeptide in the silk fibroin protein made by *Bombyx mori* [Lucas, F. and K. M. Rudall (1986) Extracellular Fibrous Proteins: The Silks. p. 475–558, in Comprehensive Biochemistry, vol. 26, part B., M. Florkin and F. H. Stotz (eds.) Elsevier, Amsterdam] was synthesized in vitro. Two single-strands were synthesized, annealed together and then the resulting double-stranded segments were multimerized head-to-tail to generate concatamers of up to and exceeding 13 repeats. The structural gene for silk I that we proceeded to work with had 13 repeats that coded for the oligopeptide GAGAGS (SEQ ID NO:41), where g=glycine, a=alanine and s=serine. We refer to this structural gene as the “monomer”. We constructed “dimeric, trimeric, tetrameric, pentameric and hexameric” SlpI genes containing 26 (SlpI-2), 39 (SlpI-3), 52 (SlpI-4), 65 (SlpI-5) and 78 (SlpI-6) repeats. There is a short intervening sequence between each monomer unit. The assembly is pictured as follows:

Repeating DNA Sequence 5'-GGTGCGGGCGCAGGAAGT (SEQ ID NO: 46)
CGCCCGCGTCCTTCACCA-5' (SEQ ID NO: 47)

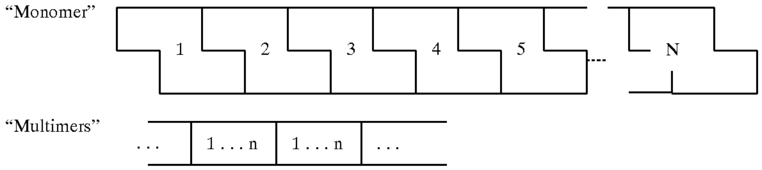

2. Assembly of the “monomeric” SlpI structural gene:

The two single-strands shown above were synthesized as previously described. The strands were separately purified by gel electrophoresis, phosphorylated using T4 polynucleotide kinase and then mixed together and allowed to anneal. This resulted in the double-stranded segments aligning spontaneously head-to-tail in long concatamers. The phosphodiester bonds between segments were formed with T4 DNA ligase. The reaction was stopped by filling in the terminal cohesive ends using the Klenow fragment of DNA polymerase I. The blunt-ended repeating DNA was then ligated to the HincII REN site in plasmid vector pUC 12 (Veiera, et al., *Gene* 19:259–268 (1982)). The ligated DNA was transformed into *E coli* HB101 and transformants were selected for their ability to grow in the presence of ampicillin. The DNA of potential clones was analyzed; for size and orientation by REN digestion and gel electrophoresis. DNA sequences were determined for isolates with large inserts that were oriented properly. The “monomer” clone selected for subsequent multimerization had 13 repeats coding for the oligopeptide AGAGSG (SEQ ID NO:48), and was named pSY708. The DNA sequence, deduced amino acid sequence and REN sites of the SlpI insert and flanking regions of pSY708 are shown in Table 2.

TABLE 2

```
H        P        A S
I        S        V M
N        T        A A
3        1        1 1
|        |        | |
|        |        | |
AAGCTTGGGCTGCAGGTCACCCGGGCGGGCGCAGGAAGTGGTGCGGGCGCAGGAAGTGGT
TTCGAACCCGACGTCCAGTGGGCCCGCCCGCGTCCTTCACCACGCCCGCGTCCTTCACCA 60
K  L  G  L  Q  V  T  R  A  G  A  G  S  G  A  G  A  G  S  G

GCGGGCGCAGGAAGTGGTGCGGGCGCAGGAAGTGGTGCGGGCGCAGGAAGTGGTGCGGGC
CGCCCGCGTCCTTCACCACGCCCGCGTCCTTCACCACGCCCGCGTCCTTCACCACGCCCG 120
A  G  A  G  S  G  A  G  A  G  S  G  A  G  A  G  S  G  A  G

GCAGGAAGTGGTGCGGGCGCAGGAAGTGGTGCGGGCGCAGGAAGTGGTGCGGGCGCAGGA
CGTCCTTCACCACGCCCGCGTCCTTCACCACGCCCGCGTCCTTCACCACGCCCGCGTCCT 180
A  G  S  G  A  G  A  G  S  G  A  G  A  G  S  G  A  G  A  G

AGTGGTGCGGGCGCAGGAAGTGGTGCGGGCGCAGGAAGTGGTGCGGGCGCAGGAAGTGGT
TCACCACGCCCGCGTCCTTCACCACGCCCGCGTCCTTCACCACGCCCGCGTCCTTCACCA 240
S  G  A  G  A  G  S  G  A  G  A  G  S  G  A  G  A  G  S  G

                    X     B     A S         E
                    B     A     V M         C
                    A     M     A A         R
                    1     1     1 1         1
                    |     |     | |         |
                    |     |     | |         |
GCGGGCGCAGGAAGTGGGACTCTAGAGGATCCCCGGGCGAGCTCGAATTC
CGCCCGCGTCCTTCACCCTGAGATCTCCTAGGGGCCCGCTCGAGCTTAAG           290
A  G  A  G  S  G  T  L E  D  P  R  A  S  S  N  S

(SEQ ID NOS: 49 & 50)
```

3. Construction of the expression vector, pSY701:

Plasmid pSP65 (10 μg, Boehringer Mannheim) was digested with AatII REN, phenol extracted and ethanol precipitated. The DNA was resuspended in 10μl of $H_2O$. One-half of this DNA was digested with exonuclease III in the following mix: 5 μg DNA, 10 μl 10X exonuclease III buffer (600 mM Tris-HC1 pH 8.0, 6.6 mM $MgCl_2$, 10 mM β-mercaptoethanol) and 9 units of exonuclease III in a total volume of 200 μl. Samples of 20 μl were taken at 0, 1, 2.5, 5 and 7.5 min and diluted immediately in 100 μl of the following buffer (30 mM sodium acetate, pH 4.5, 0.25M NaCl, 1 mM $ZnSO_4$) containing 5 μg tRNA and 36 units of S1 nuclease. Incubation was at 30° C. for 45 min and then the reaction was terminated by the addition of 15 μl of stop buffer (0.5M Tris pH 9.0, 125 mM EDTA, 1% w/v SDS, 200 μg/ml tRNA). The samples were phenol extracted and ethanol precipitated. The resuspended DNA was digested with SmaI REN and electrophoresed through a 1% gel of low melting point agarose. The gel band corresponding to the DNA fragment carrying the β-lactamase gene, the plasmid origin and the β-galactosidase promoter was excised from the gel and melted at 65° C. One volume of $H_2O$ was added. The DNA in each sample (timepoint) was recircularized by ligation in the presence of agarose. The reaction included 8 μl melted gel, 2 μl of ligation buffer (100 mM Tris-HCl pH 7.5, 50 mM $MgCl_2$, 50mM DTT, 1mM ATP), 10 units T4 DNA ligase and was incubated at 15° C. for 3 hr. Competent cells of JM1O1 were transformed with the ligated DNA and transformants were selected by growth on L broth plates containing ampicillin (40 μg/ml). Plasmid DNA was prepared from four transformants. The DNA was digested with BamHI REN, labeled with $^{32}$P-dGTP using the Klenow fragment of DNA Polymerase I, digested with Pvu I and then the smallest fragment was gel purified. The fragment from one transformant was sequenced using the Maxam and Gilbert technique. The fragments of the other three plasmids were further digested with TaqI and electrophoresed on the same gel. The sequenced plasmid had a fusion between the multiple cloning site and a position upstream from the N-terminal ATG of β-lactamase. The size of the BamHI-TaqI fragment of two of the other plasmids indicated a fusion between the multiple cloning site and the 4th amino acid of the β-lactamase gene. The DNA and corresponding amino acid sequences of the N-terminal region of the altered β-lactamase, along with a circular map of REN sites for pSY701, are shown in FIG. 1. The aminino acid sequence of FIG. 1 is met-thr-met-ile-thr-pro-ser-leu-gly-cys-arg-ser-thr-leu-glu-asp-pro-his-phe-arg-val-ala-leu-lie-pro- phe-phe-ala-ala-phe-cys-leu-pro-val-phe-ala-his-(SEQ ID No:51).

4. Insertion of "monomer" SlpI From pSY708 into pSY701:

Plasmid pSY708 was digested with Hind III, the cohesive ends were filled in using the Klenow fragment of DNA polymerase I and then digested with BamHI. Plasmid pSY701 was digested with XbaI, filled in as above and then digested with BamHI. The DNA fragment from pSY708 and the backbone of pSY701 were then purified by electrophoresis through a low melting temperature agarose gel and purified with NACS (BRL) columns. The appropriate fragments were mixed, ligated, and then transformed into *E. coli* JM 109. Transformed cells were selected by growth on L plates containing ampicillin (40 mg/ml), IPTG ($5\times10^{-4}$ M) and XGAL (20 mg/ml). Transformants were analyzed for plasmid contents and one (pSY756) was selected for further study since it carried the insert of the monomer SlpI-1 sequences in the proper orientation, as determined by mapping of REN sites. Although the entire DNA sequence was not determined for pSY756, the junctions between the insert and vector were verified as correct restriction sequences for XbaI, upstream and BamHI, downstream.

5. Multimerization of the SlpI gene of pSY756:

Plasmid pSY708 was digested with the REN SmaI and the DNA fragment carrying the coding sequence for the polypeptide arg(ala-gly-ala-gly-ser-gly)$_{13}$ thr-leu-glu-asp-pro (R(AGAGSG)$_{13}$TLEDP) (SEQ ID NO:52) was purified as in 4 above. Plasmid pSY756 was digested with SmaI, deproteinized and then ligated with the purified DNA fragment from pSY708. Transformants of *E. coli* JM109 were selected on medium containing ampicillin. Clones were found to contain 2 units (dimer pSY882), 3 units (trimer pSY883), and 4 units (tetramer pSY915) of the original monomer sequence of the pSY708 clone. Similarly, pentamers and hexamers have also been constructed. All of these plasmids are genetically stable and produce the gly-ala peptide as a fusion with β-lactamase.

6. Expression of the SlpI gene fusion to the β-lactamase protein:

Synthesis in *E. coli* cells of the SlpI peptide as a fusion protein with β-lactamase was detected by immunoblotting (Western) analysis. Anti-"Slp" antibodies were raised against a synthetic silk peptide. Fusions between β-lactamase and SlpI were also detected with antibodies raised against the *E. coli* β-lactamase. As shown in FIG. 2, this antibody reacts with dimers and trimers of SlpI fused to the *E. coli* β-lactamase. The SlpI insert precedes the fifth amino acid of the signal sequence for this enzyme. The β-lactamase antibody (FIG. 2A) detects both the unprocessed fusion proteins as well as the processed mature enzyme which appears as the major antigenic band in this figure, at about the 28 kDal position. The mobilities of all Slp-containing polypeptides are anomalously slow and the proteins are not as large as they appear on the gels.

The anti-SIp antibody also is useful in detecting these fusion products. Lanes 2–5 of FIG. 2B represent 4 separate clones that contain dimer fusions of SlpI with β-lactamase, while lanes 6 and 7 are from two clones containing trimer fusions. As can be seen the antigenicity of the trimer is considerably greater than for the dimer. It is known from prior experiments that fusion proteins containing only a monomer of SlpI are not detected at all with this anti-SIp antibody. The increased antigenicity of the trimer peptide allows it to be detected as a processed fusion with the β-lactamase signal peptide. The processed form is seen at about the 33 kDal position in lanes 6 and 7 of FIG. 2B. The appearance of normally processed β-lactamase mature enzyme (detected with β-lactamase antibody) as well as a peptide corresponding to the fusion between the SlpI-3 trimer and the signal peptide of β-lactamase (detected with gly-ala antibody) suggests that despite the insertion of SlpI sequences within the signal sequence, normal proteolytic processing of the enzyme occurs in *E. coli.*

7.a. Expression of the SlpI gene bv fusion to T7 genes:

The SlpI sequence has also been expressed as a fision protein with both the gene 9 and gene 10 proteins from bacteriophage T7 in *E.* coli. The construction is diagrammed in FIG. 3. Plasmid pSY915 (containing the SlpI-4 tetramer) was digested to completion with REN SalI and partially with BamHI. The DNA fragment containing the SlpI-4 tetramer was purified and then cloned in plasmid pSY114 (pG2 of Promega Biotech) which had been digested with RENs SalI and BamHI. From this intermediate plasmid, the tetramer insert of SlpI was removed with the RENs AccI and EcoRI. This fragment was then cloned in pSY633 (pBR322 containing the complete T7 gene 9 sequence, pAR441 of Studier, W. F. and Moffat, B.A. 1986. *J. Mol. Biol.* 189:113–130, which was digested with EcoRI and AsuII. In the resulting plasmid the SlpI tetramer is fused to the gene 9 translational reading frame near the C-terminus of gene 9. This plasmid was then used to transform *E coli* strain 0–48 (strain HMS 174 (λDE3) of Studier, et al. , 1986) which contains the T7 RNA polymerase gene inserted into the chromosome under transcriptional control of the IPTG-inducible β-galactosidase promoter. In this configuration, expression of the SlpI-4 sequence is dependent upon production of the T7 RNA polymerase which itself is controlled by the IPTG inducible β-galactosidase promoter. As shown in FIG. 4B and 4C, when these cells are induced with IPTG a protein product of the gene 9/SlpI-4 fusion gene is synthesized and is detected with antibody to the synthetic Slp peptide. The fusion product migrates in the gel as if it was 82 kDal in size. The size expected is only 65 kdal. The anomalous mobility is characteristic of the unusual amino acid composition (rich in glycine and alanine) and is seen for all Slp-containing products.

In like manner, plasmid pSY638 (pAR2113 of Studier) containing the promoter region and the first 13 amino acids of the T7 gene 10 protein, was digested with REN BamHI, filled in with the Klenow fragment of DNA polymerase and then digested with REN EcoRI. Into this linearized plasmid was cloned the AsuII-EcoRI fragment of pSY633, containing the SlpI-4 tetramer. This ligation creates an in-frame fusion of the silk tetramer following the thirteenth amino acid of T7 gene 10. The latter fusion product may be used for spinning without further processing since the N-terminal 13 amino acids are only a small part of the large SlpI protein. Although the fusion product is about 30 kDal in size, it has an anomalous mobility and migrates as if it was larger, 50 kDal. This is shown in FIG. 4A.

The plasmids pG9/SlpI-4 and pG10/SlpI-4 were further improved by inserting a kanamycin-resistance gene in the β-lactamase gene in the orientation opposite to the T7 expression system. Thus, any low level expression from the T7 system does not lead to elevated β-lactamase activity. Such activity eliminated the ampicillin in the medium that was added to select for maintenance of the plasmid. When the ampicillin was depleted the plasmids were lost from the culture. The kanamycin-resistance gene circumvents this problem and represents a significant improvement in the T7 expression system, especially for large scale cultures. The kanamycin-resistance gene (originally from Tn903) was isolated from a plasmid pUC4K (Veira, J. and Messing, J. 1982. *Gene.* 19:259–268) as a HincII fragment. The fragment containing pG10/Slp1–4 and the Kanamycin -resistance gene was designated pSY997.

7.b. Fermentation and purification of SlpI-4:

*E. coli* strain 0–48 carrying pSY997 was grown at 37° C., using a Chemap or a Braun fermentor, in 10 L of LB to an OD (Klett units) of 300 ($3\times10^9$ cells/ml). The T7 system was then induced with the addition of 3.5 mM IPTG. After 150 min the cells were concentrated 10×using a Millipore filter unit (Pellicon cassette system, 100,000 molecular weight cut off filter). The cell suspension was then frozen at −70° C. until processing.

The cell suspension was melted in a water bath at 42° C. and lysed in a french press, and the lysate was spun at 125,000×g for 1 hour at 25° C. The cleared supernatant was treated with DNAase (250 μm/ml) for 15 min at room temperature, then filtered through a 0.45 μm sterile filter. The filtrate volume was measured and incubated in ice with slow stirring. Then 231 mg of ammonium sulphate were added for each ml of filtrate over a period of 45 min. One ml of NaOH for each 10 g of ammonium sulphate was added to neutralize the pH.

After b 2hours of continuous stirring the mixture was spun at 9,000×g for 10 min. The pellet was resuspended in 1/10 of the original filtrate volume using distilled water. The centrifugation and resuspension was repeated three times. The pellet was resuspended in 1/10 of the original filtrate volume in distilled water. Samples were analyzed for protein concentration, amino acid composition and protein sequence by standard methods. This is one of several methods for obtaining the product. This method results in a SlpI-4 product that is greater than 90% pure. The amino acid composition was almost entirely gly, ala and ser, as expected, and the N-terminal amino acid sequence is that of the gene 10 leader.

8. Controlled expression of the T7 RNA polymerase gene in *Bacillus subtilis:*

The coding sequence of the T7 RNA polymerase gene (T7 gene 1, T7 nucleotides 3128 to 5845) from plasmid pSY558 (pARI 151 of Studier, et al., 1986) was modified by in vitro mutagenesis of cloned DNA. We inserted the recognition sequence for the restriction endonuclease NdeI at position 3171. Using an oligodeoxynucleotide which was synthesized as previously described, the T7 gene 1 sequence was changed from its natural sequence, TAAATG (SEQ ID NO:53), to the modified sequence, CATATG (SEQ ID NO:54).

Similarly, the upstream regulatory sequence of the *Bacillus subtilis* gene spoVG, obtained from plasmid pCB1291 (Rosenblum, etal., *J. Bacteriology,* 148:341–351 (1981)) ,was modified by in vitro mutagenesis at position 85 (Johnson, et al., *Nature,* 302:800–804 (1983)) such that it also includes an NdeI cleavage site. The upstream regulatory sequences of the spoVG gene were then ligated with the coding sequence of the T7 RNA polymerase gene via these novel NdeI cleavage sites. After transformation of *E. coli HB* 101, the plasmid contents of individual ampicillin-resistant isolates were checked by restriction mapping. The correct construction was named pSY649.

Plasmid DNA containing the spoVG:T7 RNA polymerase fusion gene (pSY649) was further modified to include a chloramphenicol-resistance gene that functions in *B. subtilis*. First the NdeI to SalI fragment of about 1200 base pairs from plasmid pGR71-P43 (Goldfarb, et al., *Nature,* 293:309–311 (1981)) was isolated. This fragment carries the P43 promoter of *B. subtilis* and an adjacent chloramphenicol acetyltransferase gene from Tn9. After filling in all the cohesive ends using the Klenow DNA polymerase reaction, this fragment was inserted into the XbaI site within the multiple-cloning site of pUC13 (Veiera, et al., *Gene.* 19:259–268 (1982)). Ampicillin and chloramphenicol-resistant transformants were selected for further use. The correct plasmid construction was named pSY630. The SmaI to HincII endonuclease cleavage fragment from plasmid pSY630 containing the chloramphenicol acetyltransferase gene fused to the P43 promoter sequence was gel purified and blunt-end ligated to the PvuI site of plasmid pSY649 that had been treated first with T4 DNA polymerase. The resulting plasmid, pSY856, was then transformed into *B. subtllis* I168. Because plasmid pSY856 is unable to replicate autonomously in *B subtilis*, stable transformants resistant to chloramphenicol must result from the integration of the plasmid into the *B. subtilis* chromosome (Ferrari, et al., *J. Bacteriology,* 154:1513–1515 (1983)). The integration event, facilitated by homologous recombination, most likely occurred at either the spoVG or the P43 loci of the bacterial chromosome (pSY856 contains DNA sequences homologous to the *B subtilis* chromosome at only these two sites). The resulting strain, "BlPol," was grown both in the presence and absence of chloramphenicol in order to determine the stability of the selectable marker. Expression of the T7 polymerase was obtained and this has no apparent effect on the growth or viability of this strain.

9.a. Expression of a plasr aid-borne target gene (kanamycin-resistance) in *B. subtilis* strain BlPol:

The *Staphylococcus aureus* plasmid pUB110 (Lacey, et al. , *J. Med. Microbiology,* 7:285–297, 1974) which contains the gene coding for resistance to the antibiotic kanamycin was used to test the expression of the growth-regulated spoVG:T7 RNA polymerase gene of strain BlPol. An EcoRI-BamHI fragment of phage T7 DNA (positions 21,402 to 22,858) containing the T7 gene 9 promoter sequence was purified from plasmid pAR441 (Studier, et al., 1986). This DNA fragment was ligated into pUB110 between the EcoRI and BamHI restriction endonuclease sites. The resulting plasmid, pSY952, contains the T7-specific promoter in the same orientation as the kanamycin-resistance gene. Plasmid pSY952 was transformed into *B. subtilis* 1168 and B1Pol and these strains were analyzed for the level of expression of the polypeptide encoded by the plasmid derived kanamycin-resistance gene. Approximately $10^9$ cells from growing cultures of 1168, 1168 containing pUB110, 1168 containing pSY952, B1Pol, B1Pol containing pUB110, and B1Pol containing pSY952 were obtained at several times during the growth and sporulation cycle. The proteins in these cell samples were processed and analyzed by polyacrylamide gel electrophoresis.

Because the rate of transcription from the spoVG promoter increases as a function of cell density and reaches a maximum during early sporulation, an accelerated accumulation of the target protein is expected in the B1Pol strain containing pSY952 during growth as the culture enters sporulation. The results show that a protein of molecular weight 34 kDal increases in abundance as the culture approaches and enters stationary phase. The size of the protein is in agreement with the predicted size of the kanamycin-resistance gene product (Sadaie, et al., *J. Bacteriology.* 141: 1178–1182 (1980)) encoded in pSY952. This protein is not present in B1Pol or 1168 containing pSY952 which lacks the spoVG-regulated T7 RNA polymerase gene or in B1Pol containing pUB 110 which lacks the T7 promoter sequence. The maximum accumulated level of target protein after 24 hours of growth in B1Pol containing pSY952 was 20% of the total cellular protein as determined by densitometry.

9. b Expression of SlpI-4 in *B. subtilis:*

Plasmid pG10/SlpI was digested with EcoRI REN. After filling in the cohesive ends using the Klenow DNA polymerase reaction, the DNA was digested with BglII REN. Plasmid pSY662 was digested with SmaI and BamHI RENs. The two plasmids were then purified by electrophoresis through a low melting temperature agarose gel and purified with NACS (BRL) columns. The DNA fragment of pG10/SlpI was ligated to the backbone of pSY662 and transformed into *E. coli* containing ampicillin (40 μg/ml). Transformants were analyzed for plasmid contents and one (pSY662/G10/SlpI-4) was selected for further study.

Competent cells of *B. subtilis* B1Pol were transformed with pSY662/G10/SlpI-4 and incubated at 37° C. with shaking for 90 min. The transformation mixture was then diluted 1:100 in fresh LB containing 10 μg/ml of tetracycline and incubated at 37° C. with shaking. Samples were taken and equal numbers of cells were lysed and loaded on gels for separation by SDS-PAGE. Immunoblot analysis was performed using anti-SIp antibodies to detect the synthesis of the gene 10/SlpI-4 fusion protein.

The expression of the SlpI-4 polypeptide in *B. subtilis* was detected by its seroreactivity with anti-Slp antibody, after transfer of the cellular proteins from the polyacrylamide gel to a nitrocellulose filter. We verified that the seroreactive protein was the product of the SlpI-4 gene by exhaustively treating the cellular proteins with CNBr. This should cleave after methionine residues, but since SlpI-4 lacks methionine it will remain intact. The CNBr treatment eliminated greater than 98% of the proteins stainable with Coomassie blue dye. And as expected for a protein lacking methionine, SlpI-4 remained intact and still reacted with anti-SIp serum.

EXAMPLE 3

Assembly and Expression of the SIpIII Gene

1. Summary of the scheme for assembling the SlpIII gene:

The synthetic SlpIII gene codes for a protein similar to the SlpI gene and to the crystalline region of the silk fibroin protein made by the silkworm, *Bombyx mori*. SlpIII more closely resembles the silk fibroin molecule because it includes the amino acid tyrosine at regular intervals (about 50 residues), whereas multimers of SlpI do not. The SlpIII gene was assembled from smaller parts. First, three doublestranded sections of DNA of about 60 bp in length were chemically synthesized. Each section was cloned by insertion into bacteriophage H13 and the DNA sequence was verified. These sections were then removed from the vector and linked together in a specific order. This linkage of about 180 bp is named the SlpIII "monomer". "Monomers" were then linked in a specific order to yield dimers, trimers, tetramers, etc., of SlpIII. The multimers were then cloned either directly into plasmid expression vectors to detect the SlpIII protein or initially into an adapter plasmid. Insertion of the SlpIII DNA into the adapter allows for further gene manipulation and is further described later. The assembly scheme is pictured as follows:

2. Synthesis of double-stranded DNA sections The assembly Scheme is pictured as follows:

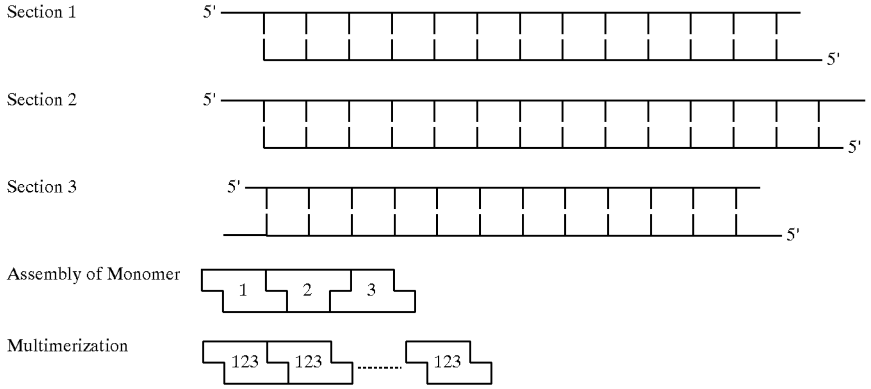

The DNA and corresponding amino acid sequences of the three sections of the SlpIII gene are shown in Table 3.

TABLE 3

```
B       N                                                               B
a       a                                                               a
n       e                                                               m
1       1                                                               H
|       |                                                               1
                                                                        |
GGT GCC GGC AGC GGT GCA GGA GCC GGT TCT GGA GCT GGC GCG GGC TCT GGC GCG GGC GCA G              61bs
CCA CGG CCG TCG CCA CGT CCT CGG CCA AGA CCT CGA CCG CGC CCG AGA CCG CGC CCG CGT CCT AG         65bs
 G   A   G   S   G   A   G   A   G   S   G   A   G   A   G   S   G   A   G   A   G   S
(SEQ ID NOS: 55–57)

B
a                                                                                      P
m                                                                                      s
H                                                                                      t
1                                                                                      1
|                                                                                      |
 GA TCC GGC GCA GGC GCT GGT TCT GGC GCA GGG GCA GGC TCT GGC GCA GGA GCG GGG TCT GGA GCT GCA   68bs
        G CCG CGT CCG CGA CCA AGA CCG CGT CCC CGT CCG AGA CCG CGT CCT CGC CCC AGA CCT CG     60bs
  G   S   G   A   G   A   G   S   G   A   G   A   G   S   G   A   G   A   G   S   G   A   A
(SEQ ID NOS: 58–60)
```

TABLE 3-continued

| | | |
|---|---|---|
| | P s t 1 (Pst1) … B a n 1 (Ban1) … H i n 3 (Hin3) | |
| | GGC TAT GGA GCT GGC GCT GGC TCA GGT GCT GGA GCA GGA AGC GGA GCG GGT GCC A | 55bs |
| | A CGT CCG ATA CCT CGA CCG CGA CCG AGT CCA CGA CCT CGT CCT TCG CCT CGC CCA CGG TTC GA | 63bs |
| | A G Y G A G A G S G A G A G S G A G A | |
| (SEQ ID NOS: 61–63) | | |

The double-stranded DNA sequence is shown in the 5' to 3' direction. The amino acids (g=glycine, a=alanine, s=serine, y=tyrosine) coded by the sequence are shown immediately below each section. Recognition sequences for cleavage by restriction endonucleases are shown above each section.

The above six single-strands were synthesized. After synthesis, the strands of DNA were purified and the homologous strands were annealed. About 1 μl (0.5 fg) of each strand was mixed with 2 μl of 10× AA (see Example 1) buffer and 16 μl of sterilized deionized $H_2O$ in a 1.5 ml polypropylene Eppendorf tube. The tube was placed in a boiling water bath (500 ml in a 1 liter beaker) for 10 min and then the beaker was removed from the hot plate and allowed to cool on the bench to room temperature. This required about 1–2 hr.

Each of the three double-stranded sections was cloned separately into M13nmp18. Section 1 was ligated between the SmaI and BamHI restriction sites of the multiple-cloning site. Section 2 was ligated between the BamHI and PstI sites. And section 3 was inserted between the PstI and HindIll sites. The respective clones are: M13mp18.1, M13mp18.2, M13mp18.3. The DNA sequence was determined for each cloned section. One representative of each section that had the correct DNA sequence was recovered and became the material for the next step: assembly of the "monomer".

3. Assembly of the "monomer" of SlpIII:

The DNA sections 2 and 3 were isolated by digestion of the M13 clones with restriction enzymes: for section 2, M13mp18.2 was digested with BamHI and PstI ; for section 3, M13mp18.3 was digested with PstI and HindIII. The two sections were purified and mixed together in equal molar amounts with M13 mp 18.1 that had been first digested with BamHI and HindIII. T4 DNA ligase was added to link the homologous overlapping ends in the order 1-2-3. Due to the hybridization specificity of the cohesive ends, the three sections are efficiently linked in only this order. The DNA sequence of the cloned "monomer" in the assembly named M13mp18.1.2.3 was determined to be correct and as shown in 2 above.

4. Multimerization of the "monomer" of Slp III:

In order to prepare large amounts of the "monomer" structural gene we first subcloned the "monomer" into the plasmid vector pUC12. M13mp18.1.2.3 was digested with EcoRI and HindIII restriction enzymes. The SlpIII "monomer" was gel purified and ligated into pUC12 digested with EcoRI and HindIII. The resulting plasmid DNA was prepared, the "monomer" was released from the vector by digestion with BanI REN and the fragment was gel purified.

To create multimers, "monomer" DNA with BanI ends were linked by ligation. The nonpalindromic terminal BanI recognition sequence allows linkage only in a head-to-tail order. The extent of multimerization is monitored by gel electrophoresis and staining the DNA with ethidium bromide. Multimers of more than 20 units have been obtained by this method.

5. Cloning of the multimers of SlpIII:

Plasmid pCQV2 (Queen, et al., *J. Appl. Mol. Gen.,* 2:1–10 (1983)) was digested with EcoRI and BamHI restriction endonucleases and a fragment of about 900 bp was purified. This DNA fragment contains the bacteriophage lambda cI-857 repressor gene, the closely linked rightward promoter, $P_R$, and the beginning of the cro gene. Plasmid pSY335 (described as pJF751 in Ferrari, et al., *J. Bacteriology,* 161: 556–562 (1985)) was digested with EcoRi and BamHi restriction enzymes and subsequently ligated to the DNA fragment of approximately 900 bp of pCQV2. The plasmid obtained from this construction, pSY751, expresses the β-galactosidase gene at 37° C. and 42° C., but not at 30° C. (FIG. 8).

In this approach the SlpIII gene is first cloned into an "adapter" sequence in an intermediate plasmid and then subcloned to the expression systems. The adapter sequence has the following useful features: a unique central BanI REN site, three unique REN sites to either side of BanI, information coding for protein cleavage at either methionine, aspartate-proline or arginine amino acids and small size. The BanI site is the point of insertion for the SlpIII multimers with BanI ends.

The adapter was synthesized with the Applied Biosystems 380A Synthesizer, cloned in M13mp18 and the DNA sequence verified. The adapter was then subcloned into a specially-constructed plasmid vector that lacked BanI REN sites. The recipient plasmid was made as follows. Plasmid pJH101 (Ferrari, et al, 1983) was partially digested with AhaIII restriction enzyme and religated. Transformants of *E coli* HB 101 were selected on medium containing chloramphenicol (12.5 mg/ml). After restriction analysis of several isolates one plasmid was chosen, pSY325 (FIG. 7). This plasmid contains only the chloramphenicol-resistance gene and the replication origin (from pBR322) of pJH 101. After digestion to completion with XhoII, pSY325 was ligated with the gel-purified adapter. The result was the adapter-plasmid, pSY937. The new pSY937 REN sites were verified.

The SlpIII multimers were cloned into the BanI site of pSY937 (FIG. 7). Positive clones were identified by colony hybridization and with the lower strand of section 1 of SlpIII as the DNA probe for hybridization (probe sequence shown in Table 2). Positive clones were characterized by gel electrophoresis for the size of the inserted multimer. Finally, the SlpIII sequences were subcloned using the REN site in the flanking adapter regions to specific locations of expression plasmids.

The SlpIII protein had the following amino acid composition:

SlpIII 1178 AA MW 83,000

(fm) DPVVLQRRDWENPGVTQLNRLAAHPPFASDPM
GAGS $(GAGAGS)_6$ GAAGY
$[(GAGAGS)_9$ $GAAGY]_{18}$
GAGAGSGAGAGSGAGAMDPGRYQLSAGRYHYQLVWCQK
(SEQ ID NO: 64)
(fm) intends the initiation codon

SlpIII Expression Vector

Plasmid DNA pSY1086 is a pSY937 derivative containing 19 repeats of the SlpIII DNA monomer (3.5 kb). This plasmid DNA was digested with NruI and PvuII and the fragments separated by agarose gel electrophoresis. The purified SlpIII multimer was then cloned in plasmid pSY751 digested with PvuII REN. Several clones were analyzed and one (pSY1008) was chosen to be used in expression experiments and SlpIII purification.

The ampicillin drug resistance gene of pSY1008 was substituted with the kanamycin marker from pSY1010 (produced by digestion of pSY633 with DraI and SspI and insertion of $Kan^R$ obtained by HincII digestion of pUC4K) and the subsequent plasmid was called pSY1186. By removing the SlpIII portion of plasmid pSY1186 with BanI, a new plasmid, pSY1262, was generated. This plasmid contains a unique BanI site which allows for the direct ligation of fragments containing BanI ends obtained by polymerization of monomers. This plasmid has been used to generate plasmids containing inserts for the following proteins: SELP1, 2, 3, and Slp4.

Production and Purification of SlpIII Cell Culture

*E. coli* are cultured in the following medium:

| Medium C | g/l |
|---|---|
| yeast extract | 20 |
| casamino acids | 20 |
| peptone | 20 |
| gelatin peptone | 20 |
| $KH_2PO_4$ | 2 |
| $K_2HPO_4$ | 2 |
| $Na_2HPO_4 7H_2O$ | 2 |
| glucose | 2 |
| ampicillin | 0.1 |

An overnight culture (500 ml–11) which had been grown at 30° C. was used to inoculate 375 l of media contained in a 500 l fermentor. Fermentor conditions include a tachometer reading of 100 rpm, vessel back pressure of 5 psi and an air flow of 170 1/min in order to maintain dissolved $0_2$ at greater than 50%.

Glucose (1g/l) and ampicillin (0.05 g/l) were added to the fermentation when the culture reached an $OD_{650}$ of 1.0 and again at 2.0. When the culture reached an $OD_{650}$of 2.0 the temperature was increased to 42° C. for 10 min and then lowered to 38° C. for 2 hours. The culture was then chilled to 10° C. and cells were harvested by centrifuigation in a continuous centrifuge and frozen at −70° C. until processed. Yields from two separate fermentations were 7.3 kg and 5.2 kg wet weight of cells.

It should be noted that other media can be used and, with different plasmids, various selection conditions can be imposed (i.e., substitution of kanamycin selection for ampicillin). These conditions have been used in laboratory scale fermentations (10 l volumes).

Cell Lysis

Method 1.

Cells were thawed and suspended to a concentration of 1 kg wet weight in 6l of 50 mM Tris-HCl pH 7.0, 1 mM EDTA and broken by 2 passages through an APR Gaulin cell disrupter at 8000 psi. During this lysis procedure the cells were kept cold with an ice bath. The cell lysate was then centrifuged at 26,000×g with a continuous centrifuge, such as the T2-28 rotor in a Sorvall RC5B refrigerated centrifuge operated at 4° C. Under these conditions greater than 90% of the SlpIII produced could be found in the pellet. The supernatant did contain some product which could be recovered by $NH_4SO_4$ precipitation as described below. The pellet was extracted with LiBr as described below.

Method 2.

Frozen cells were thawed and resuspended to a concentration of 1 kg wet weight in 6 L of 50 mM Tris-HCl pH 7.0, 10 mM EDTA, and 5 mM PMSF to inhibit protease activity. Cells were stirred in this buffer at room temperature for 0.5 to 2 hours, then lysozyme was added to a concentration of 1 g/l and incubation was continued for 20 min. β-Mercaptoethanol was then added to 70 mM and the detergent NP40 was then added to a final concentration of 1% for 20 min while continuously stirring the cell suspension. Then $MgCl_2$ was added to 50 mM followed by DNAse at a concentration of 1 mg/l and incubation was continued at room temperature for 20 min. The cell lysate was then centrifuged as in method 1 at 26,000×g in a continuous centrifuge and the supernatant was collected and passed through the continuous centrifuge a second time at 26,000× g. The supernatant resulting from this second centrifugation contains <5% of the total SlpIII, but what was there can be recovered with $NH_4SO4$ as described below. The pellets resulting from the 1st and 2nd 26,000×g centrifugations were combined and extracted with LiBr as described below.

Method 3.

For this method, a strain of *E.coli* is used that contains a second plasmid which encodes the T7 phage lysozyme. This plasmid is compatible with the plasmid encoding the SlpIII gene and the drug resistance determinant. The strain was grown in the same medium and under the same conditions as in the first two methods. However, due to the production of the T7 lysozyme inside the cells, their cell wall was weakened and they could be easily lysed at the completion of the fermentation by the addition of EDTA to >100 mM and NP4O to a concentration of from 0.5 to 1.0% v/v. Lysis could also be achieved by the addition of chloroform (20 ml per liter) to the fermentation broth instead of NP4O. Alternatively, cells could be collected by centrifugation prior to lysis, resuspended to 1 kg wet weight in 6 L of Tris-EDTA as described in the first two methods and then lysed by the addition of NP4O or chloroform. Following cell lysis by either method the lysate was centrifuged in a continuous rotor at 26,000×g as described in the first two methods. As with those methods, LiBr extraction of the pellet and $NH_4SO_4$ precipitation of the supernatant were used to recover the product.

Purification of SlpIII

The pellet obtained by centrifugation of the cell lysate at 26,000×g as described above was extracted with an equal volume of 9M LiBr. The salt solution was added and the pellet was evenly suspended by stirring at room temperature (RT). The mixture was stirred for 1 hour at RT. After an even suspension was obtained, the mixture was then centrifuged at 26,000×g in a continuous rotor at 4° C. or at RT to generate a pellet and a supernatant fraction. The supernatant was saved and the pellet was re-extracted with another equal volume of 9M LiBr as above. After mixing for 1 hour the mixture was centrifuged at 26,000×g and the supernatant from this centrifugation was combined with the supernatant from the first LiBr extraction and allowed to stand at 4° C. overnight. Approximately 90% of the SlpIII contained in the cell lysate 26,000×g pellet was extracted by LiBr using this procedure.

After the LiBr extract stood overnight at 4° C. a precipitate formed, was removed by centrifugation at 26,000×g and was discarded. The supernatant was then placed in dialysis bags and dialyzed against several changes of $dH_2O$ for 2 days. As the LiBr was removed by dialysis the SlpIII product precipitated in the dialysis bags. The precipitate was collected by centrifugation and washed 2–3 times with $dH_2O$. The final washed product was centrifuged and dried by lyophilization.

For the recovery of SlpIII from the 26,000×g supernatant fractions, $NH_4SO_4$ precipitation was used. Solid $NH_4SO_4$ was slowly added to the sample which was maintained at 4° C., until 38% saturation was achieved (231 g/l). The mixture was then stirred at 4° C. for 2–3 hours. The precipitate was recovered by centrifugation in a continuous flow centrifuge and washed 4–5 times with an equal volume of distilled $H_2O$ or with 0.5% SDS in $H_2O$. After each wash the precipitate was recovered by continuous centrifugation. The pellet became increasingly white with successive washes as contaminating protein was removed. SlpIII was recovered as a washed pellet and was dried by lyophilization.

Trypsin Treatment Step of SlpIII

SlpIII was suspended in 50 mM Tris-HCl, pH 8.0, 0.1 M NaCl buffer, and was placed in a 37° C. water bath, and TPCK treated trypsin solution was mixed into the suspension. The final trypsin concentration was 0.1%. After 3 hours, the solution was centrifuged at 16,000×g for 15 min, the pellet was washed with a half equal volume of 0. 5% SDS in $H_2O$ first, then with distilled water. After each wash the pellet was recovered by centrifugation. The final product was resuspended in water and kept at 4° C. for further analysis.

With the trypsin treatment, SlpIII was purified to 99.4% purity.

Physical Measurements of SlpIII

Physical measurements of the purified silk-like proteins have been compared with those of *Bombyx mori* silk in order to establish that the repetitive amino acid polymers produced microbiologically accurately mimic the properties of naturally occurring polymers. Physical measurements were performed to confirm the model of anti-parallel chain pleated sheet conformation for the crystalline regions of *Bombyx mori* silk fibroin (Marsh, Corey and Pauling, *Biochem. Biophys. Acta* (1955) 16; Pauling and Corey, *Proc. Natl. Acad. Sci. USA* (1953) 39:247). Preliminary analysis of x-ray diffraction patterns obtained from Sip films are consistent with those described by Fraser, MacRai, and Steward (1966) (Table 4). Circular Dichroic (CD) and Fourier transform infrared (FTIR) spectroscopic analysis of SlpIII were consistent with a high degree of extended β and β-turn conformations. Comparisons of the spectra obtained from SlpIII with that of naturally occurring silk fibroin in various solvents (Isuka and Young, *Proc. Natl. Acad. Sci. USA* (1966) 55:1175) indicated that SlpIII in solution consists of a mixture of the random and highly ordered structures seen in silk fibroins.

TABLE 4

| Material | a (A) | b (A) | c (A) |
|---|---|---|---|
| $(AG)_n$ | 9.42 | 6.95 | 8.87 |
| $(AGAGSG)_n$ | 9.39 | 6.85 | 9.05 |
| CTP fraction | 9.38 | 6.87 | 9.13 |
| Native fibroin | 9.40 | 6.97 | 9.20 |
| | 9.44 | 6.95 | 9.30 |
| SlpIII | 9.38 | 6.94 | 8.97 |

Referenced in Fraser et al., J. Mol. Biol. (1966) 19:580.

EXAMPLE 4

EBSI Gene Construction

Six oligonucleotide strands were synthesized and purified as described previously.

```
    (HIII)  BanII                StuI
i.   5'AGCTGGGCTCTGGAGTAGGCCTG3' (SEQ ID NO: 65)

ii.  5'AATTCAGGCCTACTCCAGAGCCC3' (SEQ ID NO: 66)
    (ER1)  StuI                BanII

    (HIII) BanI
iii. 5'AGCTTGGTGCCAGGTGTAGGAGTTCCGGGTGTAGGCGTTCCGGGAGTTGG
     TGTACCTGGAGTGGGTGTTCCAGGCGTAGGTGTGC3' (SEQ ID NO: 67)

    (XmaI)
iv.  5'CCGGGCACACCTACGCCTGGAACACCCACTCCAGGTACACCAACTCCCGGA
     ACGCCTACACCCGGAACTCCTACACCTGGCACCA3' (SEQ ID NO: 68)
                                BanI

    (XmaI)                        AhaII
v.   5'CCGGGGTAGGAGTACCAGGGGTAGGCGTCCCTGGAGCGGGTGCTGGTAG
     CGGCGCAGGCGCGGGCTCCGGAGTAGGGGTGCCG5' (SEQ ID NO: 69)
               BanII          BanI

    (ERI) BanI                  BanII
vi.  5'AATTCGGCACCCCTACTCCGGAGCCCGCGCCTGCGCCGCTACCAGCACCCG
     CTCCAGGGACGCCTACCCCTGGTACTCCTACC3' (SEQ ID NO: 70 )
         AhaII
```

Oligonucleotide strands (iii), (iv), (v) and (vi) were annealed and ligated with the DNA of plasmid pBSm13(+)

(Stratagene) which had been digested with HindIII and EcoRI. The products of this ligation reaction were transformed into *E. coli strain* JM109. Transformant colonies were selected for resistance to ampicillin. Colonies were screened for their hybridization with $^{32}P$-labelled oligonucleotides (iii), (v). Plasmid DNA from several positively hybridizing clones was purified and sequenced. Two of the plasmids, pSY1292 and pSY1293, contained the sequence shown for oligonucleotides (iii), (v) and (iv), (vi). These sequences contained all of the nucleotides present in these synthetic oligonucleotides except one. A G:C basepair was missing at position 7 (iii). The lack of this basepair obstructed one of the BanI sites. In order to introduce a second BanII site at the 5' end of the gene fragment, oligonucleotides (i) and (ii) were annealed and ligated with plasmid pBSm13(+) which had been digested with HindIII and EcoRI. Plasmid DNA from the transformant colonies resistant to ampicillin was purified. Two plasmids, pSY1295 and pSY1296, which were digestible with StuI, a unique site contained in the oligonucleotide sequence, were sequenced. They were both shown to contain the sequence shown for oligonucleotides (i) and (ii). Plasmid DNA From pSY1292 was digested sequentially with HindIII, SI nuclease, and EcoRI. The digestion products were separated by electrophoresis in an agarose gel and the DNA fragment of approximately 150 basepairs was excised from the gel. This DNA fragment was ligated with plasmid DNA pSY1296 which had been digested with Stul and EcoRI. The products of this ligation reaction were transformed into *E. coli strain* JM109 and were selected for resistance to ampicillin. Colonies were screened for hybridization to $^{32}P$-labelled oligonucleotide (v). The plasmid DNA from two positively hybridizing clones was purified and sequenced. These plasmids were named pSY1297 and pSY1298. They contained the following sequence:

```
(HindIII)    BanII
   AGCTGGGCTCTGGAGTAGGTGTGCCAGGTGTAGGAGTTCCGGGTGTAGGCGTTCCGGGAG  60
   TCGACCCGAGACCTCATCCACACGGTCCACATCCTCAAGGCCCACATCCGCAAGGCCCTC
                                                    XmaI
   TTGGTGTACCTGGAGTGGGTGTTCCAGGCGTAGGTGTGCCCGGGGTAGGAGTACCAGGGG  120
   AACCACATGGACCTCACCCACAAGGTCCGCATCCACACGGGCCCCATCCTCATGGTCCCC
                                                    BanII
   TAGGCGTCCCTGGAGCGGGTGCTGGTAGCGGCGCAGGCGCGGGCTCCGGAGTAGGGGTGC  180
   ATCCGCAGGGACCTCGCCCACGACCATCGCCGCGTCCGCGCCCGAGGCCTCATCCCCACG
     EcoRI
   CGAATTC                                  (SEQ ID NO: 71)
   GCTTAAG
```

EBSI Multimer Gene Assembly:

The BanI acceptor plasmid pSY937 was modified in order to accept BanII terminal cohesive DNA fragments. Two oligonucleotides were synthesized for this purpose.

```
         (BamHI)      DraI    SspI   NruI                      BanII
vii.    5'GATCCTATGTTTAAATATTCTCGCGAACGTTTTTGTATGGGCTCGATGTGT
          TACCGTGCGCATGGATATCAGCTG3'
                   FspI       EcoRV    PvuII                  (SEQ ID NO: 72)

        (BamHI)PvuII EcoRV                     FspI
                  BanII
viii.      5'GATCCAGCTGATATCCATGCGCACGGTAACACATCGAGCCCATACAAAAA
        CGTTCGCGAGAATATTTAAACATAG3'
           NruI     SspI     DraI                             (SEQ ID NO: 73)
```

Oligonucleotides (vii) and (viii) were annealed and ligated with plasmid DNA pSY937 which was digested with BamHI. The products of this ligation were transformed into *E coli* strain JM109 and colonies were selected for resistance to chloramphenicol. Transformant colonies were screened by hybridization to $^{32}P$-labelled oligonucleotide (vii). Plasmid DNA from two positively hybridizing clones, pSY1299 and pSY1300, contained the sequence shown for oligonucleotides (vii) and (viii), as determined by DNA sequencing.

Plasmid DNA pSY1298 was digested with BanII and the digestion fragments separated by agarose gel electrophoresis. The EBSI gene fragment, approximately 150 base pairs, was excised and purified by electro-elution and ethanol precipitation. Approximately 1 $\mu$g of purified fragment was self-ligated in order to produce multimers ranging in size from 450 bp to 6,000 bp. The products of the self-ligation were then ligated with plasmid DNA pSY1299 which had been digested with BanII. The products of this ligation reaction were transformed into *E. coli* strain HB 101. Transformants were selected for resistance to chloramphenicol. Plasmid DNA from individual transformants was purified and analyzed for increased size due to EBSI multimer DNA insertions. Ten clones (pSY1240–1249) with inserts ranging in size from 1.5 Kbp to 4.4 Kbp were obtained.

Expression of EBSI Multimer Gene:

One of these clones, pSY1248, which contained a 4 Kb EBSI multimer gene was recloned in the $\lambda P_R$ expression vector, pSY751. Plasmid DNA from pSY1248 was digested with NruI and PvuII, separated by agarose gel electrophoresis, and the DNA band corresponding to the EBSI multimer gene was excised and purified by NACS purification. DNA from plasmid pSY751 was digested with PvuII and ligated with the NruI-PvuII fragment from pSY1248. The products of this ligation were transformed into *E. coli* HB 101, and the transformants selected for resistance to ampicillin. Two clones were isolated containing the new plasmid pSY1280. *E. coli cells containing pSY*1280 were grown at 30° C. to an $OD_{6000}$ of 0.7 and then shifted to 42° C. for 1.5 hours. The proteins produced by these cells was analyzed by SDS-PAGE. The separated proteins were transferred to nitrocellulose paper and detected by immunoreactivity with anti-ELP rabbit serum. A strongly reactive protein band was observed with an apparent molecular weight of 120 kDal.

The Ampicillin drug resistance gene of pSY1280 was substituted with the Kanamycin marker and the subsequent plasmid was called pSY1332. This plasmid was used in fermentation for the purification of EBSI. (See Methods)

pSY1332/pSY1280    EBSI Protein    1464 AA    MW 113,159

MDPVVLQRRDWENPGVTQLNRLAAHPPFASERFCMGS
    [(GVGVP)$_8$(GAGAGSGAGAGS)$_1$]$_{27}$
    MCYRAHGYQLSAGRYHYQLVWCQK (SEQ ID NO: 74)

Purification oF EBSI Protein:

E. coli strain HB101 containing plasmid pSY1280 was fermented in 10 L volume. The cells were concentrated by filtration and further harvested by centrifugation. Pelleted cells were stored frozen at −70° C. until processed. Frozen cells were thawed on ice and suspended in 4 ml of 50 mM Tris-HCl pH 7.0, 10 mM EDTA, 5 mM PMSF per gram wet weight of cells. The cells were broken by French pressing twice at 15,000 psi and then cooled to 0° C. The crude lysate was cleared by centrifugation at 26,000×g for 20 minutes. The supernatant proteins were precipitated by addition of solid ammonium sulfate to 20% of saturation (114 g/l). The precipitate was collected by centrifugation at 10,000×g for 10 min. The pellet was resuspended in 10 ml of H$_2$O and dialyzed against 10 mM Tris pH 8.0, 0.15M NaCl at 4° C. The dialyzed solution was digested with 0.1% Trypsin (Sigma) for 1.5 hours at room temperature, and reprecipitated with 20% ammonium sulfate. The precipitated protein was resuspended in H$_2$O and dialyzed against 10 mM Tris pH 7.0, 1 mM EDTA at 40° C. The protein purity of this sample was analyzed by amino acid composition and determined to be 83%.

Elastic Properties of EBSI Protein:

The soluble preparation of semi-purified EBSI protein described above was incubated at 37° C. for 30 min and centrifuged at 10,000×g for 10 min at room temperature. This treatment caused the EBSI protein to aggregate, become insoluble, and pellet into a translucent solid. The solid was resistant to mechanical disruption 15 either by vortexing or by maceration using a glass rod. The solid could be cut with a razor blade into strips which exhibited a high degree of elasticity. These strips fully retained their shape after repeated extensions and relaxations. They resisted compression with no apparent irreversible deformation of structure.

EBSI Purification

EBSI sample (~70% pure) was dialyzed in 50 mM Tris HCl, 50 mM NaCl, pH 8.0° at 4° C. overnight with one change of buffer. If precipitation was observed, the sample was centrifuged at 27,000×g for 15 min at 4° C. All remaining steps were performed at 4° C. The supernatant was applied to a DEAE-Sephacel column which had been equilibrated with 50 mM Tris HCl, 50 mM NaCl, pH 8.0.

The flow through fractions which contained EBSI were collected and pooled. NaCl was added to the pooled fractions from DEAE-Sephacel column to make a final concentration of 2M NaCl in the sample. Insoluble material was removed by centrifugation at 27,000×g for 20 min. The supernatant was then loaded onto Phenyl-Sepharose column which was equilibrated with 50 mM sodium phosphate buffer, pH 7.0, with 2M NaCl. The column was washed extensively with buffer until no eluting protein was detected by A$_{280}$. The column was then eluted stepwise with 50 mM sodium phosphate buffer, pH 7.0 and finally with water. The EBSI active fractions were pooled and stored at 4° C. for further analysis.

With the addition of these steps to the previous procedures, 100% pure EBSI was obtained.

EXAMPLE 5

ELPI Construction and Expression

Two oligonucleotide strands were synthesized and purified as described in the Methods section.

```
         (EcoRI)     BanI                                     SmaI
i) 5'AATTCGGTGCCCGGTGTAGGAGTTCCGGGTGTAGGCGTTCCCGGGGTAG
       GCGTTCCGGGAGTAGGGGTGCCA3'
                              BanI                      (SEQ ID NO: 75)

                 BanI                                    SmaI
ii) 3'GCCACGGGCCACATCCTCAAGGCCCACATCCGCCAAGGGCCCCATCCGCA
      AGGCCCTCATCCCCACGGTTCGA5'
                    BanI(HindIII)                       (SEQ ID NO: 76)
```

The two oligonucleotide strands were annealed and ligated with the DNA of plasmid pBS m13(+) (Stratagene) which had been digested with RENs HindIII and EcoRI.

The products of this ligation reaction were transformed into E. coli strain JM109.

Transformant colonies were screened for their hybridization with $^{32}$P-labeled oligonucleotide (i). Plasmid DNA from positively hybridizing clones was purified and sequenced. One plasmid, pSY1287, contained the sequence shown for oligonucleotides (i) and (ii).

Plasmid DNA from pSY1287 was digested with BanI REN and the digestion fragments were separated by agarose gel electrophoresis. The ELPI gene fragment, approximately 60 bp, was excised and purified by NACS column. Approximately 1 μg of purified fragment was self-ligated in order to produce multimers ranging in size from 300 bp to 5000 bp.

The products of the self-ligation were then ligated with plasmid DNA pSY937 which had been digested with REN BanI. The product of this ligation reaction was transformed into E. coli strain HB 101. Transformants were selected for resistance to chloramphenicol. Plasmid DNA from individual transformants was purified and analyzed for increased size due to ELPI multiple DNA insertions. Four clones (pSY1388–1391) with inserts ranging in size from 1.0 kbp to 2.5 kbp were obtained. These clones were recloned in the λPr expression vector pSY751. The clones obtained (pSY1392–1395) were used for expression of ELPI.

The ELPI protein had the following amino acid composition:

pSY1395 ELPI Protein 859 AA MW 72,555

MDPVVLQRRDWENPGVTQLNRLAAHPPFARNILAIRW
$[(VPGVG)_4]_{40}$ VPWTRVDLSAGRYHYQLVWCQK
(SEQ ID NO: 77)

SELP1 Gene Construction and Expression

Two oligonucleotide strands were synthesized and purified as described in the Methods section.

```
       FspI    PvuII     SnaBI    (PstI)
(i)  5'-GTGCGCAGCTGGTACGTAGCTGCA-3'  (SEQ ID NO: 78)

       (PstI)         PvuII
(ii) 3'-ACGTCACGCGTCGACCATGCATCG-5'  (SEQ ID NO:79)
              FspI       SnaBI
```

These oligonucleotide strands were annealed and ligated with plasmid pSY1304 which had been digested with PstI REN (pSY1304 differs from pSY857 by having a monomeric unit in place of the trimeric unit of pSY857). Plasmid DNA from transformant colonies resistant to chloramphenicol was purified. One plasmid, pSY1365, which was digestible with REN SnaBI, was sequenced and proven to be correct.

ELPI gene fragment purified as described (ELPI construction and expression) was treated with Mung Bean Nuclease as described by supplier (Stratagene). The DNA fragments mixture was then ligated with plasmid DNA pSY1364 which had been digested sequentially with RENs FspI, SnaBI and calf intestinal phosphatase. The products of this ligation reaction were transformed into *E. coli* strain HB101 and were selected for resistance to chloramphenicol. Plasmid DNA from individual transformants was purified and analyzed for the ELPI monomer DNA insertion. Two plasmids, pSY1365 A and B, were sequenced. They were both shown to contain the ELPI DNA sequence in the correct orientation.

Plasmid DNA pSY1365 was digested with REN Bani and the DNA fragment containing the SELP1 monomer was gel purified. To create multimers, 1 μg of the SELP1 DNA fragment was self-ligated. Multimers were obtained ranging in size from 500 bp to 10 kbp. The SELP1 multimers were cloned into the BanI site of pSY1262. Positive clones were characterized by gel electrophoresis for the size of the inserted multimer and used for expression and protein analysis.

pSY1396 SELP1 Protein 2100 AA MW 148,212

MDPVVLQRRDWENPGVTQLNRLAAHPPFASDPMGAGS $(GAGAGS)_6$
$[GAA(VPGVG)_4$ VAAGY $(GAGAGS)_9]_{23}$
$GAA(VPGVG)_4$ VAAGY $(GAGAGS)_2$ GAGAMDPGRYHYQLVWCQK
(SEQ ID NO: 80)

SELP2—Monomer Construction

Plasmid DNA pSY1298 was digested with BanII REN and the EBSI gene fragment was purified as described previously. The EBSI monomer fragment was ligated into pSY1304 (pSY937 containing a monomer of SlpIII, constructed as pSY857) which had been digested with BanII REN and treated with calf intestinal phosphatase.

The products of the ligation mixture were transformed in *E. coli* strain HB 101. Transformants were selected for resistance to chloramphenicol. After restriction analysis of several isolates, one plasmid was chosen, pSY1301, containing a DNA fragment corresponding to the SELP2monomer gene.

SELP2—Multiple Gene Assembly and Expression

Plasmid DNA pSY1301 was digested with REN BanI and the DNA fragment containing the SELP2 "monomer" was gel purified. To create multimers, 1 μg of the SELP2 DNA fragment was self-ligated. Multimers were obtained greater than 12 kb in size.

The SELP2 multimers were cloned into the BanI site of pSY1262. Positive clones were characterized by gel electrophoresis for the size of the inserted multimer. The clones with inserts ranging in size from 1.5 kb to 11 kb were selected. Plasmid DNA pSY1372 containing an insert of 6 kb (18 repeats) was used for further analysis and protein purification.

SELP2—Protein Purification

*E. coli* strain HB101 containing plasmid pSY1372 was fermented according to the procedure described in Methods for fermentation. The cells were harvested by centrifugation. Pelleted cells were stored frozen at −70° C. until processed. Frozen cells were thawed on ice and suspended in 4 ml of 50 mM Tris-HCl, pH 7.0, 10 mM EDTA, 5 mM PMSF per gram wet weight of cells. The cells were broken by passing through a Gaulin cell disrupter at 8,000 psi. The crude lysate was cleared by centrifugation at 26,000×g for 20 min. The supernatant, which contained >75% of the SELP2 protein, was precipitated by addition of 20% ammonium sulfate (114 g/L). The precipitate was collected by centrifugation at 10,000×g for 10 min. The pellet was resuspended in 10 ml of $H_2O$ and dialyzed against 10 mM Tris pH 8.0, 0.15 M NaCl at 4° C. The dialyzed material was centrifuged at 26,000×g for 15 min in order to collect the insoluble fraction of protein which contained approximately 10% of the SELP2 protein. This insoluble protein pellet was washed twice in 0.2% SDS at 50° C. for 30 min with occasional shaking. The insoluble protein was collected each time by centrifugation at 26,000×g for 15 min followed by a wash of 50% ethanol. The final protein pellet was resuspended in water and analyzed by Western blot analysis and amino acid composition. By Western blot the SELP2 protein appears to be homogeneous in size consistent with its large molecular weight (>150 kDal). By amino acid composition the SELP2 preparation is approximately 80% pure and the observed molar ratio of amino acids (Ser:Gly:Ala:Pro:Val:Tyr) agrees very closely with the expected composition as predicted from the SELP2 sequence present in pSY1372.

pSY1372 SELP2 Protein 2055 AA MW 152,354

MDPVVLQRRDWENPGVTQLNRLAAHPPFASDPMGAGS
(GAGAGS)$_2$(GVGVP)$_8$
[(GAGAGS)$_6$GAAGY (GAGAGS)$_5$ (GVGVP)$_8$]$_{17}$
(GAGAGS)$_6$ GAAGY (GAGAGS)$_2$ GAGAMDPGRYQLSAGRYHYQLVWCQK
(SEQ ID NO: 81)

SELP3—Construction and Expression

Plasmid DNA pSY1301 was partially digested with REN HaeII and the digestion fragments separated by agarose gel electrophoresis. The larger DNA fragments were excised and purified by NACS column. The purified fragments were self-ligated, the ligation reaction was heated at 70° C. for 15 min to inactivate the T4 DNA ligase and eventually digested with REN PstI. The digestion mixture was then transformed into *E. coli* strain JM109. Transformants were selected for resistance to chloramphenicol. Plasmid DNA from individual transformants was purified and analyzed for: (1) resistance to REN PstI; and (2) deletion of 60 bp HaeII fragment contained within the SELP2 gene fragment. One clone (pSY1377) satisfied both requirements. Plasmid DNA from pSY1377 was digested with REN BanI and the DNA fragment containing the SELP3 monomer was gel purified. To create multimers, 1 μg of the SELP3 DNA fragment was self-ligated. Multimers were obtained ranging in size from 500 bp to 10 kbp. The SELP3 multimers were cloned into the BanI site of pSY1262. Positive clones were characterized by gel electrophoresis for the size of the inserted multimer and used for expression and protein analysis.

pSY1397 SELP3 Protein 2257 AA MW 168,535

MDPVVLQRRDWENPGVTQLNRLAAHPPFASDPMGAGS (GAGAGS)$_2$
[(GVGVP)$_8$ (GAGAGS)$_8$]$_{24}$
(GVGVP)$_8$ (GAGAGS)$_5$ GAGAMDPGRYQLSAGRYHYQLVWCQK
(SEQ ID NO: 82)

SLP4—Construction and Expression

Plasmid DNA from pSY1304 was partially digested with REN HaeII and the digestion fragments separated by agarose gel electrophoresis. The larger DNA fragments were excised and purified by NACS column. The purified fragments were self-ligated, the ligation reaction was heated at 70° C. for 15 min to inactivate the T4 DNA ligase and eventually digested with REN PstI. The digestion mixture was then transformed into *E. coli* strain JM109. Transformants were selected for resistance to chloramphenicol. Plasmid DNA from individual transformants was purified and analyzed for: (1) resistance to REN PstI; and (2) deletion of 60 bp HaeII fragment contained within the SELP2 gene fragment. One clone (pSY1378) satisfied both requirements.

Plasmid DNA pSY1378 was digested with REN BanI and the DNA fragment containing the SLP4 monomer was gel purified. To create multimers, 1 μg of SLP4 DNA was self-ligated. Multimers were obtained ranging in size from 300 bp to 6 kbp. The SLP4 multimers were cloned into the BanI site of pSY1262. Positive clones were characterized by gel electrophoresis for the size of the inserted multimer and used for expression and protein analysis.

pSY1398 SLP4 Protein 1101 AA MW 76,231
MDPVVLQRRDWENPGVTQLNRLAAHPPFASDPMGAGS [(GAGAGS)$_6$]$_{28}$
(GAGAGS)$_5$ GAGAMDPGRYQLSAGRYHYQLVWCQK
(SEQ ID NO:83)

FCB-SLPIII (SLPF) Construction and Expression:

The SLPIII polymer was chosen as a backbone structure for insertion of a biologically functional sequence because of its predicted structure, allowing for fabrication of useful products; having good structural properties for use in a wide variety of applications; having β-turn structures between interactive strands; and allowing for substitution of the turn sequences with other sequences. The fibronectin cell-binding domain, amino acids 1405–1512, has a strong turn propensity, with the tripeptide RGD providing for cell attachment, predicted to be present within a hydrophilic loop between adjacent B-strands. A 10 amino acid sequence spanning this proposed loop structure (referred to as fibronectin cell-binding or FCB sequence) was chosen to constitute the functional block of amino acids to be inserted within the SLPIII backbone. The insertion site within the SLPIII backbone was chosen to correspond with the amino-acid sequence GAAGY (SEQ ID NO:78) which is also predicted to provide a turn structure (Chou and Fassman, *Biochemistry*, 13:222–244 (1974)). The design allows for conservation of the FCB structure while causing minimal disruption of the SLPIII (GAGAGS)$_9$ β-strand crystal-packing domains.

The SLPIII gene monomer contains a PstI restriction endonuclease site within the sequence encoding the proposed turn structure, GAAGY. This site was used to insert the synthetic DNA encoding the 10 amino acids of the FCB sequence. Two complementary DNA strands comprising the FCB site, 36 bases in length, were synthesized consisting of the sequence shown below:

5' - GTGACTGGCCGTGGTGATAGCCCGGCTAGCGCTGCA - 3'
3' - ACGTCACTGACCGGCACCACTATCGGGCCGATCGCG 5'
(SEQ ID NO:84 & 85)

These oligonucleotides were purified according to the procedures described in Example 1, and cloned into the PstI site of pSY1304. PSY1304 DNA was digested with PstI and ligated with a mixture of the FCB oligonucleotides. The ligation reaction products were transformed into *E. coli cells*. Colonies containing the plasmid were selected on bacterial culture plates containing the antibiotic chloramphenicol. Individual colonies were grown and plasmid DNA purified and analyzed for the presence of the FCB oligonucleotide sequence by restriction digestion with NheI. Plasmids containing this restriction site were subjected to DNA sequencing and two candidates were shown to be correct. The partial nucleotide sequence of one of these, pSY1325, and the encoded amino-acid sequence were as follows:

```
Ban I
GGT GCC GGC AGC GGT GCA GGA GCC GGT TCT GGA GCT GGC
G   A   G   S   G   A   G   A   G   S   G   A   G

                                Bam HI
GCG GGC TCT GGC GCG GGC GCA GGA TCC GGC GCA GGC GCT
A   G   S   G   A   G   A   G   S   G   A   G   A

GGT TCT GGC GCA GGG GCA GGC TCT GGC GCA GGA GCG GGG
G   S   G   A   G   A   G   S   G   A   G   A   G

            Pst I
TCT GGA GCT GCA GTG ACT GGC CGT GGT GAT AGC CCG GCT
S   G   A   A   V   T   G   R   G   D   S   P   A

    Pst I
AGC GCT GCA GGC TAT GGA GCT GGC GCT GGC TCA GGT GCT
S   A   A   G   Y   G   A   G   A   G   S   G   A

                            Ban I
GGA GCA GGA AGC GGA GCG GGT GCC
G   A   G   S   G   A   G
```

(SEQ ID NO:86 & 87)

The FCB-SLP monomer gene fragment was purified from pSY1325 by digestion with BanII, agarose-gel electrophoresis, and NACS purification (Example 1). The monomer gene fragment was self-ligated and cloned into pSY937 which had been digested with BanI. The products of this ligation were transformed into *E. coli* and selected for growth on chloramphenicol. Plasmid DNA from individual colonies was analyzed for inserts containing multiple FCB-SLP monomer fragments by digestion with NruI and EcoRV and electrophoresis on agarose gels. One clone was identified containing two inserts, one of approximately 2.1 kb and the other of 2.8 kb. Both inserts were cloned individually and transferred to the expression vector pSY75 1. Plasmid pSY1325 was digested with NruI and PvuII and the 2.1 and 2.8 kb insert bands were purified. These DNA fragments were ligated with pSY75 1 that had been digested with PvuII. The products of this reaction were transformed into *E. coli* and selected for growth on the antibiotic ampicillin. Plasmid DNA from individual colonies was analyzed by restriction digestion for the presence of the FCB-SLP polymer gene. Two clones were identified, pSY1520 and 1521, containing the 2.1 and the 2.8 kb inserts, respectively.

*E. coli* cells containing pSY1520 and pSY1521 were grown at 30° C. in LB medium containing 50 $\mu$g/ml ampicillin to an $OD_{600}$ of 0.7. Production of the FCB-SLP polymer proteins were induced by increasing the culture temperature to 42° C. for 1.5 hrs. The cells were harvested by centrifugation and lysed in sample buffer containing sodium dodecylsulfate (SDS) and β-mercaptoethanol by heating at 100° C. for 5 min. Samples of these lysates corresponding to $5\times10^8$ cells were applied to an 8% polyacrylamide gel containing SDS, electrophoresed, and transferred to nitrocellulose filters by electroblotting. The filters were incubated either with anti-SLP or anti-FCB peptide antibody. Specific immunoreactivity with the anti-SLP antibody was observed for a protein band of approximately 75 kd in lysates of pSY 1520, 95 kd in lysates of pSY1521, and 120 kd in lysates of the SLPIII clone pSY1186. Reactivity with the anti-FCB antibody was observed only for the two FCB-SLP polymer bands.

pSY1520 FCB-SLPIII 766 AA MW 57,467

(fM) DPVVLQRRDWENPGVTQLNRLAAHPPFASDPM
GAGS(GAGAGS)$_6$GAAVTGRGDSPASAAGY
[(GAGAGS)$_9$GAAVTGRGDSPASAAGY]$_9$
GAGAGSGAGAGSGAGAMDPGRYQLSAGRYHYQLVWCQK
(SEQ ID NO:88)

Psy1521 FCB-SLPIII 979 AA MW 72,738

(fM) DPVVLQRRDWENPGVTQLNRLAAHPPFASDPM
GAGS(GAGAGS)$_6$GAAVTGRGDSPASAAGY
[(GAGAGS)$_9$GAAVTGRGDSPASAAGY]$_{12}$
GAGAGSGAGAGSGAGAMDPGRYQLSAGRYHYQLVWCQK
(SEQ ID NO:89)

Plasmid pPT0134 Construction:

Two oligonucleotide strands containing multiple cloning sites (MCS) were synthesized and purified as described in Example 1.

FokI FokI ScaI
0.A) 5' - GTGCTGCGGATGCTCGAGATGGTGCATGCATGTACATCCGAGTACTTCGAT
0.B) 3' - ACGCCTACGAGCTCTACCACGTACGTACATGTAGGCTCATGAAGCTA
(SEQ ID NOS:90 & 91)

After annealing, the two oligonucleotide strands were ligated with pSY937 which had been digested with BanI and EcoRV RENs. The product of the ligation mixture was transformed into *E. coli* and selected on bacterial plates containing the antibiotic chloramphenicol. Plasmid DNA from individual colonies was analyzed on agarose gel electrophoresis after digestion with ScaI and StuI RENs. One plasmid, pPT0124, contained the expected DNA fragment.

The new MCS were then moved to plasmid pSY1367. This plasmid is a derivative of pSY1299, which was digested with NciI REN and the large DNA fragment was purified by agarose gel electrophoresis and NACS purification. The purified DNA fragment was treated with DNA Polymerase (Example 1), ligated, then digested with FokI prior to transformation in *E. coli* strain HB101. Plasmid DNA from single colonies was purified and analyzed by restriction digests. One plasmid, pSY1366, was found to be correct and lacking the only FokI site present in pSY1299.

Two oligonucleotide strands were synthesized and purified as described in Example 1:

(BanII) FokI
1.A) 5'- CTACATGTGTTACACATCCCGTGC
(SEQ ID NO:92)

1.B) 3'- CCGAGATGTACACAATGTGTAGGGCACG
(SEQ ID NO:93)

Oligonucleotide strands 1.A and 1.B were annealed and ligated with the DNA of plasmid pSY1366 which had been digested with BanII and FspI RENs. The products of this ligation reaction were transformed into *E. coli* strain HB 101. Plasmid DNA from transformed colonies was purified and digested with Fokl. Clones which linearized with Fokl were sequenced. Plasmid pSY1367 contained the desired MCS sequence and was chosen for subsequent constructions.

Plasmids pPT0124 and pSY1367 were digested with NruI and NcoI and the DNA fragments were purified by agarose gel electrophoresis and NACS purification. The small fragment (approximately 500 bp) from pPT0124 was ligated with the large fragment from pSY1367. The product of the ligation mixture was transformed into *E . coli*. Plasmid DNA from single colonies was purified and analyzed by restriction digests and DNA sequencing. One plasmid, pPT0134, contained the desired sequence and was used as the acceptor vector for further DNA constructions.

SELPF Construction and Expression:

Plasmid DNA pSY1521 was digested with BanI REN and the SLPF (FCB-SlpIII) monomer was purified using NACS column (see Example 1). The DNA fragment was ligated with pPT0134 previously digested with FokI REN, treated with calf intestinal phosphatase (see Example 1), and subsequently purified using NACS column. The product of this ligation reaction was transformed into *E. coli* strain HB 101. Transformants were selected for resistance to chloramphenicol. Plasmid DNA from transformed colonies was purified and digested with FokI. Clones with the correct restriction pattern were sequenced. Plasmid pPT0141 contained the desired SLPF monomer sequence and was chosen for subsequent constructions.

Plasmid pSY1377 was digested with BanI REN and the SELP3 gene monomer DNA fragment was purified by agarose gel electrophoresis followed by NACS column. The purified SELP3 gene monomer, 268 bp, was ligated with plasmid DNA pPT0141 previously digested with Ban I REN and purified using NACS column. The product of this ligation reaction was transformed into *E. coli* strain HB 101. Transformants were selected for resistance to chloramphenicol. Plasmid DNA from transformed colonies was purified and digegsted with Fokl. Clones with the correct restriction pattern were sequenced. Plasmid pPT0146 contained the desired SELPF monomer DNA.

Plasmid DNA from pPT0146 was digested with Fokl REN and the digestion fragments were separated by agarose gel electrophoresis. The SELPF gene fragment, 477 bp, was excised and purified by NACS column (see Example 1). The purified fragment was ligated with plasmid pSY1262 which had been digested with REN BanI. The product of this ligation reaction was transformed into *E. coli* strain HB 101. Transformants were selected for resistance to kanamycin. Plasmid DNA from individual transformants was purified and analyzed for increased size due to SELPF multiple DNA insertion. Several clones were obtained ranging in size from 1 kbp to 6 kbp. One clone pPT0183, with an insert of approximately 2.9 kbp was chosen for expression and protein analysis.

*E. coli* strain HB101 containing plasmid pPT0183 was grown as described in Example 1. The protein produced by these cells was analyzed by SDS-PAGE for detection of reactivity to SLP and ELP antibodies. In every analysis a strong reactive band was observed with an apparent molecular weight of approximately 100 kD.

PPT0183 SELPF 1011 AA MW 75,957
MDPVVLQRRDWENPGVTQLNRLAAHPPFASDPM
GAGS(GAGAGS)$_2$(GVGVP)$_8$
[(GAGAGS)$_{12}$GAAVTGRGDSPASAAGY(GAGAGS)$_5$(GVGVP)$_8$]$_5$
(GAGAGS)$_{12}$GAAVTGRGDSPASAAGY(GAGAGS)$_2$
GAGAMDPGRYQLSAGRYHYQLVWCQK
(SEQ ID NO:94)

Plasmid pPT0285 Construction:

Plasmid pACYC184 (Chang, A. Y. C. and Cohen, S. N., *J. Bacteriol.,* 134:1141–1156 (1978)) was digested with BanI REN, purified by agarose gel electrophoresis, and the DNA fragment corresponding to approximately 2,000 bp was further purified using a NACS column. This DNA fragment was filled in using DNA polymerase (see Example 1) and then self-ligated. The products of the ligation mixture were transformed into *E. coli* strain HB101 and selected on bacterial plates containing chloramphenicol at 30 $\mu$g/ml. Plasmid DNA from individual colonies was linearized by digestion with Eco47III. One clone, pPT0235, was used as the acceptor vector for subsequent DNA manipulations.

Two oligonucleotide strands were synthesized and purified as described in Example 1:

```
    (Eco47III)PmeI     Pm1INruI            BanI        StuI      EcoRV  SnaBI(SnaI)
1.5'-GCTATGTTTAAACCACGTGTTCGCGATCCGGGTGCCGATCCAGGCCTGCGATATCAGTACGTA

2.3'-CGATACAAATTTGGTGCACAAGCGCTAGGCCCACGGCTAGGTCCGGACGCTATAGTCATGCAT
      A  M  F  K  P  R  V  R  D  P  G  A  D  P  G  L  R  Y  Q  Y  V
(SEQ ID NOS:95–97)
```

The two oligonucleotide strands were annealed and ligated with the DNA of plasmid pPT0235 which had been digested with Eco47III and SnaI RENs. The product of this ligation reaction was transformed into *E. coli* strain HB101. Plasmid DNA from transformants was purified and digested with EcoRI in combination with Eco47III or SnaI or NruI RENs. Plasmid DNA from two clones that gave the correct digestion pattern was sequenced. One plasmid, designated pPT0285, was found to be correct and chosen for further constructions.

CIP3.7 Construction and Expression:

One oligonucleotide strand coding for the CLP 3.7 gene monomer (see Table 5) was synthesized using an Applied Biosystems DNA synthesizer model 381A and a 2000Å synthesis column supplied by Glen Research. After the synthesis, the 226 base DNA fragment was deprotected and cleaved from the column support by treatment in $NH_4OH$ at 55° C. for 6 hrs.

TABLE 5

```
5'- ATGGCAGCGAAAGGGGACCGGTGCCCCGGGTACTCCTGGTCCACAAGGTCTGCCGGGAAGCCCAGGG
    GCTCCGGGTACTCCAGGTCCGCAAGGCCTGCCGGGTTCACCGGGTGCTCCGGGAACTCCTGGCCCGC
    AGGGCTTGCCGGGATCCCCAGGTGCACCAGGAACGCCGGGACCTCAGGGTCTTCCGGGTAGCCCTGG
    TGCCTTTCCGCTAAAGTCCTGCCGT -3'
    (SEQ ID NO:98)
```

Two additional DNA strands were synthesized to be used as primers for PCR amplification. The synthesis and purification of these DNA primers was performed as described in Example 1. The two strands are:

```
1. 5'- AAG AAG GAG ATA TCA TAT GGC AGC GAA AGG GGA CC -3'

2. 5'- CGC AGA TCT TTA AAT TAC GGC AGG ACT TTA GCG GAA A -3'

   (SEQ ID NO:99–100)
```

The PCR reaction was performed as described in Example 1.

The DNA was resuspended and digested with BanI REN as described in Example 1. The digested DNA was purified as described in Example 1, and then ligated with pPT0285 previously digested with BanI, treated with SAP, and purified as described in Example 1. The product of the ligation reaction was transformed into *E. coli* strain HB 101. Plasmid DNA from transformants was purified and analyzed as described below. Colonies were picked and transferred onto a plate and into a 0.5 ml microfuge tube containing 50 μl of lysis buffer (1% Tween 20, 10 mM Tris-HCl pH 8.0, 1 mM EDTA). The tube was closed, incubated at 95° C. for 10 min and then cooled to room temperature. 5 μl of lysate was added to 45 μμl MasterMix (1×PCR buffer as described previously, 5 U Amplitaq, 200 μM dNTPs) in a 0.5 ml Perkin Elmer thin-walled Gene Amp™ reaction tube. Amplification ws performed in a Perkin Elmer DNA Thermal cycler model 480 for 30 cycles with the following step cycle of 1 min each:95° C., 52° C., and 72° C. Aliquots from different reactions were analyzed by agarose gel electrophoresis using 1.5% Low Melting Point agarose in 0.5×TAE buffer. Plasmid DNA from the clones showing the correct size insert was purified and anlyzed by DNA sequencing. Plasmid pPT0310 contained the desired CLP 3.7 monomer sequence (see Table 6).

TABLE 6

```
    BanI   AvaI/SmaI
5'- GGTGCCCCGGGTACTCCTGGTCCACAAGGTCTGCCGGGAAGCCCA

3'- CCACGGGGCCCATGAGGACCAGGTGTTCCAGACGGCCCTTCGGGT
    G  A  P  G  T  P  G  P  Q  G  L  P  G  S  P

     BanII        GsuI           StuI          DraIII
    GGGGCTCCGGGTACTCCAGGTCCGCAAGGCCTGCCGGGTTCACCG

    CCCCGAGGCCCATGAGGTCCAGGCGTTCCGGACGGCCCAAGTGGC
```

TABLE 6-continued

```
G   A   P   G   T   P   G   P   Q   G   L   P   G   S   P

                           BG1I           BAMHI
GGTGCTCCGGGAACTCCTGGCCCGCAGGGCTTGCCGGGATCCCCA

CCACGAGGCCCTTGAGGACCGGGCGTCCCGAACGGCCCTAGGGGT
G   A   P   G   T   P   G   P   Q   G   L   P   G   S   P

                          Eco0109I                       BanI
GGTGCACCAGGAACGCCGGGACCTCAGGGTCTTCCGGGTAGCCCTGGTGCC -3'

CCACGTGGTCCTTGCGGCCCTGGAGTCCCAGAAGGCCCATCGGGACCACGG -5'
G   A   P   G   T   P   G   P   Q   G   L   P   G   S   P   (GA)

(SEQ ID NO:101 & 102)
```

CLP3.7 Polymer Construction:

Plasmid DNA from pPT0310 was digested with BanI REN and the digestion fragments were separated by agarose gel electrophoresis. The CLP 3.7 gene fragment, 180 bp, was excised and purified by NACS column (see Methods). The purified fragment was ligated with plasmid pSY1262 which had been prepared as follows: pSY1262 plasmid DNA was digested with BanI REN and subsequently treated with Shrimp Alkaline Phosphatase (SAP) as described in Example 1.

The product of this ligation reaction was transformed into *E. coli* strain HIB 101. Transformants were selected for resistance to kanamycin. Plasmid DNA from individual transformants was purified and analyzed for increased size due to CLP 3.7 multiple DNA insertion. Several clones were obtained and two of them containing inserts of approximately 1.25 kbp and 2.6 kbp (pPT0314 and pPT0312 respectively) were chosen to be used for expression of CP 3.7.

CLP 3.7 Analysis:

*E. coli* strain HB101 containing plasmid pPT0312 or pPT0314 were grown as described in Example 1. The proteins produced by these cells were analyzed by SDS-PAGE for detection of reactivity to CLP antibodies. In every analysis a strong reactive band was observed with an apparent molecular weight of 130 kD and 50 kD respectively.

PPT0312 CLP 3.7 837 AA MW 72,637

MDPVVLQRRDWENPGVTQLNRLAAHPPFASDPM
$[(GAPGTPGPQGLPGSP)_4]_{13}$
GAMDPGRYQLSAGRYHYQLVWCQK
(SEQ ID NO:103)

pPT0314 CLP 3.7 417 AA MW 37,060

MDPVVLQRRDWENPGVTQLNRLAAHPPFASDPM
$[(GAPGTPGPQGLPGSP)_4]_6$
GAMDPGRYQLSAGRYHYQLVWCQK
(SEQ ID NO:104)

Similarly, the following additional polymers have been made:

Slp3-C, Slp-L1, Slp-L2, CLP, CLPβ-CB, KLP 1.2 and KLP 1.3 as described in WO 90/05177;

DCP 1–6 and CLP 3.1 as described in PCT/US92/09485;

Slp F9 and Slp-L3.0 as described in PCT/US94/07776;

SELP4, SELP5, SELP7 and SELP 8 as described in PCT/US95/02772;

and PPAS-A, PPAS1-B, PPAS 1 -C, PPAS 1 -F, PPAS 1 -g, SELP8K and SELP8E as described in PCT/US95/02728; the disclosures of the above applications being herein incorporated by reference.

As is evident from the above results, highly repetitive sequences can be prepared, cloned, and used for expression to produce a wide variety of products which may mimic natural products, such as silk and other proteins and antigens. In addition, novel systems are provided for controlling the expression of the peptide under inducible conditions in a variety of hosts. In this manner, new proteinaceous products can be provided which provide for new properties or may closely mimic the properties of naturally occurring products.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A recombinantly produced protein of from 30 kDal to 250 kDal comprising at least 50 number percent of amino acids of at least one naturally occurring repeating unit of a naturally occurring structural protein, wherein said repeating unit is from 3 to 20 amino acids in length and repeating units having the same amino acid sequence are tandemly repeated at least once in said recombinantly produced protein.

2. The recombinantly produced protein according to claim 1, wherein said repeating unit is of from 3 to 15 amino acids in length.

3. The recombinantly produced protein according to claim 1, wherein said repeating unit is of from 3 to 9 amino acids in length.

4. The recombinantly produced protein according to claim 1, wherein said repeating units are in blocks of at least 2 tandemly repeated repeating units.

5. The recombinantly produced protein according to claim 4, wherein said protein comprises an intervening group of from 1 to 50 amino acids in length between said blocks of tandemly repeated repeating units.

6. A recombinantly produced protein of from 30 kDal to 250 kDal comprising at least 50 number percent of amino acids of at least one naturally occurring repeating unit of a naturally occurring structural protein selected from the group consisting of collagen, elastin, silk, and keratin, wherein said repeating unit is from 3 to 20 amino acids in length and repeating units having the same amino acid sequence are tandemly repeated at least once in said recombinantly produced protein.

7. The recombinantly produced protein according to claim 6, wherein said repeating units are in blocks of at least 2 tandemly repeated repeating units.

8. The recombinantly produced protein according to claim 7, wherein said protein comprises an intervening group of from 1 to 50 amino acids in length between said blocks of tandemly repeated repeating units.

9. The recombinantly produced protein according to claim 6, wherein said repeating unit is selected from.the group consisting of SGAGAG (SEQ ID NO:21) and GAGAGS (SEQ ID NO:41).

10. The recombinantly produced protein according to claim 6, wherein said repeating unit is selected from the group consisting of GVGVP (SEQ ID NO:23), VPGVG (SEQ ID NO:24), and APGVGV (SEQ ID NO:25).

11. The recombinantly produced protein according to claim 6, wherein said repeating unit is G$\alpha\beta$, wherein $\alpha$ and $\beta$ are any amino acid, $\alpha$ and $\beta$ being selected so that said recombinantly produced protein comprises from about 10 to 45 number % proline.

12. The recombinantly produced protein according to claim 6, wherein said repeating unit is K-L-(1)-L-A-E-A (SEQ ID NO:105), wherein 1 is a basic or acidic amino acid, particularly K or E, and the repeating units alternate as to whether 1 is a basic or acidic amino acid.

13. A recombinantly produced protein of from 30 kDal to 250 kDal comprising at least 50 number percent of amino acids of at least one naturally occurring repeating unit of a naturally occurring structural protein, wherein said repeating unit is from 3 to 20 amino acids in length and repeating units having the same amino acid sequence are tandemly repeated at least once in said recombinantly produced protein, further comprising an intervening group of from 1 to 50 amino acids in length between at least 2 repeating units.

14. A formed object comprising the recombinantly produced protein according to claim 1.

15. A formed object comprising the recombinantly produced protein according to claim 6.

16. A formed object comprising the recombinantly produced protein according to claim 13.

* * * * *